(12) United States Patent
Kitano et al.

(10) Patent No.: US 9,368,732 B2
(45) Date of Patent: Jun. 14, 2016

(54) HETEROCYCLIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Atsugi-shi, Kanagawa-ken (JP)

(72) Inventors: Yasushi Kitano, Kanagawa (JP); Hiroshi Kadoma, Kanagawa (JP); Satoko Shitagaki, Kanagawa (JP); Satoshi Seo, Kanagawa (JP); Hiromi Seo, Kanagawa (JP); Tatsuyoshi Takahashi, Kanagawa (JP)

(73) Assignee: Semiconductor Energy Laboratory Co., Ltd., Atsugi-shi, Kanagawa-ken (JP)

(*) Notice: Subject to any disclaimer, the term of this patent is extended or adjusted under 35 U.S.C. 154(b) by 412 days.

(21) Appl. No.: 14/068,319

(22) Filed: Oct. 31, 2013

(65) Prior Publication Data

US 2014/0124764 A1    May 8, 2014

(30) Foreign Application Priority Data

Nov. 2, 2012   (JP) ................................ 2012-243003

(51) Int. Cl.
*H01L 51/00*        (2006.01)
*C07D 405/10*       (2006.01)
(Continued)

(52) U.S. Cl.
CPC .......... *H01L 51/0072* (2013.01); *C07D 209/86* (2013.01); *C07D 405/10* (2013.01);
(Continued)

(58) Field of Classification Search
CPC .... C07D 209/86; C07D 405/10; C09K 11/06; C09K 2211/1416; C09K 2211/1425; C09K 2211/145; C09K 2211/1458; H01L 51/0072; H01L 51/0073
See application file for complete search history.

(56) References Cited

U.S. PATENT DOCUMENTS 6,723,445 B2   4/2004   Li et al.
7,355,340 B2   4/2008   Shitagaki et al.
(Continued)

FOREIGN PATENT DOCUMENTS

CN   101203968 A   6/2008
CN   101853923 A   10/2010
(Continued)

OTHER PUBLICATIONS

Christian Goldsmith et al.; "C—H Bond Activation by a Ferric Methoxide Complex: Modeling the Rate-Determining Step in the Mechanism of Lipoxygenase"; J. Am. Chem. Soc. (Journal of the American Chemical Society); 2002; pp. 83-96; vol. 124, No. 1.
(Continued)

*Primary Examiner* — Dawn L. Garrett
(74) *Attorney, Agent, or Firm* — Fish & Richardson P.C.

(57) ABSTRACT

To provide a novel heterocyclic compound capable of being used as a host material in which a light-emitting substance is dispersed. To provide a light-emitting element having a long lifetime. A heterocyclic compound in which a dibenzo[f,h]quinoxalinyl group and a benzo[b]naphtho[1,2-d]furanyl group are bonded through an arylene group having 6 to 13 carbon atoms. The dibenzo[f,h]quinoxalinyl group, the benzo[b]naphtho[1,2-d]furanyl group, and the arylene group separately are unsubstituted or have, as a substituent, an alkyl group having 1 to 4 carbon atoms or an aryl group having 6 to 13 carbon atoms.

18 Claims, 32 Drawing Sheets

(51) Int. Cl.
  *C07D 209/86* (2006.01)
  *C09K 11/06* (2006.01)
(52) U.S. Cl.
  CPC ........... *C09K 11/06* (2013.01); *H01L 51/0073* (2013.01); *C09K 2211/145* (2013.01); *C09K 2211/1416* (2013.01); *C09K 2211/1425* (2013.01); *C09K 2211/1458* (2013.01)

(56) References Cited

U.S. PATENT DOCUMENTS

| | | | |
|---|---|---|---|
| 7,601,435 B2 | 10/2009 | Shitagaki et al. | |
| 7,927,720 B2 | 4/2011 | Nomura et al. | |
| 7,931,974 B2 | 4/2011 | Egawa et al. | |
| 8,084,146 B2 | 12/2011 | Murase et al. | |
| 8,119,259 B2 | 2/2012 | Kadoma et al. | |
| 8,138,303 B2 | 3/2012 | Chebotareva et al. | |
| 8,178,216 B2 | 5/2012 | Nomura et al. | |
| 8,231,984 B2 | 7/2012 | Shitagaki et al. | |
| 8,252,433 B2 | 8/2012 | Egawa et al. | |
| 8,314,101 B2 | 11/2012 | Kadoma et al. | |
| 2006/0040131 A1* | 2/2006 | Klubek .................. | C09K 11/06 428/690 |
| 2009/0026922 A1 | 1/2009 | Iwaki et al. | |
| 2009/0072718 A1 | 3/2009 | Nomura et al. | |
| 2009/0140641 A1 | 6/2009 | Nomura et al. | |
| 2009/0140642 A1 | 6/2009 | Kadoma et al. | |
| 2009/0153041 A1 | 6/2009 | Kawakami et al. | |
| 2009/0184633 A1 | 7/2009 | Kadoma et al. | |
| 2009/0203704 A1 | 8/2009 | Kadoma et al. | |
| 2010/0039024 A1 | 2/2010 | Wendeborn et al. | |
| 2010/0090588 A1 | 4/2010 | Yokoyama et al. | |
| 2010/0249349 A1 | 9/2010 | Chebotareva et al. | |
| 2011/0089407 A1 | 4/2011 | Schmidhalter et al. | |
| 2011/0210316 A1 | 9/2011 | Kadoma et al. | |
| 2012/0138907 A1 | 6/2012 | Murase et al. | |
| 2012/0138914 A1 | 6/2012 | Kawamura et al. | |
| 2012/0165556 A1 | 6/2012 | Suzuki et al. | |
| 2012/0193613 A1 | 8/2012 | Kadoma et al. | |
| 2012/0197020 A1 | 8/2012 | Osaka et al. | |
| 2012/0286257 A1 | 11/2012 | Shitagaki et al. | |
| 2012/0313506 A1 | 12/2012 | Egawa et al. | |
| 2013/0009543 A1 | 1/2013 | Kadoma et al. | |
| 2013/0048971 A1 | 2/2013 | Kitano et al. | |
| 2013/0060033 A1 | 3/2013 | Seo et al. | |
| 2013/0075704 A1 | 3/2013 | Takasu et al. | |
| 2013/0082591 A1 | 4/2013 | Seo et al. | |
| 2013/0112954 A1 | 5/2013 | Osaka et al. | |
| 2014/0124764 A1* | 5/2014 | Kitano ................. | H01L 51/0072 257/40 |
| 2015/0031900 A1* | 1/2015 | Kawakami .......... | H01L 51/0054 549/457 |
| 2015/0034928 A1* | 2/2015 | Yamamoto .............. | H01L 27/32 257/40 |
| 2015/0060813 A1* | 3/2015 | Kawakami .......... | H01L 51/0052 257/40 |

FOREIGN PATENT DOCUMENTS

| | | | |
|---|---|---|---|
| CN | 101867019 A | 10/2010 | |
| CN | 101970448 A | 2/2011 | |
| CN | 102190653 A | 9/2011 | |
| CN | 102448945 A | 5/2012 | |
| CN | 103030632 A | 4/2013 | |
| EP | 1 616 864 A1 | 1/2006 | |
| EP | 1 748 045 A1 | 1/2007 | |
| EP | 1 905 768 A1 | 4/2008 | |
| EP | 1 962 354 A1 | 8/2008 | |
| EP | 2 055 704 A1 | 5/2009 | |
| EP | 2 065 378 A1 | 6/2009 | |
| EP | 2 236 506 A1 | 10/2010 | |
| EP | 2 363 398 A1 | 9/2011 | |
| EP | 2 436 679 A1 | 4/2012 | |
| EP | 2 450 356 A1 | 5/2012 | |
| JP | 2006-324650 A | 11/2006 | |
| JP | 2007-189001 A | 7/2007 | |
| JP | 2008-106051 A | 5/2008 | |
| JP | 2008-239613 A | 10/2008 | |
| JP | 2009-149629 A | 7/2009 | |
| JP | 2009-149631 A | 7/2009 | |
| JP | 2009-149632 A | 7/2009 | |
| JP | 2009-526111 A | 7/2009 | |
| JP | 2011-511821 A | 4/2011 | |
| JP | 2011-201869 A | 10/2011 | |
| JP | 2012-149045 A | 8/2012 | |
| JP | 2013-035825 A | 2/2013 | |
| JP | 2013-060459 A | 4/2013 | |
| KR | 2008-0005441 A | 1/2008 | |
| KR | 2010-0123716 A | 11/2010 | |
| KR | 2011-0042004 A | 4/2011 | |
| KR | 2011-0099173 A | 9/2011 | |
| KR | 2012-0038402 A | 4/2012 | |
| KR | 2013-0006572 A | 1/2013 | |
| TW | 200940554 A | 10/2009 | |
| TW | 201105679 A1 | 2/2011 | |
| TW | 201202225 A1 | 1/2012 | |
| TW | 201240980 A1 | 10/2012 | |
| TW | 201302977 A1 | 1/2013 | |
| TW | 201319059 A1 | 5/2013 | |
| WO | 03/058667 A1 | 7/2003 | |
| WO | 2004/043937 A1 | 5/2004 | |
| WO | 2004/094389 A1 | 11/2004 | |
| WO | 2005/113531 A1 | 12/2005 | |
| WO | 2006/115232 A1 | 11/2006 | |
| WO | 2007/069569 A1 | 6/2007 | |
| WO | 2007/090773 A1 | 8/2007 | |
| WO | 2008/023628 A1 | 2/2008 | |
| WO | 2008/031743 A1 | 3/2008 | |
| WO | 2009/100991 A1 | 8/2009 | |
| WO | 2010/137285 A1 | 12/2010 | |
| WO | 2012/090970 A1 | 7/2012 | |

OTHER PUBLICATIONS

Toshihiro Ohnishi et al.; "A Method Measuring an Energy Level"; High Molecular EL materials—development of light-emitting high molecular compounds—; Dec. 25, 2004; pp. 64-67; Kyoritsu Shuppan; with English translation.

Ming Zhang et al.; "Highly-efficient solution-processed OLEDs based on new bipolar emitters"; Chemical Communications; 2010; pp. 3923-3925; vol. 46.

International Search Report (Application No. PCT/JP2013/079657) dated Dec. 3, 2013, 3 pages.

Written Opinion (Application No. PCT/JP2013/079657) dated Dec. 3, 2013, 3 pages.

* cited by examiner

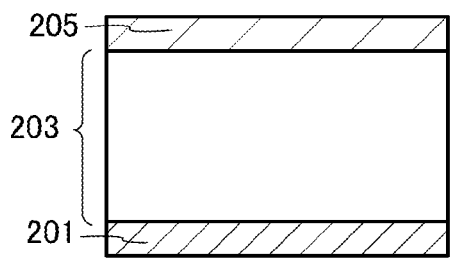
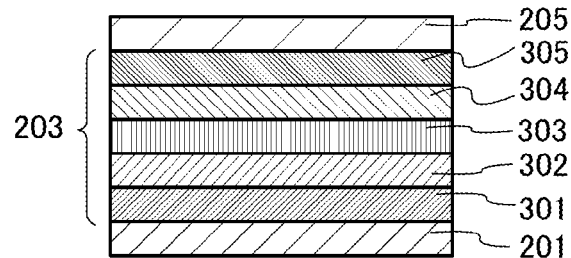
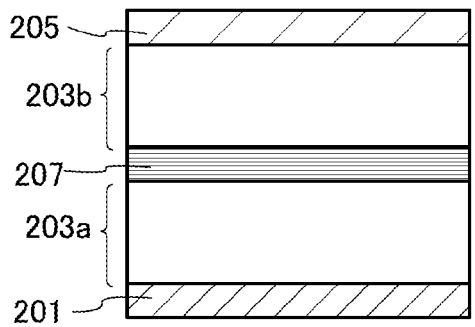
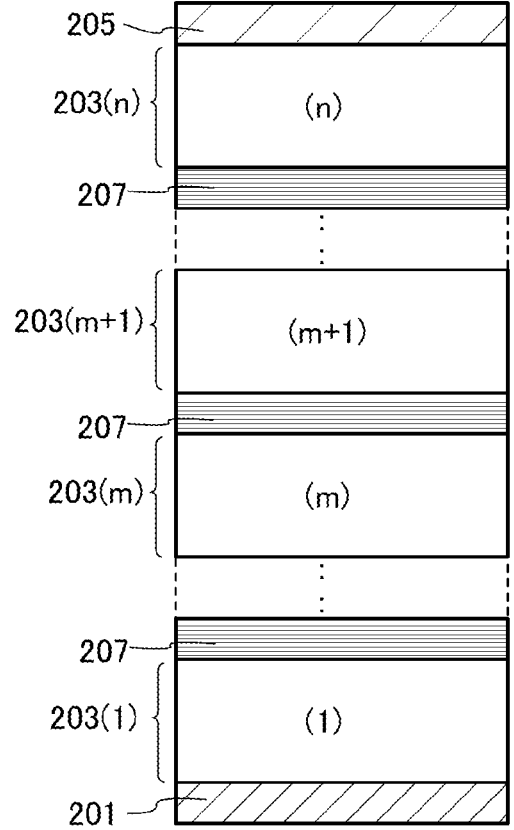

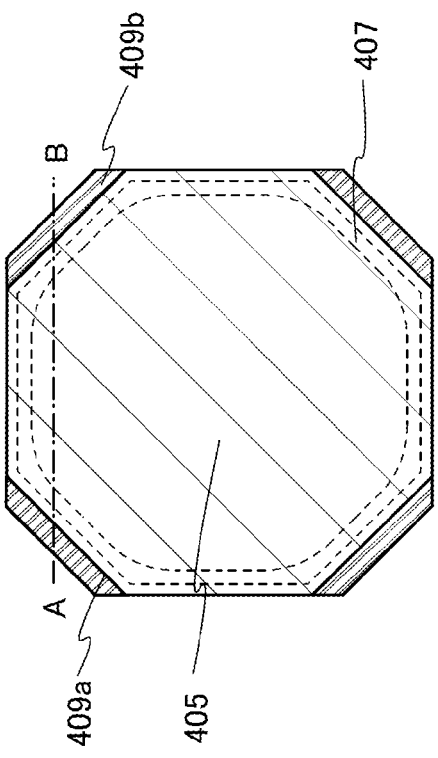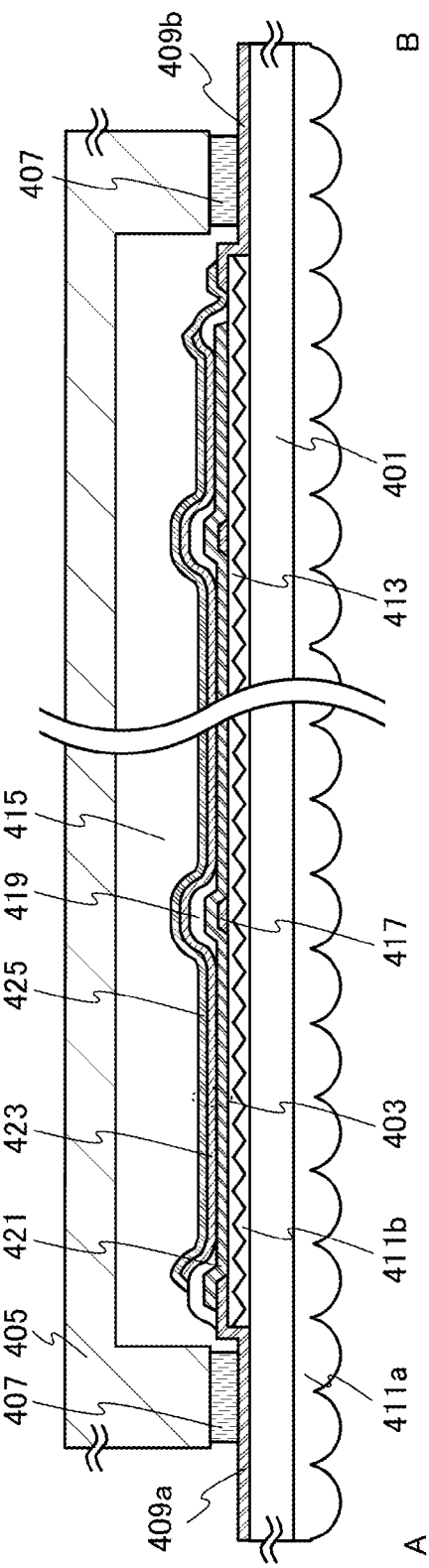

US 9,368,732 B2

HETEROCYCLIC COMPOUND, LIGHT-EMITTING ELEMENT, LIGHT-EMITTING DEVICE, ELECTRONIC DEVICE, AND LIGHTING DEVICE

TECHNICAL FIELD

The present invention relates to a heterocyclic compound, a light-emitting element utilizing electroluminescence (EL) (the light-emitting element is also referred to as an EL element), a light-emitting device, an electronic device, and a lighting device.

BACKGROUND ART

In recent years, a light-emitting element using an organic compound as a light-emitting substance (the light-emitting element is also referred to as an organic EL element) has been actively researched and developed. In a basic structure of the light-emitting element, a layer containing a light-emitting substance is provided between a pair of electrodes. Voltage application to this element causes the light-emitting substance to emit light.

The light-emitting element is a self-luminous element and thus has advantages over a liquid crystal display element, such as high visibility of the pixels and no need of backlight, and is considered to be suitable as a flat panel display element. Another major advantage of the light-emitting element is that it can be fabricated to be thin and lightweight. Besides, the EL element has an advantage of quite fast response speed.

Since the light-emitting element can be formed in a film form, planar light emission can be provided; thus, a large-area element can be easily formed. This feature is difficult to obtain with point light sources typified by incandescent lamps and LEDs or linear light sources typified by fluorescent lamps. Thus, the light-emitting element also has great potential as a planar light source applicable to a lighting device and the like.

In the case of a light-emitting element in which a layer containing an organic compound used as a light-emitting substance is provided between a pair of electrodes, by applying a voltage to the element, electrons from a cathode and holes from an anode are injected into the layer containing the organic compound and thus a current flows. The injected electrons and holes then lead the organic compound to its excited state, so that light emission is provided from the excited organic compound.

The excited state formed by an organic compound can be a singlet excited state or a triplet excited state. Light emission from the singlet excited state (S*) is called fluorescence, and light emission from the triplet excited state (T*) is called phosphorescence. The statistical generation ratio thereof in the light-emitting element is considered to be S*:T*=1:3.

At room temperature, a compound capable of converting a singlet excited state into light emission (hereinafter, referred to as a fluorescent compound) exhibits only light emission from the singlet excited state (fluorescence), and light emission from the triplet excited state (phosphorescence) cannot be observed. Accordingly, the internal quantum efficiency (the ratio of the number of generated photons to the number of injected carriers) of a light-emitting element including the fluorescent compound is assumed to have a theoretical limit of 25%, on the basis of S*:T*=1:3.

In contrast, a compound capable of converting a triplet excited state into light emission (hereinafter, referred to as a phosphorescent compound) exhibits light emission from the triplet excited state (phosphorescence). Further, since intersystem crossing (i.e., transition from a singlet excited state to a triplet excited state) easily occurs in a phosphorescent compound, the internal quantum efficiency can be theoretically increased to 100%. That is, higher emission efficiency can be achieved than using a fluorescent compound. For this reason, light-emitting elements using a phosphorescent compound have been under active development recently so that high-efficiency light-emitting elements can be achieved.

When a light-emitting layer of a light-emitting element is formed using the phosphorescent compound described above, in order to inhibit concentration quenching or quenching due to triplet-triplet annihilation of the phosphorescent compound, the light-emitting layer is usually formed such that the phosphorescent compound is dispersed in a matrix of another compound. Here, the compound serving as the matrix is called host material, and the compound dispersed in the matrix like the phosphorescent compound is called guest material.

When a phosphorescent compound is a guest material, a host material needs to have higher triplet excitation energy (energy difference between a ground state and a triplet excited state) than the phosphorescent compound.

Furthermore, since singlet excitation energy (energy difference between a ground state and a singlet excited state) is higher than triplet excitation energy, a substance that has high triplet excitation energy also has high singlet excitation energy. Thus, the above substance that has high triplet excitation energy is also effective in a light-emitting element using a fluorescent compound as a light-emitting substance.

Studies have been conducted on compounds having dibenzo[f,h]quinoxaline rings, which are examples of the host material used when a phosphorescent compound is a guest material (e.g., see Patent Documents 1 and 2).

REFERENCE

Patent Document

[Patent Document 1] International Publication WO 03/058667 pamphlet
[Patent Document 2] Japanese Published Patent Application No. 2007-189001

DISCLOSURE OF INVENTION

In improving element characteristics of a light-emitting element, there are many problems which depend on substances used for the light-emitting element. Therefore, improvement in an element structure, development of a substance, and the like have been carried out in order to solve the problems. Development of light-emitting elements leaves room for improvement in terms of emission efficiency, reliability, cost, and the like.

For practical use of a display or lighting which uses a light-emitting element, a long lifetime of the light-emitting element has been required.

Thus, an object of one embodiment of the present invention is to provide a novel heterocyclic compound which can be used in a light-emitting element as a host material in which a light-emitting substance is dispersed. Another object of one embodiment of the present invention is to provide a light-emitting element having a long lifetime.

A further object of one embodiment of the present invention is to provide a highly reliable light-emitting device, a highly reliable electronic device, or a highly reliable lighting device using the light-emitting element.

One embodiment of the present invention is a heterocyclic compound in which a dibenzo[f,h]quinoxaline skeleton and a benzo[b]naphtho[1,2-d]furan skeleton are bonded through an arylene skeleton.

A dibenzo[f,h]quinoxaline skeleton has a planar structure. An organic compound having a planar structure is easily crystallized. A light-emitting element using an organic compound that is easily crystallized has a short lifetime. However, the heterocyclic compound of one embodiment of the present invention has a sterically bulky structure since a benzo[b]naphtho[1,2-d]furan skeleton is bonded to a dibenzo[f,h]quinoxaline skeleton through an arylene skeleton. The heterocyclic compound of one embodiment of the present invention is not easily crystallized, which can inhibit a reduction in lifetime of a light-emitting element. In addition, the heterocyclic compound of one embodiment of the present invention has high heat resistance. Furthermore, the heterocyclic compound of one embodiment of the present invention can accept electrons and holes since the heterocyclic compound has a dibenzo[f,h]quinoxaline skeleton as an electron-transport skeleton and a benzo[b]naphtho[1,2-d]furan skeleton as a hole-transport skeleton. Accordingly, by the use of the heterocyclic compound of one embodiment of the present invention as a host material of a light-emitting layer, electrons and holes recombine in the light-emitting layer and it is possible to inhibit a reduction in lifetime of a light-emitting element. Thus, by the use of the heterocyclic compound of one embodiment of the present invention, the light-emitting element can have a long lifetime.

Specifically, one embodiment of the present invention is a heterocyclic compound represented by General Formula (G0).

[Chemical formula 1]

$A^1$-Ar-$A^2$ (G0)

In General Formula (G0), $A^1$ represents a dibenzo[f,h]quinoxalinyl group, $A^2$ represents a benzo[b]naphtho[1,2-d]furanyl group, and Ar represents an arylene group having 6 to 13 carbon atoms. The dibenzo[f,h]quinoxalinyl group, the benzo[b]naphtho[1,2-d]furanyl group, and the arylene group separately are unsubstituted or have, as a substituent, an alkyl group having 1 to 4 carbon atoms or an aryl group having 6 to 13 carbon atoms.

Further, one embodiment of the present invention is a heterocyclic compound represented by General Formula (G1).

[Chemical formula 2]

(G1)

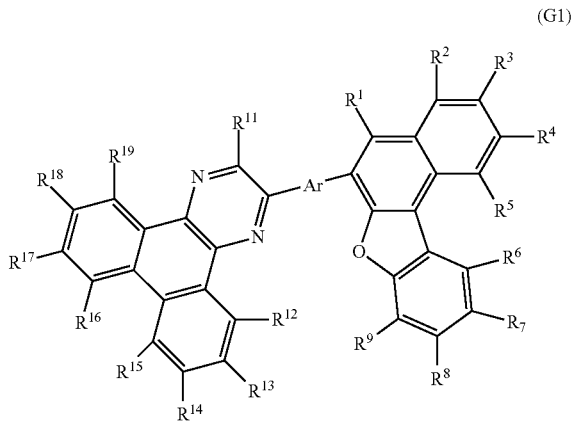

In General Formula (G1), $R^1$ to $R^9$ and $R^{11}$ to $R^{19}$ separately represent hydrogen, an alkyl group having 1 to 4 carbon atoms, or an aryl group having 6 to 13 carbon atoms, and Ar represents an arylene group having 6 to 13 carbon atoms. The aryl group and the arylene group separately are unsubstituted or have, as a substituent, an alkyl group having 1 to 4 carbon atoms or an aryl group having 6 to 13 carbon atoms.

One embodiment of the present invention is a light-emitting element which has a layer containing the heterocyclic compound represented by General Formula (G0) or (G1) between a pair of electrodes.

One embodiment of the present invention is a light-emitting element which has a layer containing a heterocyclic compound between a pair of electrodes and in which the heterocyclic compound has a dibenzo[f,h]quinoxaline skeleton and a benzo[b]naphtho[1,2-d]furan skeleton.

One embodiment of the present invention is a light-emitting element which has a layer containing a heterocyclic compound between a pair of electrodes and in which the heterocyclic compound is a heterocyclic compound where a dibenzo[f,h]quinoxaline skeleton and a benzo[b]naphtho[1,2-d]furan skeleton are bonded through an arylene skeleton.

One embodiment of the present invention is a light-emitting device including any of the above-described light-emitting elements in a light-emitting portion. One embodiment of the present invention is an electronic device including the light-emitting device in a display portion. One embodiment of the present invention is a lighting device including the light-emitting device in a light-emitting portion.

The light-emitting element of one embodiment of the present invention has a long lifetime; thus, a highly reliable light-emitting device can be provided. Similarly, a highly reliable electronic device and a highly reliable lighting device can be achieved by application of one embodiment of the present invention.

The light-emitting device in this specification includes an image display device that uses a light-emitting element. The category of the light-emitting device in this specification includes a module in which a light-emitting element is provided with a connector such as an anisotropic conductive film or a TCP (tape carrier package); a module in which a printed wiring board is provided at the end of a TCP; and a module in which an IC (integrated circuit) is directly mounted on a light-emitting element by a COG (chip on glass) method. In addition, a light-emitting device that is used in lighting equipment and the like are also included.

One embodiment of the present invention provides a novel heterocyclic compound capable of being used as a host material in which a light-emitting substance is dispersed. The heterocyclic compound of one embodiment of the present invention has features of a sterically bulky structure and high heat resistance; thus, by the use of the heterocyclic compound in a light-emitting element, the light-emitting element can have a long lifetime. By the use of the light-emitting element, a light-emitting device, an electronic device, and a lighting device each having high reliability can be provided.

BRIEF DESCRIPTION OF DRAWINGS

FIGS. 1A to 1D each illustrate an example of a light-emitting element of one embodiment of the present invention.

FIGS. 2A and 2B illustrate an example of a light-emitting device of one embodiment of the present invention.

BEST MODE FOR CARRYING OUT THE INVENTION

Figure 3A:
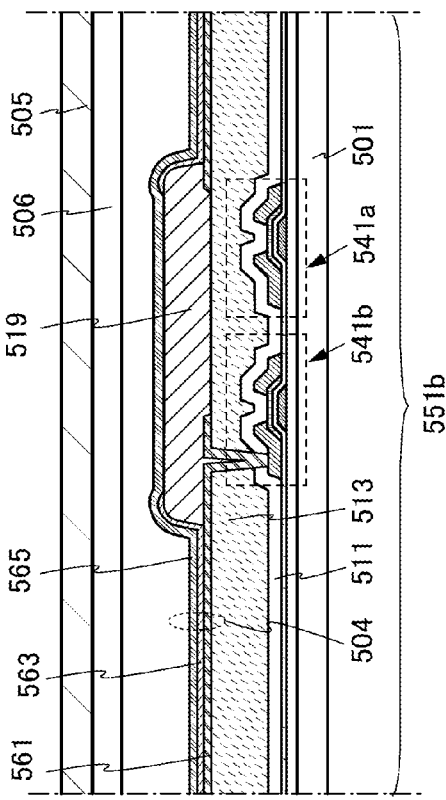
FIGS. 3A to 3C illustrate examples of light-emitting devices of embodiments of the present invention.

Embodiments of the present invention will be described with reference to the drawings. Note that the present invention is not limited to the following description, and it is easily understood by those skilled in the art that various changes for embodiments and details can be made without departing from the spirit and scope of the invention. Therefore, the present invention should not be construed as being limited to the description in the following embodiments. Note that in the structures of the invention described below, the same portions or portions having similar functions are denoted by the same reference numerals in different drawings, and description of such portions is not repeated.

Embodiment 1

In this embodiment, a heterocyclic compound of one embodiment of the present invention is described.

One embodiment of the present invention is a heterocyclic compound in which a dibenzo[f,h]quinoxaline skeleton and a benzo[b]naphtho[1,2-d]furan skeleton are bonded through an arylene skeleton.

A dibenzo[f,h]quinoxaline skeleton has a planar structure. An organic compound having a planar structure is easily crystallized. A light-emitting element using an organic compound that is easily crystallized has a short lifetime. However, the heterocyclic compound of one embodiment of the present invention has a sterically bulky structure since a benzo[b]naphtho[1,2-d]furan skeleton is bonded to a dibenzo[f,h]quinoxaline skeleton through an arylene skeleton. The heterocyclic compound of one embodiment of the present invention is not easily crystallized, which can inhibit a reduction in lifetime of a light-emitting element. In addition, the heterocyclic compound of one embodiment of the present invention has high heat resistance and thus when used in a light-emitting element, the light-emitting element can have a long lifetime.

When a compound that cannot easily accept electrons or holes is used as a host material in a light-emitting layer, the regions of electron-hole recombination concentrate on an interface between the light-emitting layer and a different layer, leading to a reduction in lifetime of a light-emitting element. Here, the heterocyclic compound of one embodiment of the present invention can easily accept electrons and holes since the heterocyclic compound has a dibenzo[f,h]quinoxaline skeleton as an electron-transport skeleton and a benzo[b]naphtho[1,2-d]furan skeleton as a hole-transport skeleton. Accordingly, by the use of the heterocyclic compound of one embodiment of the present invention as the host material of the light-emitting layer, electrons and holes recombine in the light-emitting layer and it is possible to inhibit a reduction in lifetime of the light-emitting element.

As compared to extension of a conjugation system in a heterocyclic compound in which a dibenzo[f,h]quinoxaline skeleton and a benzo[b]naphtho[1,2-d]furan skeleton are directly bonded, extension of a conjugated system in the heterocyclic compound of one embodiment of the present invention in which the two skeletons are bonded through an arylene group is small; accordingly, reductions in band gap and triplet excitation energy can be prevented. Moreover, the heterocyclic compound of one embodiment of the present invention is also advantageous in that its purification is easy and film quality is high.

The heterocyclic compound of one embodiment of the present invention has a wide band gap. Accordingly, the heterocyclic compound can be favorably used as a host material, in which a light-emitting substance is dispersed, of a light-emitting layer in a light-emitting element. It is particularly preferable that the heterocyclic compound of one embodiment of the present invention be used as a host material in which a phosphorescent compound emitting light in a wavelength range from red to yellow green is dispersed.

Further, since the heterocyclic compound of one embodiment of the present invention has a high electron-transport property, the heterocyclic compound can be suitably used as a material for an electron-transport layer in a light-emitting element.

Thus, the heterocyclic compound of one embodiment of the present invention can be suitably used as a material for an organic device such as a light-emitting element or an organic transistor.

Specifically, one embodiment of the present invention is a heterocyclic compound represented by General Formula (G0).

[Chemical formula 3]

$$A^1\text{-}Ar\text{-}A^2 \quad (G0)$$

In General Formula (G0), $A^1$ represents a dibenzo[f,h]quinoxalinyl group, $A^2$ represents a benzo[b]naphtho[1,2-d]furanyl group, and Ar represents an arylene group having 6 to 13 carbon atoms. The dibenzo[f,h]quinoxalinyl group, the benzo[b]naphtho[1,2-d]furanyl group, and the arylene group separately are unsubstituted or have, as a substituent, an alkyl group having 1 to 4 carbon atoms or an aryl group having 6 to 13 carbon atoms.

Further, one embodiment of the present invention is a heterocyclic compound represented by General Formula (G1).

[Chemical formula 4]

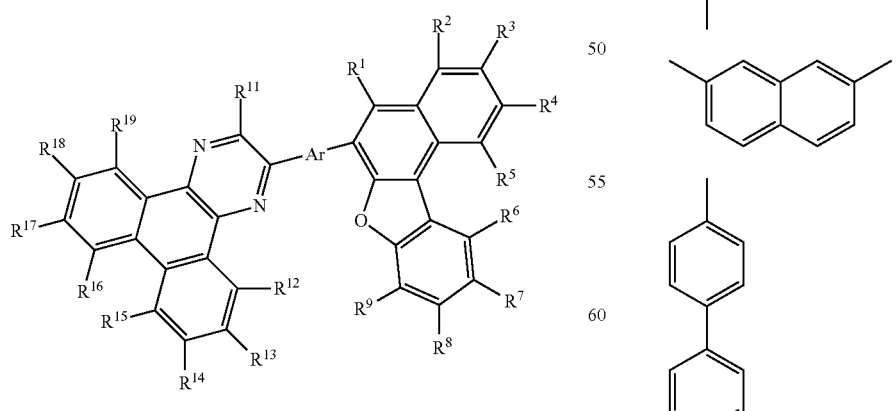

(G1)

In General Formula (G1), $R^1$ to $R^9$ and $R^{11}$ to $R^{19}$ separately represent hydrogen, an alkyl group having 1 to 4 carbon atoms, or an aryl group having 6 to 13 carbon atoms, and Ar represents an arylene group having 6 to 13 carbon atoms. The aryl group and the arylene group separately are unsubstituted or have, as a substituent, an alkyl group having 1 to 4 carbon atoms or an aryl group having 6 to 13 carbon atoms.

Specific examples of the structure of Ar in General Formulae (G0) and (G1) include substituents represented by Structural Formulae (1-1) to (1-15). Note that Ar having any of the structures represented by Structural Formulae (1-1) to (1-15) may further have, as a substituent, an alkyl group having 1 to 4 carbon atoms or an aryl group having 6 to 13 carbon atoms.

[Chemical formula 5]

(1-1)

(1-2)

(1-3)

(1-4)

(1-5)

(1-6)

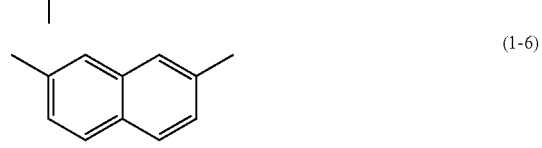

(1-7)

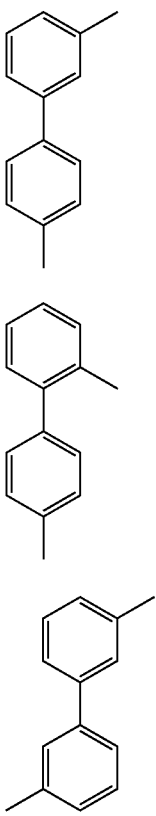
(1-8)
(1-9)
(1-10)
(1-11)
(1-12)
(1-13)
(1-14)
(1-15)
Specific examples of the structures of $R^1$ to $R^9$ and $R^{11}$ to $R^{19}$ in General Formulae (G0) and (G1) include substituents represented by Structural Formulae (2-1) to (2-23). Note that the structures represented by Structural Formulae (2-10) to (2-23) may further have, as a substituent, an alkyl group having 1 to 4 carbon atoms or an aryl group having 6 to 13 carbon atoms.
[Chemical formula 6]
(2-1)
(2-2)
(2-3)
(2-4)
(2-5)
(2-6)

(2-7) 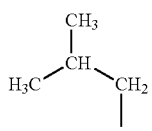
(2-8) 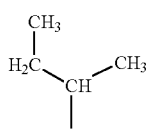
(2-9) 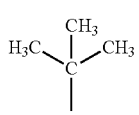
(2-10) 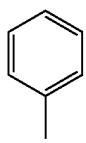
(2-11) 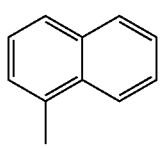
(2-12) 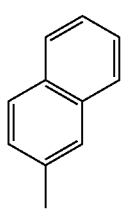
(2-13) 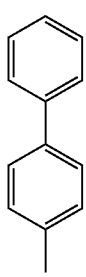
(2-14) 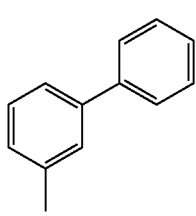
(2-15) 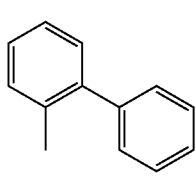
(2-16) 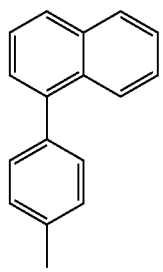
(2-17) 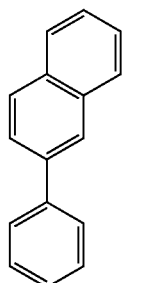
(2-18) 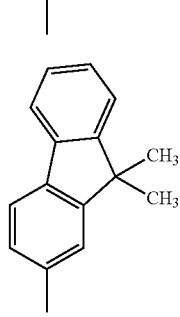
(2-19) 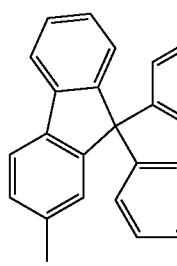
(2-20) 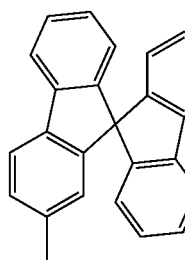
(2-21) 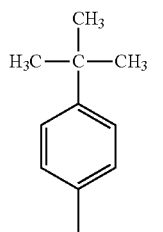

(2-22)
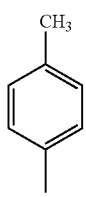
(2-23)
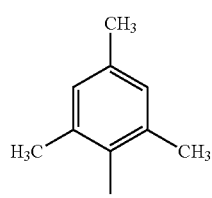
Specific examples of the heterocyclic compound of one embodiment of the present invention include heterocyclic compounds represented by Structural Formulae (200) to (270). However, the present invention is not limited to the following structural formulae.
[Chemical formula 7]
(200)
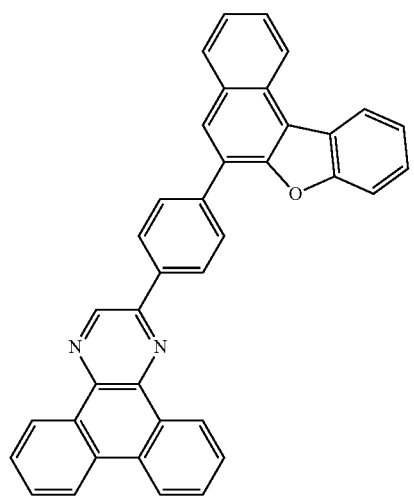
(201)
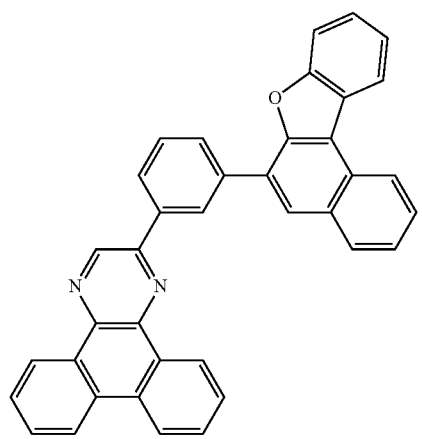
(202)
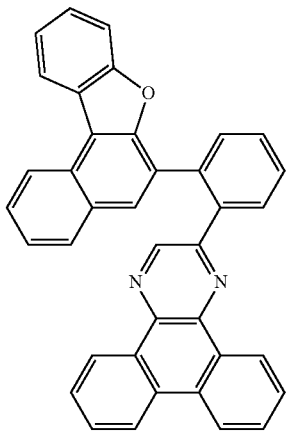
(203)
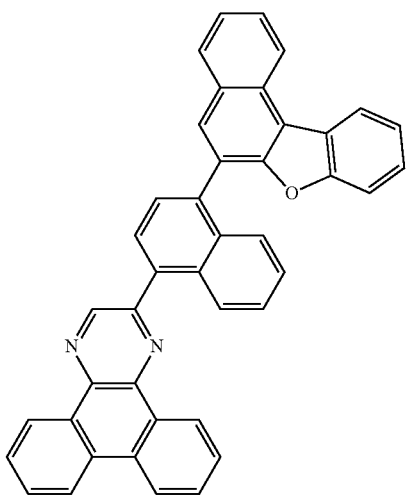
(204)
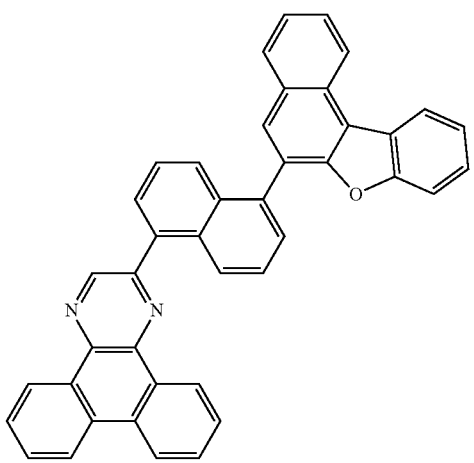

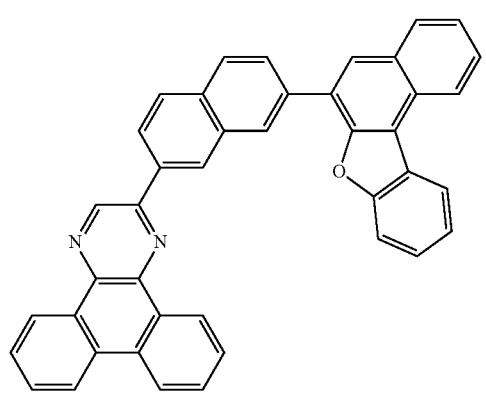
(205)
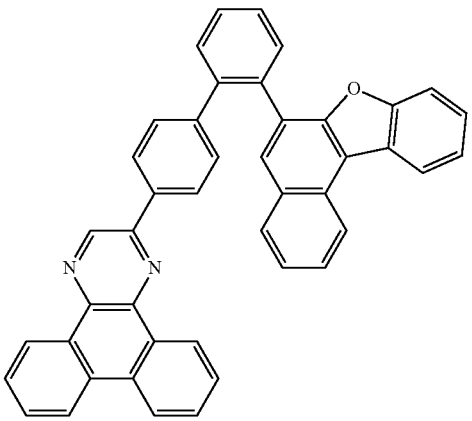
(208)
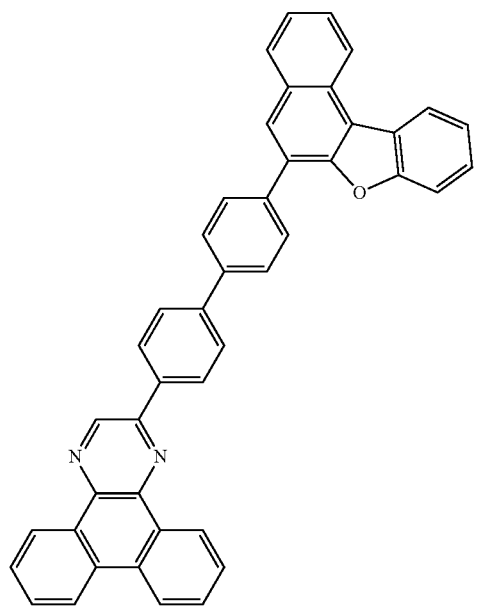
(206)
[Chemical formula 8]
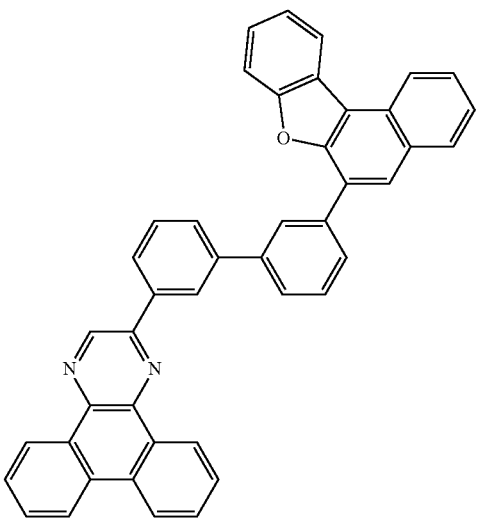
(209)
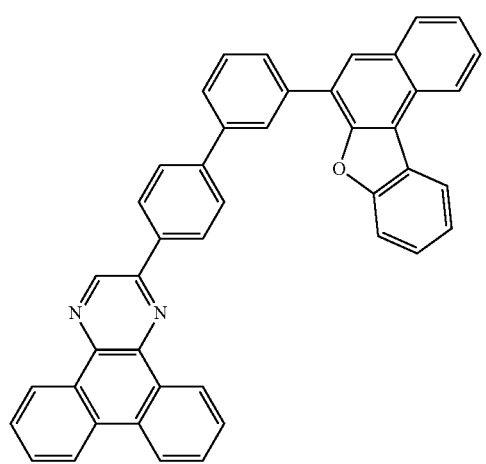
(207)
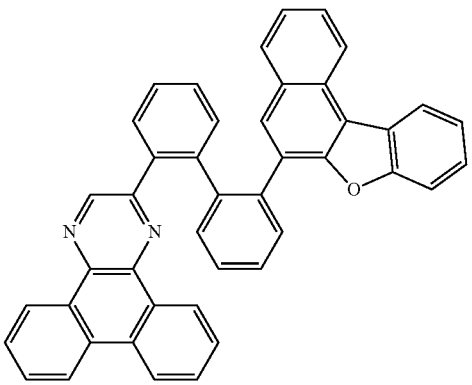
(210)

(211)
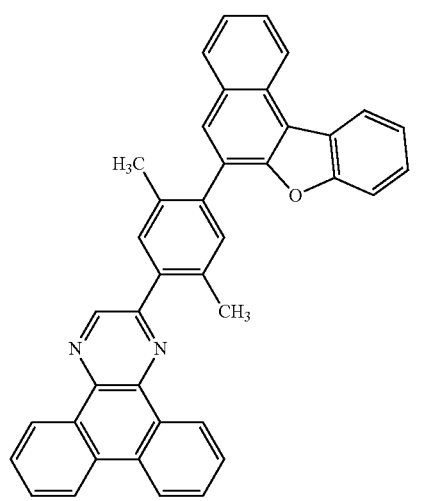
(212)
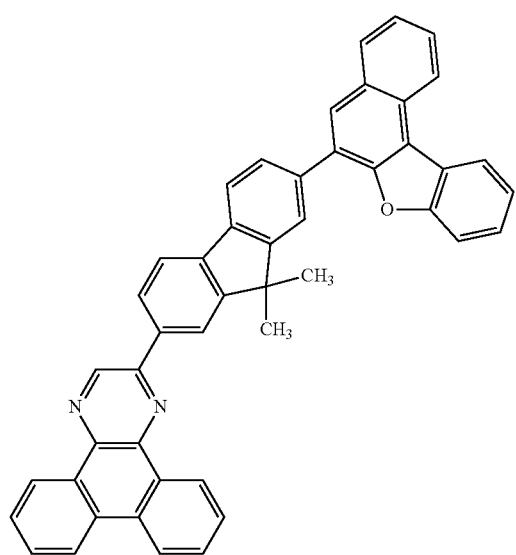
(213)
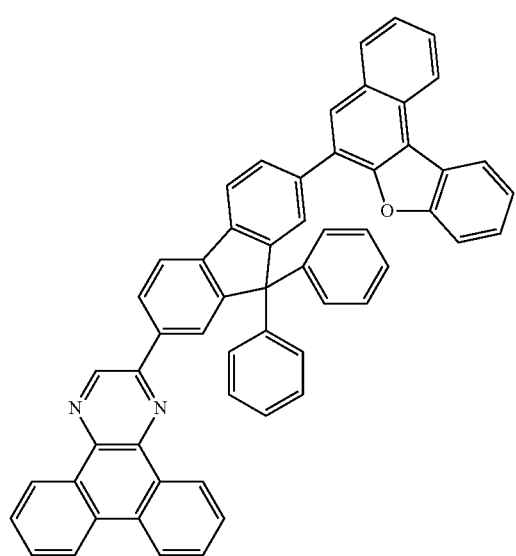
(214)
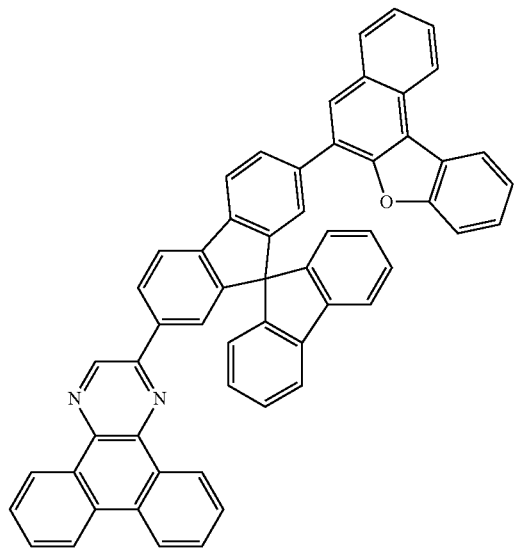
(215)
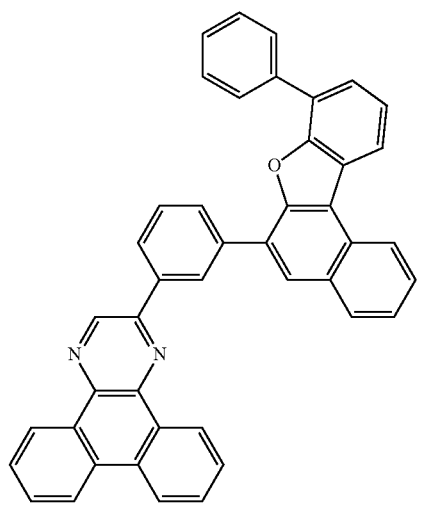
[Chemical formula 9]
(216)
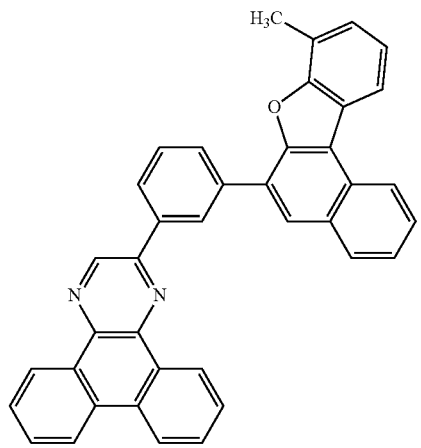

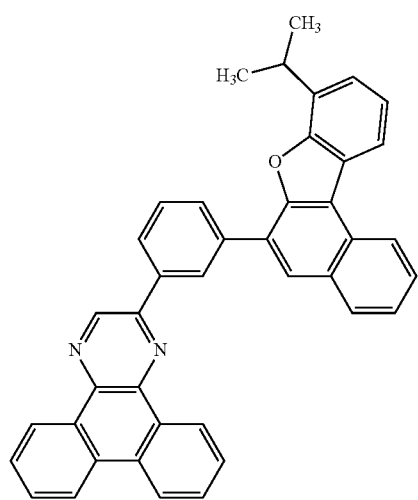
(217)
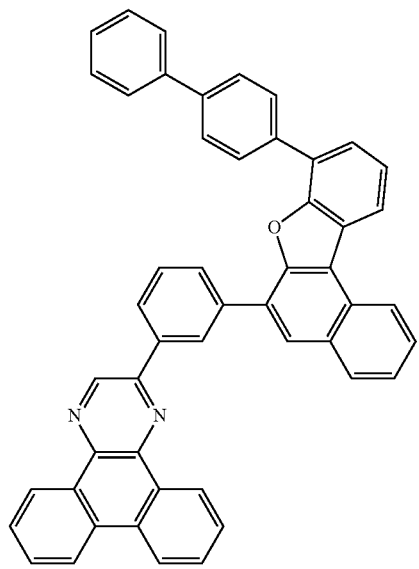
(220)
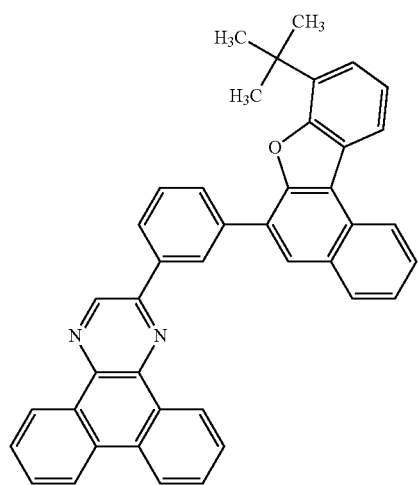
(218)
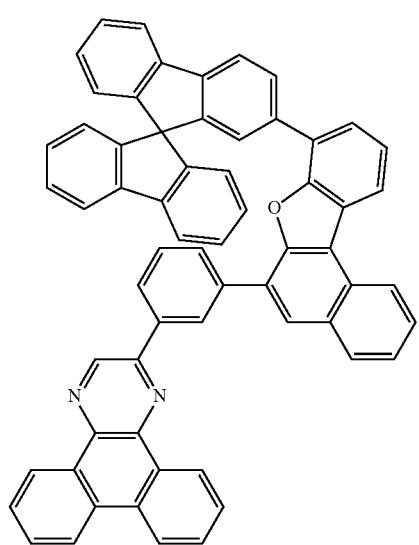
(221)
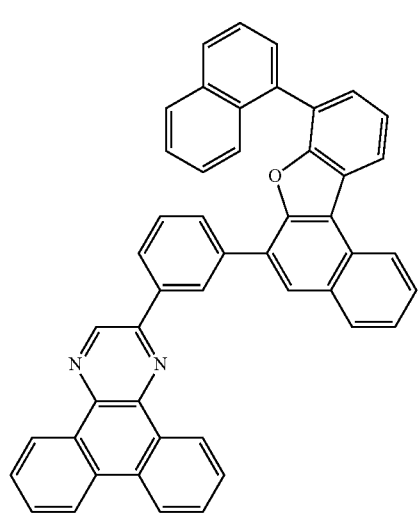
(219)
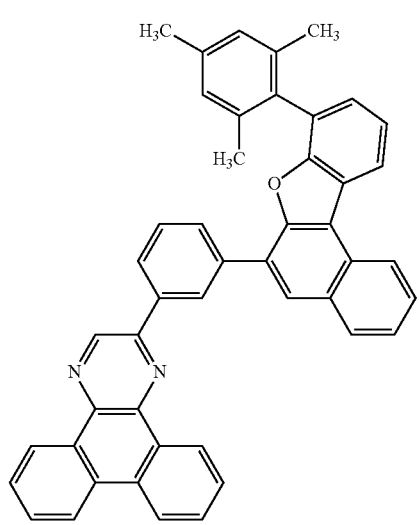
(222)

(223)
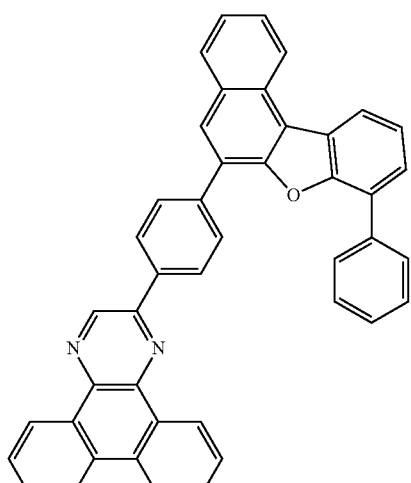
[Chemical formula 10]
(224)
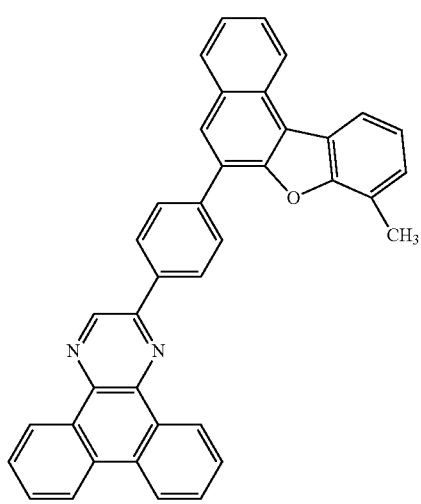
(225)
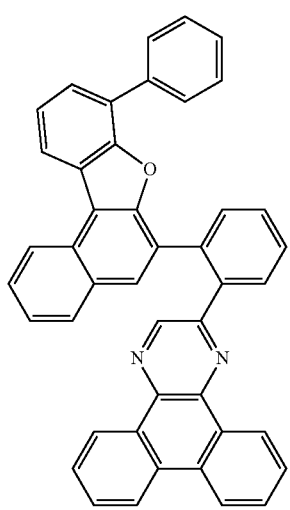
(226)
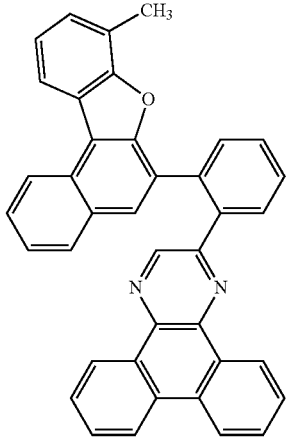
(227)
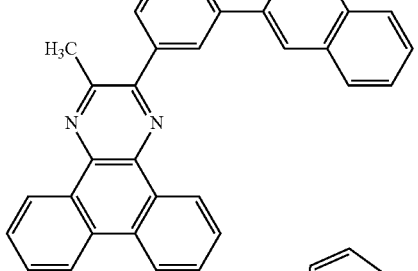
(228)
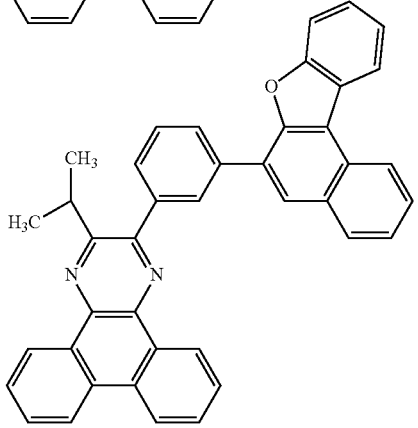
(229)
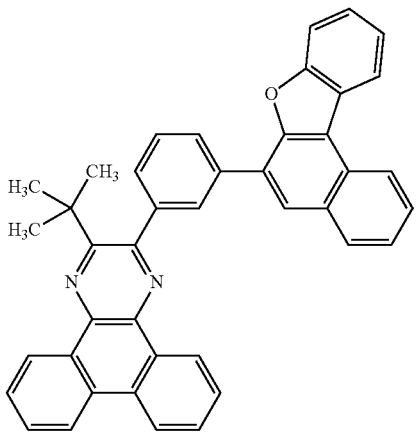

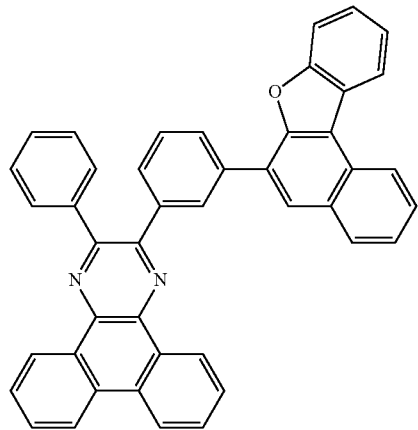 (230)
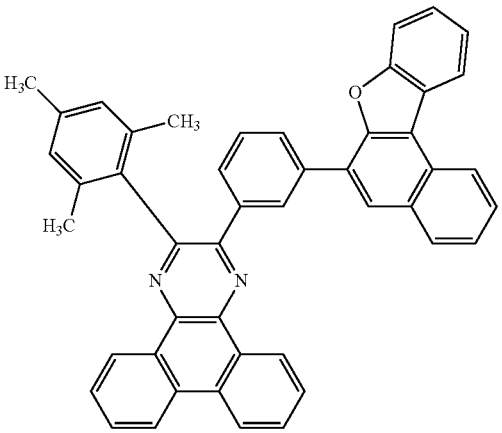 (233)
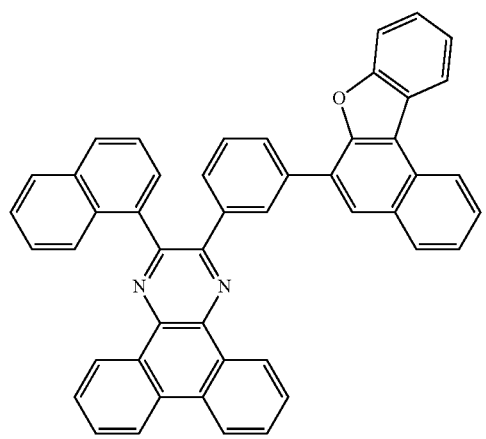 (231)
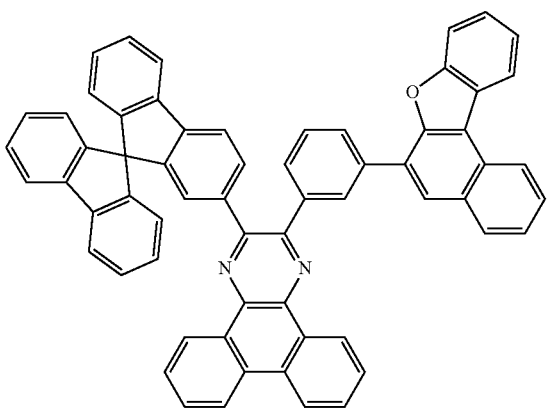 (234)
[Chemical formula 11]
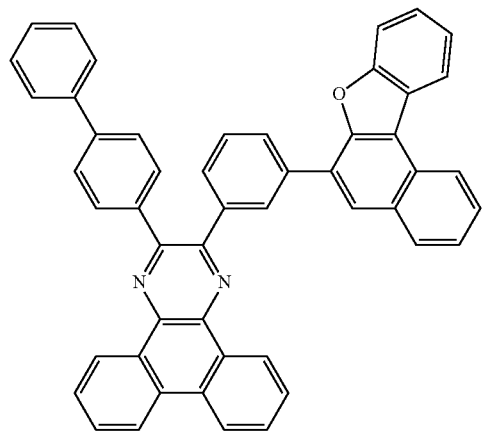 (232)
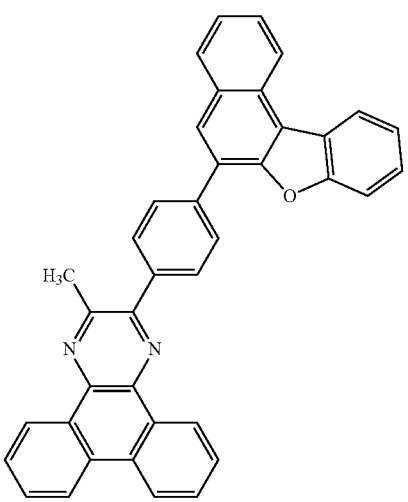 (235)

(236)
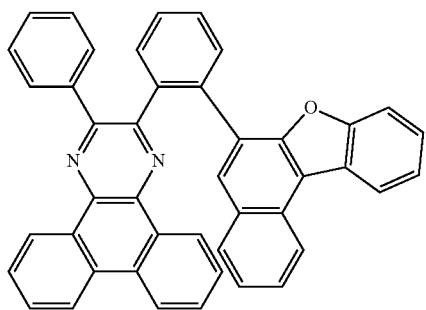
(237)
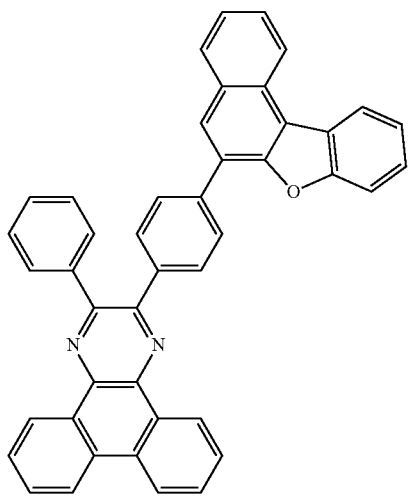
(238)
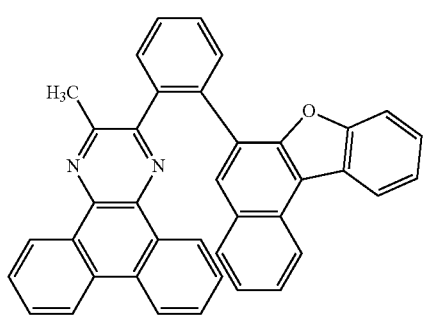
[Chemical formula 12]
(239)
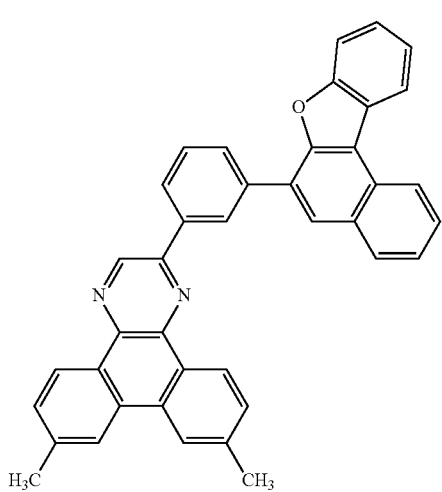
(240)
(241)
(242)

[Chemical formula 13]
(243)
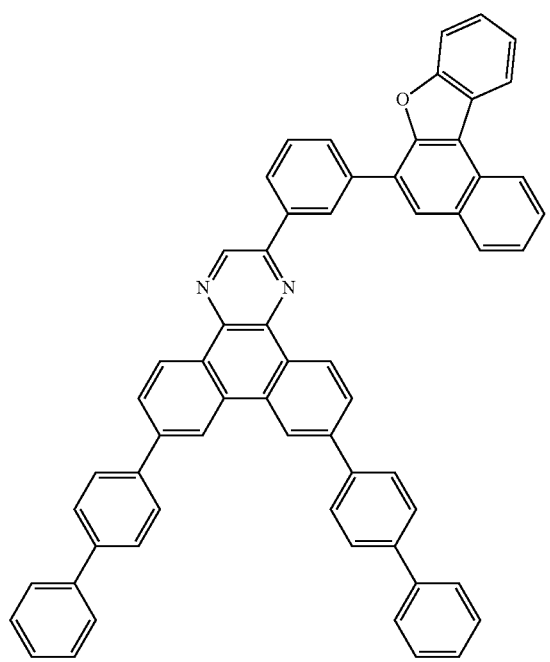
(244)
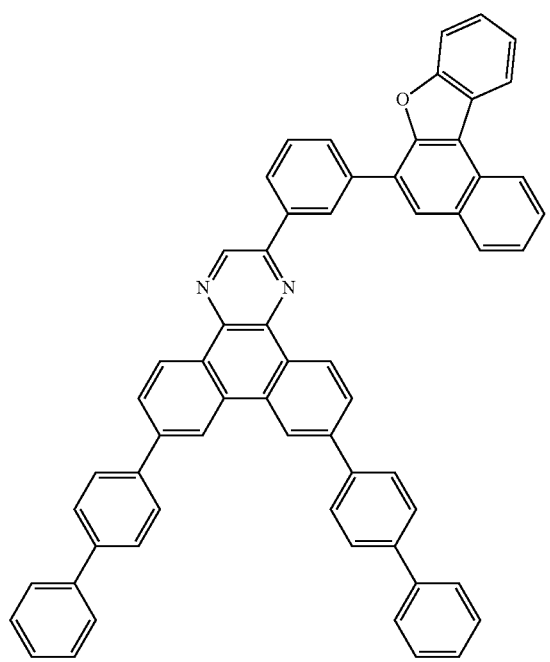
(245)
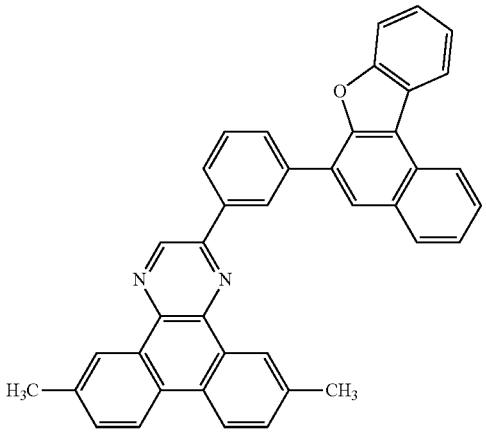
(246)
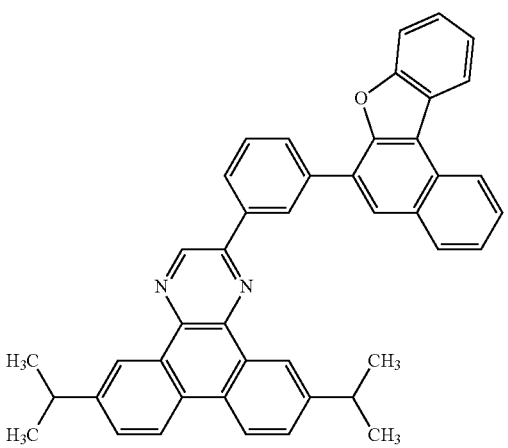
(247)
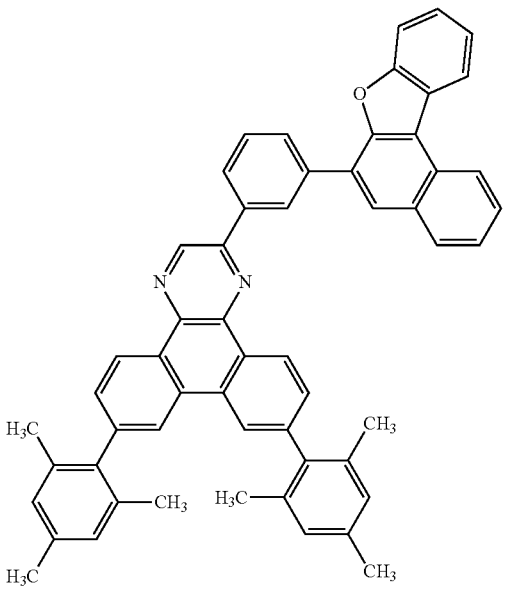

-continued
[Chemical formula 14]
(248)
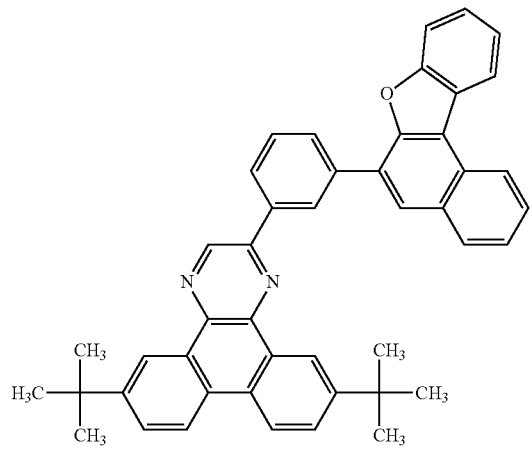
(249)
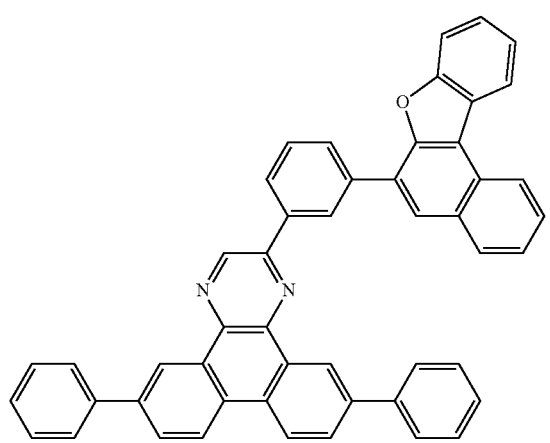
(250)
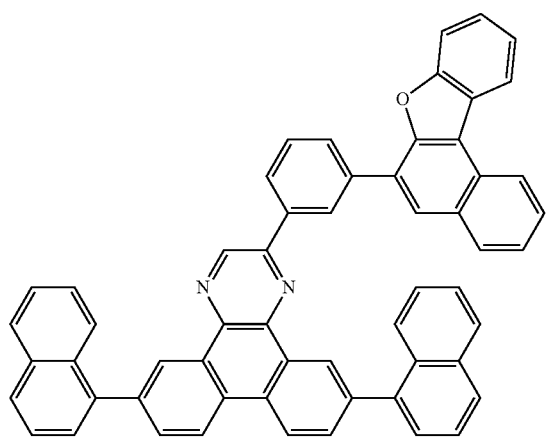
(251)
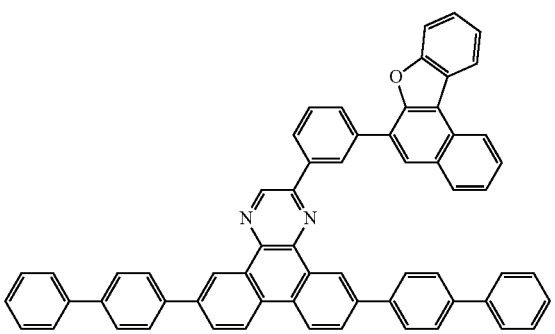
(252)
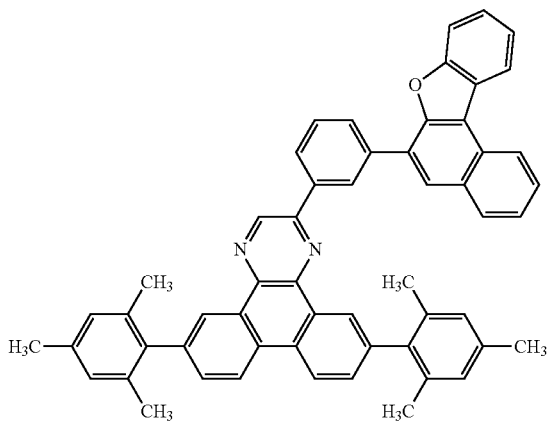
(253)
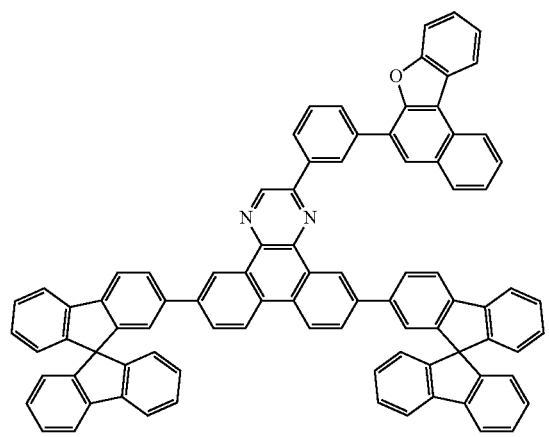

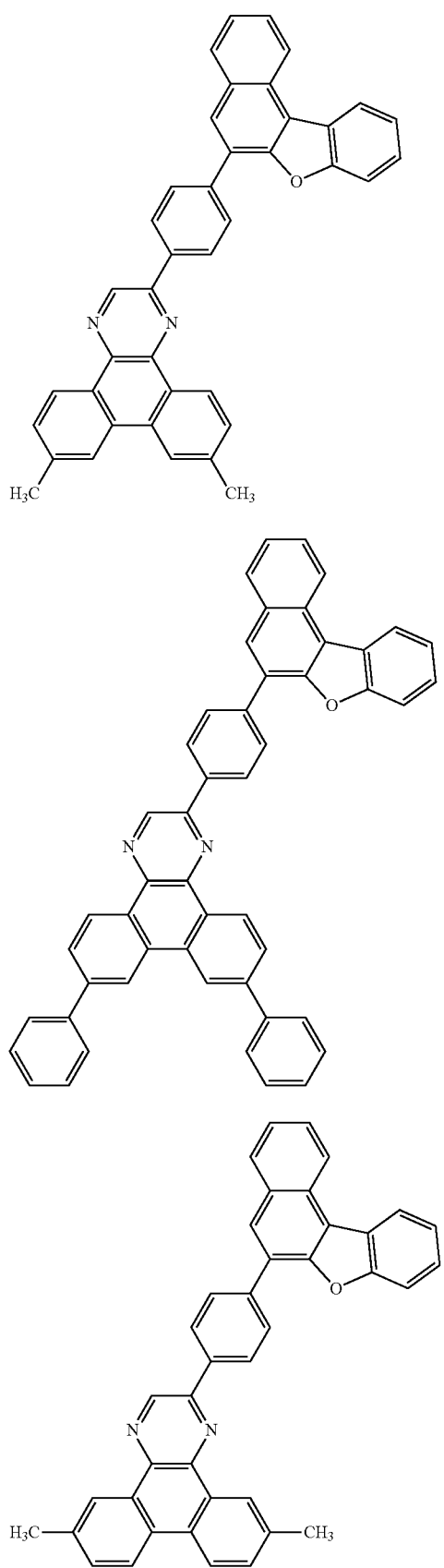
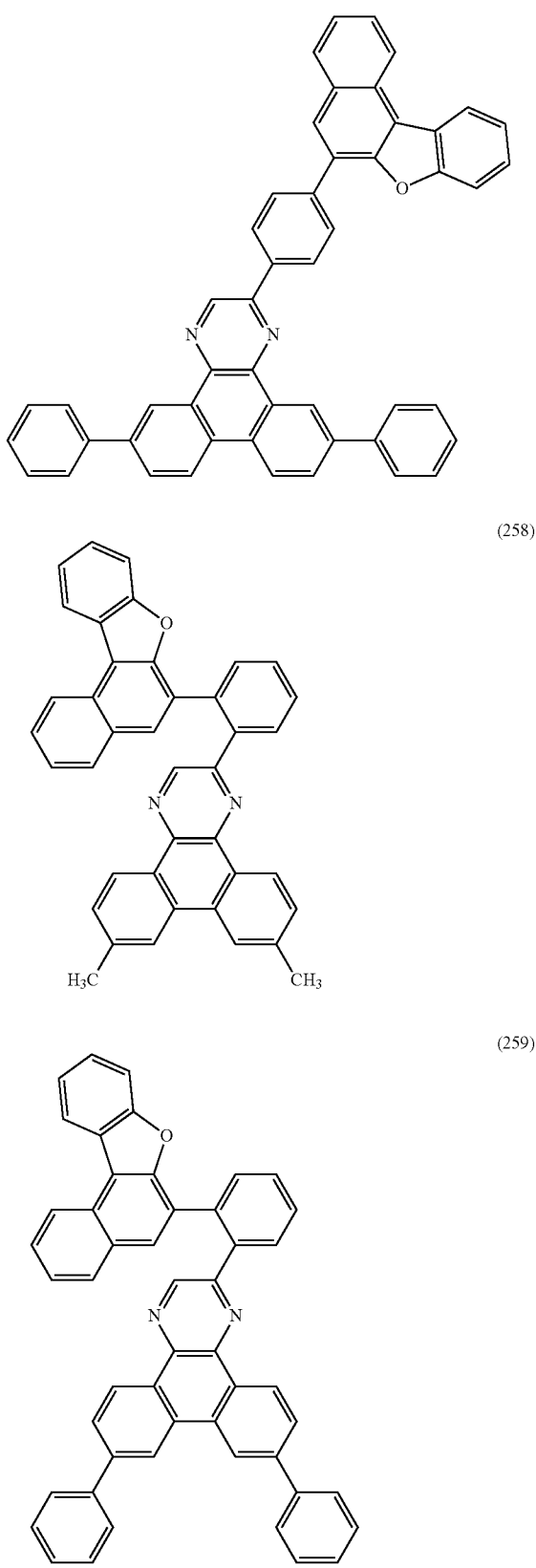

(260)
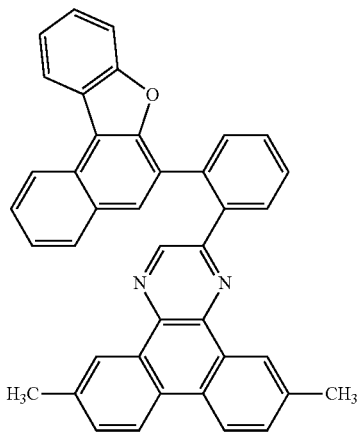
(261)
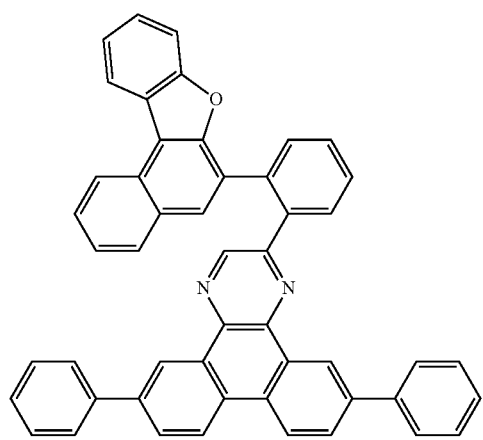
(262)
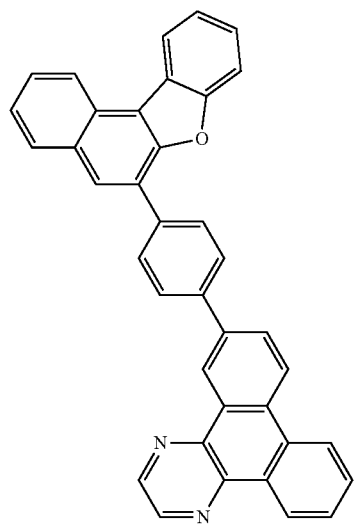
(263)
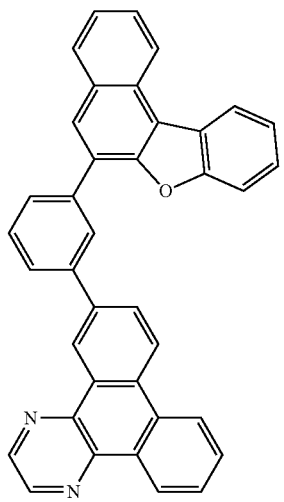
(264)
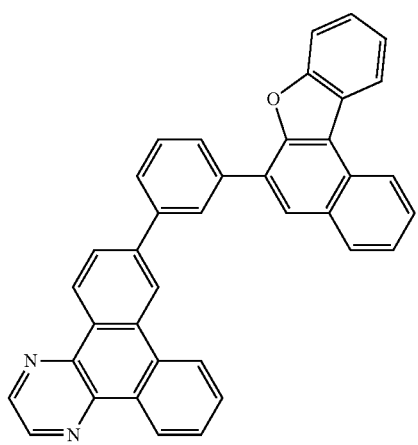
(265)

[Chemical formula 16]

(266)
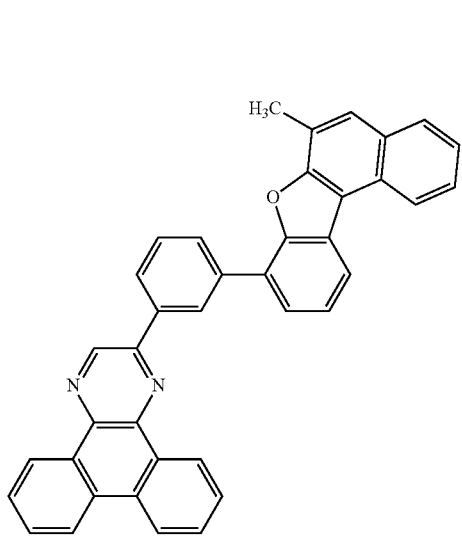

(267)
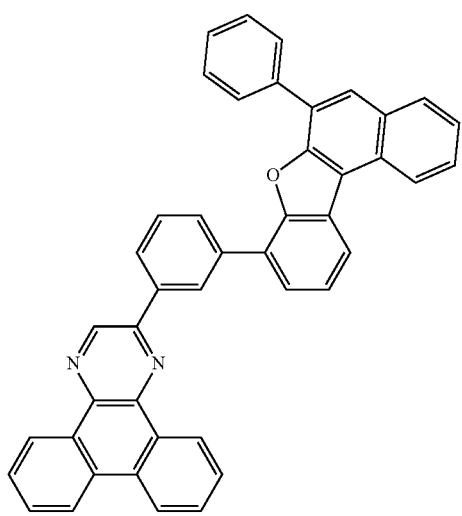

(268)

(269)
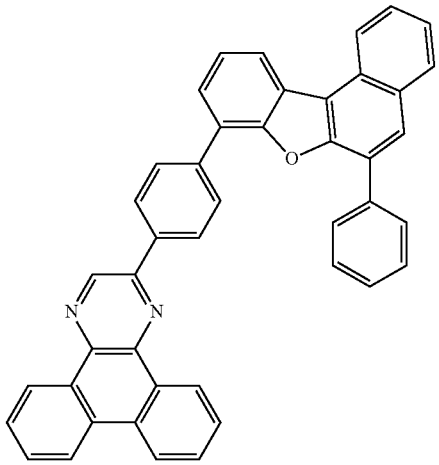

(270)
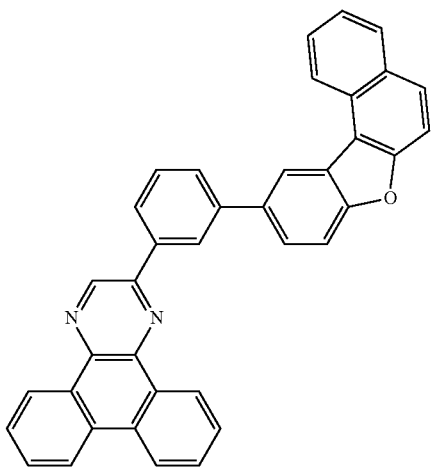

A variety of reactions can be applied to a method for synthesizing the heterocyclic compound of one embodiment of the present invention. As an example, a method for synthesizing the heterocyclic compound represented by General Formula (G0) is described below. Note that the methods for synthesizing the heterocyclic compound of one embodiment of the present invention are not limited to the synthesis methods below.

As shown in Synthesis Scheme (A-1), a halide (compound (a1)) of a dibenzo[f,h]quinoxaline derivative and an organoboron compound or a boronic acid (compound (a2)) of a benzo[b]naphtho[1,2-d]furan derivative are coupled by the Suzuki-Miyaura reaction, whereby the heterocyclic compound of one embodiment of the present invention which is represented by General Formula (G0) can be provided.

[Chemical formula 17]

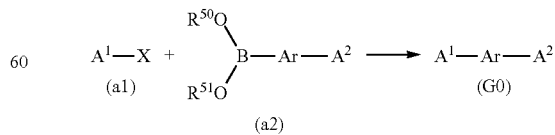

In Synthesis Scheme (A-1), X represents a halogen, $A^1$ represents a dibenzo[f,h]quinoxalinyl group, $A^2$ represents a benzo[b]naphtho[1,2-d]furanyl group, Ar represents an arylene group having 6 to 13 carbon atoms, $R^{50}$ and $R^{51}$ separately represent hydrogen or an alkyl group having 1 to 6 carbon atoms, and $R^{50}$ and $R^{51}$ may be bonded to each other to form a ring. The dibenzo[f,h]quinoxalinyl group, the benzo[b]naphtho[1,2-d]furanyl group, and the arylene group separately are unsubstituted or have, as a substituent, an alkyl group having 1 to 4 carbon atoms or an aryl group having 6 to 13 carbon atoms.

Examples of a palladium catalyst which can be used in Synthesis Scheme (A-1) include, but not limited to, palladium(II)acetate, tetrakis(triphenylphosphine)palladium(0), and bis(triphenylphosphine)palladium(II)dichloride.

Examples of a ligand of the palladium catalyst which can be used in Synthesis Scheme (A-1) include, but not limited to, tri(ortho-tolyl)phosphine, triphenylphosphine, and tricyclohexylphosphine.

Examples of a base which can be used in Synthesis Scheme (A-1) include, but not limited to, an organic base such as sodium tert-butoxide and an inorganic base such as potassium carbonate and sodium carbonate.

Examples of a solvent which can be used in Synthesis Scheme (A-1) include, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of water and an ether such as ethylene glycol dimethyl ether. However, the solvent that can be used is not limited to these solvents. Note that a mixed solvent of toluene and water; a mixed solvent of toluene, ethanol, and water; or a mixed solvent of water and an ether such as ethylene glycol dimethyl ether is more preferable.

As the coupling reaction illustrated in Synthesis Scheme (A-1), the Suzuki-Miyaura coupling reaction using the organoboron compound or the boronic acid represented by the compound (a2) may be replaced with a cross coupling reaction using an organoaluminum compound, an organozirconium compound, an organozinc compound, an organotin compound, or the like. However, the present invention is not limited thereto.

Further, in the Suzuki-Miyaura coupling reaction shown in Synthesis Scheme (A-1), an organoboron compound or a boronic acid of a dibenzo[f,h]quinoxaline derivative may be coupled with a halide of a benzo[b]naphtho[1,2-d]furan derivative or a benzo[b]naphtho[1,2-d]furan derivative which has a triflate group as a substituent, by the Suzuki-Miyaura reaction.

Thus, the heterocyclic compound of this embodiment can be synthesized.

In a light-emitting element, the heterocyclic compound of this embodiment can be favorably used as a host material of a light-emitting layer, in which a light-emitting substance is dispersed, or a material of an electron-transport layer. By the use of the heterocyclic compound of this embodiment, a light-emitting element with a long lifetime can be provided.

This embodiment can be freely combined with any of the other embodiments.

Embodiment 2

In this embodiment, light-emitting elements of embodiments of the present invention will be described with reference to FIGS. 1A to 1D.

A light-emitting element of one embodiment of the present invention has a layer containing a heterocyclic compound between a pair of electrodes, and the heterocyclic compound has a dibenzo[f,h]quinoxaline skeleton and a benzo[b]naphtho[1,2-d]furan skeleton.

A light-emitting element of one embodiment of the present invention has a layer containing a heterocyclic compound between a pair of electrodes, and the heterocyclic compound is a heterocyclic compound where a dibenzo[f,h]quinoxaline skeleton and a benzo[b]naphtho[1,2-d]furan skeleton are bonded through an arylene skeleton.

The heterocyclic compound included in any of the above structures is sterically bulky and highly resistant to heat. Accordingly, the use of the heterocyclic compound enables a light-emitting element to have a long lifetime.

Furthermore, the heterocyclic compound can accept electrons and holes since the heterocyclic compound has a dibenzo[f,h]quinoxaline skeleton as an electron-transport skeleton and a benzo[b]naphtho[1,2-d]furan skeleton as a hole-transport skeleton. Accordingly, by the use of the heterocyclic compound as a host material of a light-emitting layer, electrons and holes recombine in the light-emitting layer and it is possible to inhibit a reduction in lifetime of the light-emitting element. That is, a preferred embodiment of the present invention is a light-emitting element including, between a pair of electrodes, a light-emitting layer containing a light-emitting substance (guest material) and the above heterocyclic compound serving as a host material in which the light-emitting substance is dispersed.

The light-emitting element of this embodiment includes a layer (EL layer) containing a light-emitting organic compound between a pair of electrodes (a first electrode and a second electrode). One of the first electrode and the second electrode functions as an anode, and the other functions as a cathode. In this embodiment, the EL layer contains the heterocyclic compound of one embodiment of the present invention which is described in Embodiment 1.

<<Structural Example of Light-Emitting Element>>

A light-emitting element illustrated in FIG. 1A includes an EL layer 203 between a first electrode 201 and a second electrode 205. In this embodiment, the first electrode 201 serves as an anode and the second electrode 205 serves as a cathode.

When a voltage higher than the threshold voltage of the light-emitting element is applied between the first electrode 201 and the second electrode 205, holes are injected from the first electrode 201 side to the EL layer 203 and electrons are injected from the second electrode 205 side to the EL layer 203. The injected electrons and holes recombine in the EL layer 203 and a light-emitting substance contained in the EL layer 203 emits light.

The EL layer 203 includes at least a light-emitting layer 303 containing a light-emitting substance.

Further, when a plurality of light-emitting layers are provided in the EL layer and emission colors of the layers are made different, light emission of a desired color can be provided from the light-emitting element as a whole. For example, the emission colors of first and second light-emitting layers are complementary in a light-emitting element having the two light-emitting layers, so that the light-emitting element can be made to emit white light as a whole. Note that "complementary colors" refer to colors that can produce an achromatic color when mixed. That is, white light emission can be produced by mixture of light from materials whose emission colors are complementary colors. Further, the same applies to a light-emitting element having three or more light-emitting layers.

In addition to the light-emitting layer, the EL layer 203 may further include one or more layers containing any of a substance with a high hole-injection property, a substance with a high hole-transport property, a substance with a high electron-transport property, a substance with a high electron-injection property, a substance with a bipolar property (a substance with a high electron-transport property and a high hole-transport property), and the like. Either a low molecular compound or a high molecular compound can be used for the EL layer 203, and an inorganic compound may be used.

A light-emitting element illustrated in FIG. 1B includes the EL layer 203 between the first electrode 201 and the second electrode 205, and in the EL layer 203, a hole-injection layer 301, a hole-transport layer 302, the light-emitting layer 303, an electron-transport layer 304, and an electron-injection layer 305 are stacked in that order from the first electrode 201 side.

The heterocyclic compound of one embodiment of the present invention is preferably used for the light-emitting layer 303 or the electron-transport layer 304. In this embodiment, an example is described in which the heterocyclic compound of one embodiment of the present invention is used as the host material in the light-emitting layer 303.

As in light-emitting elements illustrated in FIGS. 1C and 1D, a plurality of EL layers may be stacked between the first electrode 201 and the second electrode 205. In this case, an intermediate layer 207 is preferably provided between the stacked EL layers. The intermediate layer 207 includes at least a charge-generation region.

For example, the light-emitting element illustrated in FIG. 1C includes the intermediate layer 207 between a first EL layer 203a and a second EL layer 203b. The light-emitting element illustrated in FIG. 1D includes n EL layers (n is a natural number of 2 or more), and the intermediate layers 207 between the EL layers.

The behaviors of electrons and holes in the intermediate layer 207 provided between the EL layer 203($m$) and the EL layer 203($m$+1) will be described. When a voltage higher than the threshold voltage of the light-emitting element is applied between the first electrode 201 and the second electrode 205, holes and electrons are generated in the intermediate layer 207, and the holes move into the EL layer 203($m$+1) provided on the second electrode 205 side and the electrons move into the EL layer 203($m$) provided on the first electrode 201 side. The holes injected into the EL layer 203($m$+1) recombine with electrons injected from the second electrode 205 side, so that a light-emitting substance contained in the EL layer 203($m$+1) emits light. Further, the electrons injected into the EL layer 203($m$) recombine with holes injected from the first electrode 201 side, so that a light-emitting substance contained in the EL layer 203($m$) emits light. Thus, the holes and electrons generated in the intermediate layer 207 cause light emission in different EL layers.

Note that the EL layers can be provided in contact with each other with no intermediate layer interposed therebetween when these EL layers allow the same structure as the intermediate layer to be formed therebetween. For example, when the charge-generation region is formed over one surface of an EL layer, another EL layer can be provided in contact with the surface.

Further, when emission colors of the EL layers are made different, light emission of a desired color can be provided from the light-emitting element as a whole. For example, the emission colors of first and second EL layers are complementary in a light-emitting element having the two EL layers, so that the light-emitting element can be made to emit white light as a whole. The same applies to a light-emitting element having three or more EL layers.

<<Materials of Light-Emitting Element>>

Examples of materials which can be used for each layer will be given below. Note that each layer is not limited to a single layer, and may be a stack of two or more layers.

<Anode>

The electrode serving as the anode (the first electrode 201 in this embodiment) can be formed using one or more kinds of conductive metals and alloys, conductive compounds, and the like. In particular, it is preferable to use a material with a high work function (4.0 eV or more). The examples include indium tin oxide (ITO), indium tin oxide containing silicon or silicon oxide, indium zinc oxide, indium oxide containing tungsten oxide and zinc oxide, graphene, gold, platinum, nickel, tungsten, chromium, molybdenum, iron, cobalt, copper, palladium, and a nitride of a metal material (e.g., titanium nitride).

When the anode is in contact with the charge-generation region, any of a variety of conductive materials can be used regardless of their work functions; for example, aluminum, silver, an alloy containing aluminum, or the like can be used.

<Cathode>

The electrode serving as the cathode (the second electrode 205 in this embodiment) can be formed using one or more kinds of conductive metals and alloys, conductive compounds, and the like. In particular, it is preferable to use a material with a low work function (3.8 eV or less). The examples include aluminum, silver, an element belonging to Group 1 or 2 of the periodic table (e.g., an alkali metal such as lithium or cesium, an alkaline earth metal such as calcium or strontium, or magnesium), an alloy containing any of these elements (e.g., Mg—Ag or Al—Li), a rare earth metal such as europium or ytterbium, and an alloy containing any of these rare earth metals.

Note that when the cathode is in contact with the charge-generation region, any of a variety of conductive materials can be used regardless of its work function. For example, ITO or indium tin oxide containing silicon or silicon oxide can be used.

The electrodes may be formed separately by a vacuum evaporation method or a sputtering method. Alternatively, when a silver paste or the like is used, a coating method or an inkjet method may be used.

<Light-Emitting Layer>

The light-emitting layer 303 contains a light-emitting substance. In an example described in this embodiment, the light-emitting layer 303 contains a guest material and a host material in which the guest material is dispersed and the heterocyclic compound of one embodiment of the present invention is used as the host material. The heterocyclic compound of one embodiment of the present invention can be favorably used as a host material in a light-emitting layer when a light-emitting substance is a phosphorescent compound emitting light in a wavelength range from red to yellow green or a fluorescent compound.

When the light-emitting layer has the structure in which the guest material is dispersed in the host material, the crystallization of the light-emitting layer can be inhibited. Further, it is possible to inhibit concentration quenching due to high concentration of the guest material; thus, the light-emitting element can have higher emission efficiency.

In addition to the guest material and the host material, the light-emitting layer may contain another compound. Further, in addition to the light-emitting layer containing the heterocyclic compound of one embodiment of the present invention, the light-emitting element of one embodiment of the present invention may include another light-emitting layer. In that case, a fluorescent compound, a phosphorescent compound, or a substance emitting thermally activated delayed fluorescence can be used as the light-emitting substance, and a compound to be described below which easily accepts electrons or a compound to be described below which easily accepts holes can be used as the host material.

Note that it is preferable that the level of triplet excitation energy ($T_1$ level) of the host material (or a material other than the guest material in the light-emitting layer) be higher than the $T_1$ level of the guest material. This is because, when the $T_1$ level of the host material is lower than that of the guest material, the triplet excitation energy of the guest material, which is to contribute to light emission, is quenched by the host material and accordingly the emission efficiency is reduced.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (fluorescence spectrum in energy transfer from a singlet excited state, phosphorescence spectrum in energy transfer from a triplet excited state) have a large overlap with an absorption spectrum of a guest material (specifically, spectrum in an absorption band on the longest wavelength (lowest energy) side).

However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, because the phosphorescence spectrum of the host material is located on the longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For this reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, it is preferable that in a light-emitting layer of a light-emitting element which uses a phosphorescent compound as a guest material, a third substance be contained in addition to the phosphorescent compound and the host material (which are respectively regarded as a first substance and a second substance contained in the light-emitting layer), and a combination of the host material and the third substance form an exciplex (also referred to as excited complex). In that case, the host material and the third substance form an exciplex at the time of recombination of carriers (electrons and holes) in the light-emitting layer. Thus, in the light-emitting layer, fluorescence spectra of the host material and the third substance are converted into an emission spectrum of the exciplex which is located on a longer wavelength side. Moreover, when the host material and the third substance are selected such that the emission spectrum of the exciplex has a large overlap with the absorption spectrum of the guest material, energy transfer from a singlet excited state can be maximized. Note that also in the case of a triplet excited state, energy transfer from the exciplex, not the host material, is considered to occur. In one embodiment of the present invention to which such a structure is applied, energy transfer efficiency can be improved owing to energy transfer utilizing an overlap between an emission spectrum of an exciplex and an absorption spectrum of a phosphorescent compound; accordingly, a light-emitting element with high external quantum efficiency can be provided.

As the guest material, a phosphorescent compound to be described below can be used. Although any combination of the host material and the third substance can be used as long as an exciplex is formed, a compound which easily accepts electrons (a compound having an electron-trapping property) and a compound which easily accepts holes (a compound having a hole-trapping property) are preferably combined. The heterocyclic compound of one embodiment of the present invention is one of compounds having electron-trapping properties.

Thus, the light-emitting element of one embodiment of the present invention includes, between a pair of electrodes, a light-emitting layer containing a phosphorescent compound emitting light in a wavelength range from red to yellow green, the heterocyclic compound of one embodiment of the present invention, and a compound which easily accepts holes.

Examples of a compound which easily accepts holes and which can be used as the host material or the third substance are a π-electron rich heteroaromatic compound (e.g., a carbazole derivative or an indole derivative) and an aromatic amine compound.

Specifically, the following examples can be given: 4-phenyl-4'-(9-phenyl-9H-carbazol-3-yl)triphenylamine (abbreviation: PCBA1BP), 4,4'-di(1-naphthyl)-4"-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and the like.

The following examples can also be given: aromatic amine compounds such as 4,4'-bis[N-(1-naphthyl)-N-phenylamino] biphenyl (abbreviation: NPB or α-NPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4,4',4''-tris(N-carbazolyl)triphenylamine (abbreviation: TCTA), 4-phenyl-4'-(9-phenylfluoren-9-yl)triphenylamine (abbreviation: BPAFLP), and 4,4'-bis[N-(9,9-dimethylfluoren-2-yl)-N-phenylamino]biphenyl (abbreviation: DFLDPBi); and carbazole derivatives such as 4,4'-di(N-carbazolyl)biphenyl (abbreviation: CBP), 9-[4-(10-phenyl-9-anthracenyl)phenyl]-9H-carbazole (abbreviation: CzPA), and 9-phenyl-3-[4-(10-phenyl-9-anthryl)phenyl]-9H-carbazole (abbreviation: PCzPA). In addition, high molecular compounds such as poly (N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), and poly[N,N'-bis(4-butylphenyl)-N,N'-bis(phenyl)benzidine] (abbreviation: Poly-TPD) can be given.

Examples of the compound which easily accepts electrons and which can be used as the host material or the third substance include the heterocyclic compound of one embodiment of the present invention, a π-electron deficient heteroaromatic compound such as a nitrogen-containing heteroaromatic compound, a metal complex having a quinoline skeleton or a benzoquinoline skeleton, and a metal complex having an oxazole-based ligand or a thiazole-based ligand.

Specific examples include the following: metal complexes such as bis(10-hydroxybenzo[h]quinolinato)berylium (abbreviation: BeBq$_2$), bis(2-methyl-8-quinolinolato) (4-phenylphenolato)aluminum (abbreviation: BAlq), bis(8-quinolinolato)zinc(II) (abbreviation: Znq), bis[2-(2-hydroxyphenyl) benzoxazolato]zinc (abbreviation: Zn(BOX)$_2$), and bis[2-(2-hydroxyphenyl)benzothiazolato]zinc (abbreviation: Zn(BTZ)$_2$); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having quinoxaline skeletons or dibenzoquinoxaline skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl) phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), and 2-[3'-(9H-carbazol-9-yl)biphenyl-3-yl]dibenzo[f,h]quinoxaline (abbreviation: 2mCzBPDBq); heterocyclic compounds having diazine skeletons (pyrimidine skeletons or pyrazine skeletons), such as 4,6-bis[3-(phenanthren-9-yl)phenyl]pyrimidine (abbreviation: 4,6mPnP2Pm), 4,6-bis[3-(9H-carbazol-9-yl)phenyl] pyrimidine (abbreviation: 4,6mCzP2Pm), and 4,6-bis[3-(4-dibenzothienyl)phenyl]pyrimidine (abbreviation: 4,6mDBTP2Pm-II); heterocyclic compounds having pyridine skeletons, such as 3,5-bis[3-(9H-carbazol-9-yl)phenyl] pyridine (abbreviation: 3,5 DCzPPy), 1,3,5-tri[3-(3-pyridyl) phenyl]benzene (abbreviation: TmPyPB), and 3,3',5,5'-tetra [(m-pyridyl)-phen-3-yl]biphenyl (abbreviation: BP4mPy). Among the above materials, heterocyclic compounds having quinoxaline skeletons or dibenzoquinoxaline skeletons, heterocyclic compounds having diazine skeletons, and heterocyclic compounds having pyridine skeletons are preferable because of their high reliability.

The following examples can also be given: metal complexes having quinoline skeletons or benzoquinoline skeletons, such as tris(8-quinolinolato)aluminum (abbreviation: Alq) and tris(4-methyl-8-quinolinolato)aluminum (abbreviation: Almq$_3$); and heteroaromatic compounds such as bathophenanthroline (abbreviation: BPhen), bathocuproine (abbreviation: BCP), 3-(4-tert-butylphenyl)-4-(4-ethylphenyl)-5-(4-biphenylyl)-1,2,4-triazole (abbreviation: p-EtTAZ), and 4,4'-bis(5-methylbenzoxazol-2-yl)stilbene (abbreviation: BzOs). In addition, high molecular compounds such as poly (2,5-pyridinediyl) (abbreviation: PPy), poly[(9,9-dihexylfluorene-2,7-diyl)-co-(pyridine-3,5-diyl)] (abbreviation: PF-Py) and poly[(9,9-dioctylfluorene-2,7-diyl)-co-(2,2'-bipyridine-6,6'-diyl)] (abbreviation: PF-BPy) can also be given.

The materials which can be used as the host material or the third substance are not limited to the above materials as long as a combination of the material used as the host material and the material used as the third substance can form an exciplex, an emission spectrum of the exciplex overlaps with an absorption spectrum of the guest material, and a peak of the emission spectrum of the exciplex is located on a longer wavelength side than a peak of the absorption spectrum of the guest material.

Note that when a compound which easily accepts electrons and a compound which easily accepts holes are used for the host material and the third substance, carrier balance can be controlled by the mixture ratio of the compounds. Specifically, the ratio of the host material to the third substance is preferably from 1:9 to 9:1.

Further, the exciplex may be formed at the interface between two layers. For example, when a layer containing the compound which easily accepts electrons and a layer containing the compound which easily accepts holes are stacked, the exciplex is formed in the vicinity of the interface thereof. These two layers may be used as the light-emitting layer in the light-emitting element of one embodiment of the present invention. In that case, the phosphorescent compound may be added to the vicinity of the interface. The phosphorescent compound may be added to one of the two layers or both.

<<Guest Material>>

Examples of fluorescent compounds that can be used for the light-emitting layer 303 are given. Examples of materials that emit blue light are as follows: N,N'-bis[4-(9H-carbazol-9-yl)phenyl]-N,N'-diphenylstilbene-4,4'-diamine (abbreviation: YGA2 S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl) triphenylamine (abbreviation: PCBAPA). Examples of materials that emit green light are as follows: N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N, 9-diphenyl-9H-carbazol-3-amine (abbreviation: 2P CABPhA), N-(9,10-diphenyl-2-anthryl)-N,N',N'-triphenyl-1,4-phenylenediamine (abbreviation: 2DPAPA), N-[9,10-bis (1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA). Examples of materials that emit yellow light are as follows: rubrene and 5,12-bis(1,1'-biphenyl-4-yl)-6,11-diphenyltetracene (abbreviation: BPT). Examples of materials that emit red light are as follows: N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-α]fluoranthene-3,10-diamine (abbreviation: p-mPhAFD).

Examples of phosphorescent compounds that can be used for the light-emitting layer 303 are given. For example, a phosphorescent compound having an emission peak at 440 nm to 520 nm is given, examples of which include organometallic iridium complexes having 4H-triazole skeletons, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenylyl)-5-isopropyl-3-phenyl-4H-1,2,4-triazolato]iridium(III) (abbreviation: [Ir(iPrptz-3b)$_3$]); organometallic iridium complexes having 1H-triazole skeletons, such as tris[3-methyl-1-(2-methylphenyl)-5-phenyl-1H-1,2,4-triazolato]iridium(III) (abbreviation: [Ir(Mptzl-mp)$_3$]) and tris(1-methyl-5-phenyl-3-propyl-1H-1,2,4-triazolato)iridium(III) (abbreviation: [Ir(Prptzl-Me)$_3$]); organometallic iridium complexes having imidazole skeletons, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic iridium complexes in which a phenylpyridine derivative having an electron-withdrawing group is a ligand, such as bis[2-(4',6'-difluorophenyl)pyridinato-N,C$^{2'}$]iridium(III)tetrakis(1-pyrazolyl)borate (abbreviation: FIr6), bis[2-(4',6'-difluorophenyl)pyridinato-N,C$^{2'}$]iridium(III)picolinate (abbreviation: FIrpic), bis{2-[3',5'-bis(trifluoromethyl)phenyl]pyridinato-N,C$^{2'}$}iridium(III)picolinate (abbreviation: [Ir(CF$_3$ppy)$_2$(pic)]), and bis[2-(4',6'-difluorophenyl)pyridinato-N,C$^{2'}$]iridium(III)acetylacetonate (abbreviation: FIracac). Among the materials given above, the organometallic iridium complexes having 4H-triazole skeletons have high reliability and high emission efficiency and are thus especially preferable.

Examples of the phosphorescent compound having an emission peak at 520 nm to 600 nm include organometallic iridium complexes having pyrimidine skeletons, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[4-(2-norbornyl)-6-phenylpyrimidinato]iridium(III) (endo- and exo-mixture) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having pyrazine skeletons, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having pyridine skeletons, such as tris(2-phenylpyridinato-N,C$^{2'}$)iridium(III) (abbreviation: [Ir(ppy)$_3$]), bis(2-phenylpyridinato-N,C$^{2'}$)iridium(III)acetylacetonate (abbreviation: [Ir(ppy)$_2$(acac)]), bis(benzo[h]quinolinato)iridium(III)acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III)acetylacetonate (abbreviation: [Ir(pq)$_2$(acac)]); and a rare earth metal complex such as tris(acetylacetonato)(monophenanthroline)terbium(III) (abbreviation: [Tb(acac)$_3$(Phen)]). Among the above materials, the organometallic iridium complexes having pyrimidine skeletons are particularly preferable because of their distinctively high reliability and emission efficiency.

Examples of the phosphorescent compound having an emission peak at 600 nm to 700 nm include organometallic iridium complexes having pyrimidine skeletons, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(d1npm)$_2$(dpm)]); organometallic iridium complexes having pyrazine skeletons, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having pyridine skeletons, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III)acetylacetonate (abbreviation: [Ir(piq)$_2$(acac)]); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). Among the materials given above, the organometallic iridium complexes having pyrimidine skeletons have distinctively high reliability and emission efficiency and are thus especially preferable. Furthermore, the organometallic iridium complexes having pyrazine skeletons can provide red light emission with favorable chromaticity.

Alternatively, a high molecular compound can be used for the light-emitting layer 303. Examples of the materials that emit blue light include poly(9,9-dioctylfluorene-2,7-diyl) (abbreviation: POF), poly[(9,9-dioctylfluorene-2,7-diyl-co-(2,5-dimethoxybenzene-1,4-diyl)] (abbreviation: PF-DMOP), and poly{(9,9-dioctylfluorene-2,7-diyl)-co-[N,N'-di-(p-butylphenyl)-1,4-diaminobenzene]} (abbreviation: TAB-PFH). Examples of the materials that emit green light include poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), and poly[(9,9-dioctyl-2,7-divinylenefluorenylene)-alt-co-(2-methoxy-5-(2-ethylhexyloxy)-1,4-phenylene)]. Examples of the materials that emit orange to red light include poly[2-methoxy-5-(2-ethylhexoxy)-1,4-phenylenevinylene] (abbreviation: MEH-PPV), poly(3-butylthiophene-2,5-diyl), poly{[9,9-dihexyl-2,7-bis(1-cyanovinylene)fluorenylene]-alt-co-[2,5-bis(N,N'-diphenyl amino)-1,4-phenylene]}, and poly{[2-methoxy-5-(2-ethylhexyloxy)-1,4-bis(1- cyanovinylenephenylene)]-alt-co-[2,5-bis(N,N'-diphenylamino)-1,4-phenylene]} (abbreviation: CN-PPV-DPD).

<Hole-Transport Layer>

The hole-transport layer 302 contains a substance with a high hole-transport property.

The substance with a high hole-transport property is preferably a substance with a property of transporting more holes than electrons, and is especially preferably a substance with a hole mobility of $10^{-6}$ cm$^2$/Vs or more.

For the hole-transport layer 302, it is possible to use any of the compounds which easily accept holes and are described as examples of the substance applicable to the light-emitting layer 303.

It is also possible to use an aromatic hydrocarbon compound such as 2-tert-butyl-9,10-di(2-naphthyl)anthracene (abbreviation: t-BuDNA), 9,10-di(2-naphthyl)anthracene (abbreviation: DNA), or 9,10-diphenylanthracene (abbreviation: DPAnth).

<Electron-Transport Layer>

The electron-transport layer 304 contains a substance with a high electron-transport property.

The substance with a high electron-transport property is preferably an organic compound having a property of transporting more electrons than holes, and is especially preferably a substance with an electron mobility of $10^{-6}$ cm$^2$/Vs or more.

For the electron-transport layer 304, it is possible to use any of the compounds which easily accept electrons and are described as examples of the substance applicable to the light-emitting layer 303.

<Hole-Injection Layer>

The hole-injection layer 301 contains a substance with a high hole-injection property.

Examples of the substance with a high hole-injection property include metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Alternatively, it is possible to use a phthalocyanine-based compound such as phthalocyanine (abbreviation: H$_2$Pc) or copper(II)phthalocyanine (abbreviation: CuPc).

Further alternatively, it is possible to use an aromatic amine compound which is a low molecular organic compound, such as TDATA, MTDATA, DPAB, DNTPD, 1,3,5-tris[N-(4-diphenylaminophenyl)-N-phenylamino]benzene (abbreviation: DPA3B), PCzPCA1, PCzPCA2, or PCzPCN1.

Further alternatively, it is possible to use a high molecular compound such as PVK, PVTPA, PTPDMA, or Poly-TPD, or a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS).

The hole-injection layer 301 may serve as the charge-generation region. When the hole-injection layer 301 in contact with the anode serves as the charge-generation region, any of a variety of conductive materials can be used for the anode regardless of their work functions. Materials contained in the charge-generation region will be described below.

<Electron-Injection Layer>

The electron-injection layer 305 contains a substance with a high electron-injection property.

Examples of the substance with a high electron-injection property include an alkali metal, an alkaline earth metal, a rare earth metal, and a compound thereof (e.g., an oxide thereof, a carbonate thereof, and a halide thereof), such as lithium, cesium, calcium, lithium oxide, lithium carbonate, cesium carbonate, lithium fluoride, cesium fluoride, calcium fluoride, and erbium fluoride.

The electron-injection layer 305 may serve as the charge-generation region. When the electron-injection layer 305 in contact with the cathode serves as the charge-generation region, any of a variety of conductive materials can be used for the cathode regardless of their work functions. Materials contained in the charge-generation region will be described below.

<Charge-Generation Region>

The charge-generation region may have either a structure in which an electron acceptor (acceptor) is added to an organic compound with a high hole-transport property or a structure in which an electron donor (donor) is added to an organic compound with a high electron-transport property. Alternatively, these structures may be stacked.

As examples of an organic compound with a high hole-transport property, the above materials which can be used for the hole-transport layer can be given, and as examples of an organic compound with a high electron-transport property, the above materials which can be used for the electron-transport layer can be given.

Further, as the electron acceptor, 7,7,8,8-tetracyano-2,3,5,6-tetrafluoroquinodimethane (abbreviation: F$_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable since it is stable in the air, has a low hygroscopic property, and is easy to handle.

Further, as the electron donor, it is possible to use an alkali metal, an alkaline earth metal, a rare earth metal, a metal belonging to Group 2 or Group 13 of the periodic table, or an oxide or a carbonate thereof. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

The above-described layers included in the EL layer 203 and the intermediate layer 207 can be formed separately by any of the following methods: an evaporation method (including a vacuum evaporation method), a transfer method, a printing method, an inkjet method, a coating method, and the like.

This embodiment can be freely combined with any of the other embodiments.

Embodiment 3

In this embodiment, a light-emitting device of one embodiment of the present invention will be described with reference to FIGS. 2A and 2B and FIGS. 3A to 3C. The light-emitting device of this embodiment includes the light-emitting element of one embodiment of the present invention. Since the light-emitting element has a long lifetime, a light-emitting device having high reliability can be provided.

FIG. 2A is a plan view of a light-emitting device of one embodiment of the present invention, and FIG. 2B is a cross-sectional view taken along dashed-dotted line A-B in FIG. 2A.

In the light-emitting device of this embodiment, a light-emitting element 403 is provided in a space 415 surrounded by a support substrate 401, a sealing substrate 405, and a sealing material 407. The light-emitting element 403 is an organic EL element having a bottom-emission structure; specifically, a first electrode 421 which transmits visible light is provided over the support substrate 401, an EL layer 423 is provided over the first electrode 421, and a second electrode 425 which reflects visible light is provided over the EL layer 423. The EL layer 423 contains the heterocyclic compound of one embodiment of the present invention which is described in Embodiment 1.

A first terminal 409a is electrically connected to an auxiliary wiring 417 and the first electrode 421. An insulating layer 419 is provided over the first electrode 421 in a region which overlaps with the auxiliary wiring 417. The first terminal 409a is electrically insulated from the second electrode 425 by the insulating layer 419. A second terminal 409b is electrically connected to the second electrode 425. Note that although the first electrode 421 is formed over the auxiliary wiring 417 in this embodiment, the auxiliary wiring 417 may be formed over the first electrode 421.

A light extraction structure 411a is preferably provided at the interface between the support substrate 401 and the atmosphere. When provided at the interface between the support substrate 401 and the atmosphere, the light extraction structure 411a can reduce light which cannot be extracted to the atmosphere due to total reflection, resulting in an increase in the light extraction efficiency of the light-emitting device.

In addition, a light extraction structure 411b is preferably provided at the interface between the light-emitting element 403 and the support substrate 401. When the light extraction structure 411b has unevenness, a planarization layer 413 is preferably provided between the light extraction structure 411b and the first electrode 421. Accordingly, the first electrode 421 can be a flat film, and generation of leakage current in the EL layer 423 due to the unevenness of the first electrode 421 can be prevented. Further, because of the light extraction structure 411b at the interface between the planarization layer 413 and the support substrate 401, light which cannot be extracted to the atmosphere due to total reflection can be reduced, so that the light extraction efficiency of the light-emitting device can be increased.

As a material of the light extraction structure 411a and the light extraction structure 411b, a resin can be used, for example. Alternatively, for the light extraction structure 411a and the light extraction structure 411b, a hemispherical lens, a micro lens array, a film provided with an uneven surface structure, a light diffusing film, or the like can be used. For example, the light extraction structure 411a and the light extraction structure 411b can be formed by attaching the lens or film to the support substrate 401 with an adhesive or the like which has substantially the same refractive index as the support substrate 401 or the lens or film.

The surface of the planarization layer 413 which is in contact with the first electrode 421 is flatter than the surface of the planarization layer 413 which is in contact with the light extraction structure 411b. As a material of the planarization layer 413, glass, liquid, a resin, or the like having a light-transmitting property and a high refractive index can be used.

Figure 3C:
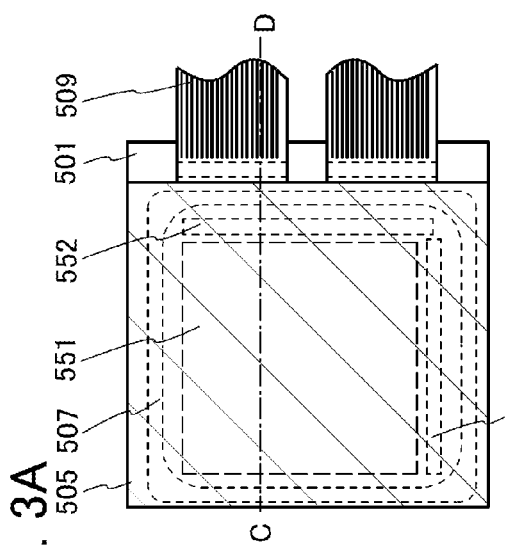
Figure 3B:
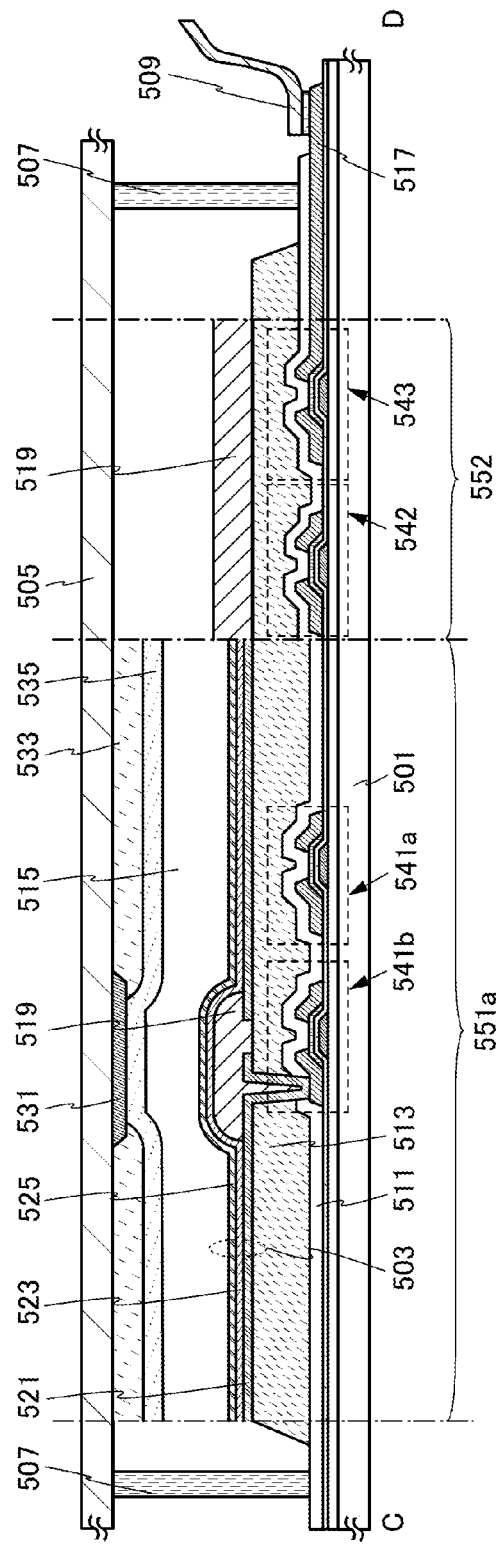

FIG. 3A is a plan view of a light-emitting device of one embodiment of the present invention, FIG. 3B is a cross-sectional view taken along dashed-dotted line C-D in FIG. 3A, and FIG. 3C is a cross-sectional view illustrating a modified example of the light-emitting portion.

An active matrix light-emitting device of this embodiment includes, over a support substrate 501, a light-emitting portion 551 (the cross section of which is illustrated in FIG. 3B and FIG. 3C as a light-emitting portion 551a and a light-emitting portion 551b, respectively), a driver circuit portion 552 (gate side driver circuit portion), a driver circuit portion 553 (source side driver circuit portion), and a sealing material 507. The light-emitting portion 551 and the driver circuit portions 552 and 553 are sealed in a space 515 surrounded by the support substrate 501, a sealing substrate 505, and the sealing material 507.

Any of a separate coloring method, a color filter method, and a color conversion method can be applied to the light-emitting device of one embodiment of the present invention. The light-emitting portion 551a fabricated by a color filter method is illustrated in FIG. 3B, and the light-emitting portion 551b fabricated by a separate coloring method is illustrated in FIG. 3C.

Each of the light-emitting portion 551a and the light-emitting portion 551b includes a plurality of light-emitting units each including a switching transistor 541a, a current control transistor 541b, and a second electrode 525 electrically connected to a wiring (a source electrode or a drain electrode) of the current control transistor 541b.

A light-emitting element 503 included in the light-emitting portion 551a has a bottom-emission structure and includes a first electrode 521 which transmits visible light, an EL layer 523, and the second electrode 525. Further, a partition 519 is formed so as to cover an end portion of the first electrode 521.

A light-emitting element 504 included in the light-emitting portion 551b has a top-emission structure and includes a first electrode 561, an EL layer 563, and the second electrode 565 which transmits visible light. Further, the partition 519 is formed so as to cover an end portion of the first electrode 561. In the EL layer 563, at least layers (e.g., light-emitting layers) which contain a variable material depending on the light-emitting element are colored separately.

Over the support substrate 501, a lead wiring 517 for connecting an external input terminal through which a signal (e.g., a video signal, a clock signal, a start signal, or a reset signal) or a potential from the outside is transmitted to the driver circuit portion 552 or 553 is provided. Here, an example is described in which a flexible printed circuit (FPC) 509 is provided as the external input terminal.

The driver circuit portions 552 and 553 include a plurality of transistors. FIG. 3B illustrates two of the transistors in the driver circuit portion 552 (transistors 542 and 543).

To prevent an increase in the number of manufacturing steps, the lead wiring 517 is preferably formed using the same material and the same step(s) as those of the electrode or the wiring in the light-emitting portion or the driver circuit portion. Described in this embodiment is an example in which the lead wiring 517 is formed using the same material and the same step(s) as those of the source electrodes and the drain electrodes of the transistors included in the light-emitting portion 551 and the driver circuit portion 552.

In FIG. 3B, the sealing material 507 is in contact with a first insulating layer 511 over the lead wiring 517. The adhesion of the sealing material 507 to metal is low in some cases. Therefore, the sealing material 507 is preferably in contact with an inorganic insulating film over the lead wiring 517. Such a structure enables a light-emitting device to have high sealing capability, high adhesion, and high reliability. Examples of the inorganic insulating film include oxide films of metals and semiconductors, nitride films of metals and semiconductors, and oxynitride films of metals and semiconductors, and specifically, a silicon oxide film, a silicon nitride film, a silicon oxynitride film, a silicon nitride oxide film, an aluminum oxide film, a titanium oxide film, and the like.

The first insulating layer 511 has an effect of preventing diffusion of impurities into a semiconductor included in the transistor. As the second insulating layer 513, an insulating film having a planarization function is preferably selected in order to reduce surface unevenness due to the transistor.

There is no particular limitation on the structure and materials of the transistor used in the light-emitting device of one embodiment of the present invention. A top-gate transistor may be used, or a bottom-gate transistor such as an inverted staggered transistor may be used. The transistor may be a channel-etched transistor or a channel-protective transistor. An n-channel transistor may be used and a p-channel transistor may also be used.

A semiconductor layer can be formed using silicon or an oxide semiconductor. Note that the transistor is preferably formed using an oxide semiconductor which is an In—Ga—Zn-based metal oxide for a semiconductor layer so as to have low off-state current, in which case an off-state leakage current of the light-emitting element can be reduced.

The sealing substrate 505 illustrated in FIG. 3B is provided with a color filter 533 as a coloring layer at a position overlapping with the light-emitting element 503 (a light-emitting region thereof), and is also provided with a black matrix 531 at a position overlapping with the partition 519. Further, an overcoat layer 535 is provided so as to cover the color filter 533 and the black matrix 531. The sealing substrate 505 illustrated in FIG. 3C is provided with a desiccant 506.

This embodiment can be combined with any of the other embodiments as appropriate.

Embodiment 4

In this embodiment, examples of electronic devices and lighting devices to which the light-emitting device of one embodiment of the present invention is applied will be described with reference to FIGS. 4A to 4E and FIGS. 5A and 5B.

Electronic devices of this embodiment each include the light-emitting device of one embodiment of the present invention in a display portion. Lighting devices of this embodiment each include the light-emitting device of one embodiment of the present invention in a light-emitting portion (a lighting portion). Highly reliable electronic devices and highly reliable lighting devices can be provided by adopting the light-emitting device of one embodiment of the present invention.

Examples of electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and lighting devices are illustrated in FIGS. 4A to 4E and FIGS. 5A and 5B.

Figure 4A:
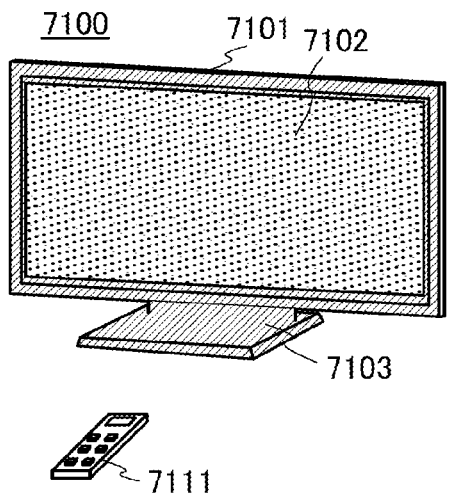
FIGS. 4A to 4E each illustrate an example of an electronic device of one embodiment of the present invention.

FIG. 4A illustrates an example of a television device. In a television device 7100, a display portion 7102 is incorporated in a housing 7101. The display portion 7102 is capable of displaying images. The light-emitting device of one embodiment of the present invention can be used for the display portion 7102. In addition, here, the housing 7101 is supported by a stand 7103.

The television device 7100 can be operated with an operation switch provided in the housing 7101 or a separate remote controller 7111. With operation keys of the remote controller 7111, channels and volume can be controlled and images displayed on the display portion 7102 can be controlled. The remote controller 7111 may be provided with a display portion for displaying data output from the remote controller 7111.

Note that the television device 7100 is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

Figure 4B:
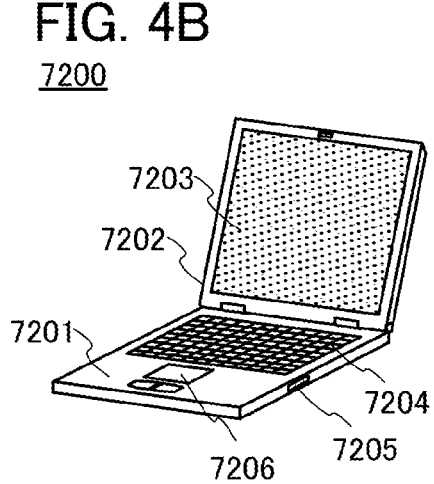

FIG. 4B illustrates an example of a computer. A computer 7200 includes a main body 7201, a housing 7202, a display portion 7203, a keyboard 7204, an external connection port 7205, a pointing device 7206, and the like. Note that this computer is manufactured by using the light-emitting device of one embodiment of the present invention for the display portion 7203.

Figure 4C:
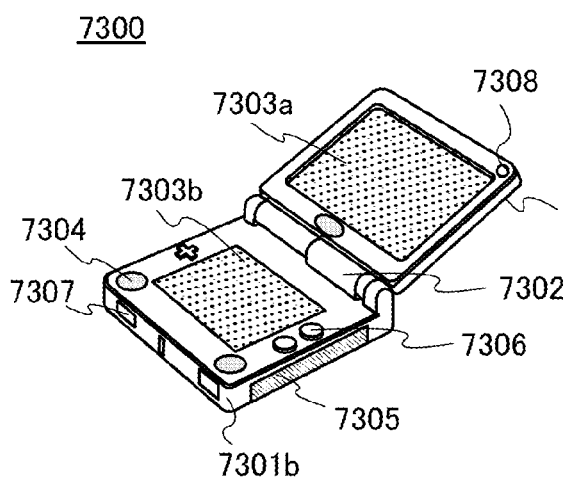

FIG. 4C illustrates an example of a portable game machine. A portable game machine 7300 has two housings, a housing 7301a and a housing 7301b, which are connected with a joint portion 7302 so that the portable game machine can be opened or closed. The housing 7301a incorporates a display portion 7303a, and the housing 7301b incorporates a display portion 7303b. In addition, the portable game machine illustrated in FIG. 4C includes a speaker portion 7304, a recording medium insertion portion 7305, an operation key 7306, a connection terminal 7307, a sensor 7308 (a sensor having a function of measuring or sensing force, displacement, position, speed, acceleration, angular velocity, rotational frequency, distance, light, liquid, magnetism, temperature, chemical substance, sound, time, hardness, electric field, electric current, voltage, electric power, radiation, flow rate, humidity, gradient, oscillation, odor, or infrared rays), an LED lamp, a microphone, and the like. It is needless to say that the structure of the portable game machine is not limited to the above structure as long as the light-emitting device of one embodiment of the present invention is used for at least either the display portion 7303a or the display portion 7303b, or both, and may include other accessories as appropriate. The portable game machine illustrated in FIG. 4C has a function of reading out a program or data stored in a recoding medium to display it on the display portion, and a function of sharing information with another portable game machine by wireless communication. Note that functions of the portable game machine illustrated in FIG. 4C are not limited to them, and the portable game machine can have various functions.

Figure 4D:
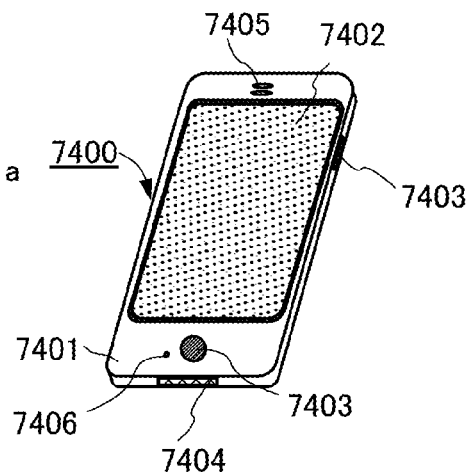

FIG. 4D illustrates an example of a cellular phone. A cellular phone 7400 is provided with a display portion 7402 incorporated in a housing 7401, an operation button 7403, an external connection port 7404, a speaker 7405, a microphone 7406, and the like. Note that the cellular phone 7400 is manufactured by using the light-emitting device of one embodiment of the present invention for the display portion 7402.

When the display portion 7402 of the cellular phone 7400 illustrated in FIG. 4D is touched with a finger or the like, data can be input into the cellular phone. Further, operations such as making a call and creating an e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on the screen can be input.

When a sensing device including a sensor such as a gyroscope sensor or an acceleration sensor for detecting inclination is provided inside the cellular phone 7400, display on the screen of the display portion 7402 can be automatically changed in direction by determining the orientation of the cellular phone 7400 (whether the cellular phone 7400 is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by the display portion 7402 while in touch with the palm or the finger, whereby personal authentication can be performed. Further, when a backlight or a sensing light source which emits near-infrared light is provided in the display portion, an image of a finger vein, a palm vein, or the like can be taken.

Figure 4E:
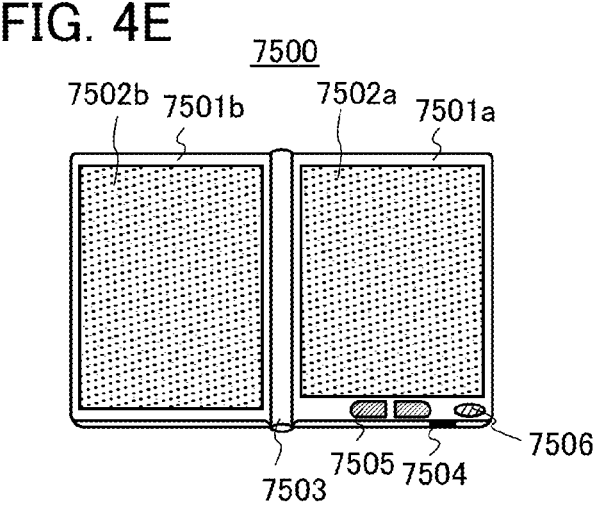

FIG. 4E illustrates an example of a foldable tablet terminal (in an open state). A tablet terminal 7500 includes a housing 7501a, a housing 7501b, a display portion 7502a, and a display portion 7502b. The housing 7501a and the housing 7501b are connected by a hinge 7503 and can be opened and closed using the hinge 7503 as an axis. The housing 7501a includes a power switch 7504, operation keys 7505, a speaker 7506, and the like. Note that the tablet terminal 7500 is manufactured by using the light-emitting device of one embodiment of the present invention for either the display portion 7502a or the display portion 7502b, or both.

Part of the display portion 7502a or the display portion 7502b can be used as a touch panel region, where data can be input by touching displayed operation keys. For example, a keyboard can be displayed on the entire region of the display portion 7502a so that the display portion 7502a is used as a touch screen, and the display portion 7502b can be used as a display screen.

Figure 5A:
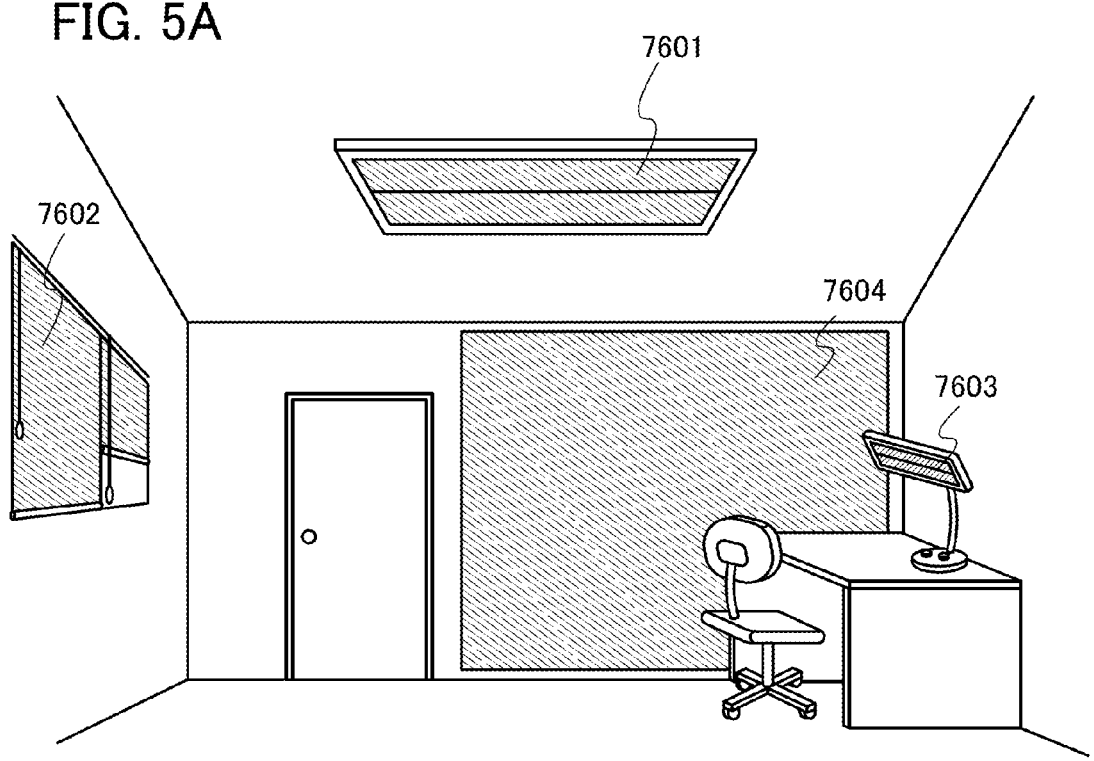
FIGS. 5A and 5B illustrate examples of lighting devices of embodiments of the present invention.

An indoor lighting device 7601, a roll-type lighting device 7602, a desk lamp 7603, and a planar lighting device 7604 illustrated in FIG. 5A are each an example of a lighting device which includes the light-emitting device of one embodiment of the present invention. Since the light-emitting device of one embodiment of the present invention can have a larger area, it can be used as a large-area lighting device. Further, since the light-emitting device is thin, the light-emitting device can be mounted on a wall.

Figure 5B:
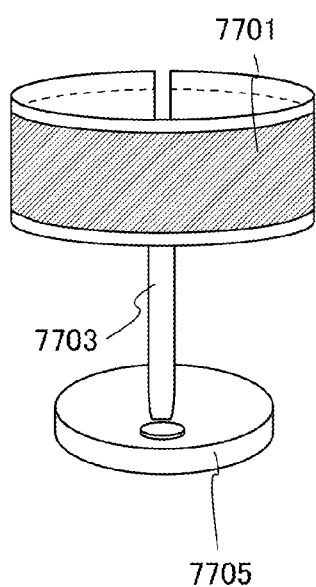

A desk lamp illustrated in FIG. 5B includes a lighting portion 7701, a support 7703, a support base 7705, and the like. The light-emitting device of one embodiment of the present invention is used for the lighting portion 7701. In one embodiment of the present invention, a lighting device whose light-emitting portion has a curved surface or a lighting device including a flexible lighting portion can be achieved. Such use of a flexible light-emitting device for a lighting device enables a place having a curved surface, such as the ceiling or dashboard of a motor vehicle, to be provided with the lighting device, as well as increases the degree of freedom in design of the lighting device.

This embodiment can be combined with any of the other embodiments as appropriate.

EXAMPLE 1

Synthesis Example 1

This example describes a method for synthesizing 2-[3-(benzo[b]naphtho[1,2-d]furan-6-yl)phenyl]dibenzo [f,h]quinoxaline (abbreviation: 2mBnfPDBq) represented by Structural Formula (201).

[Chemical formula 18]

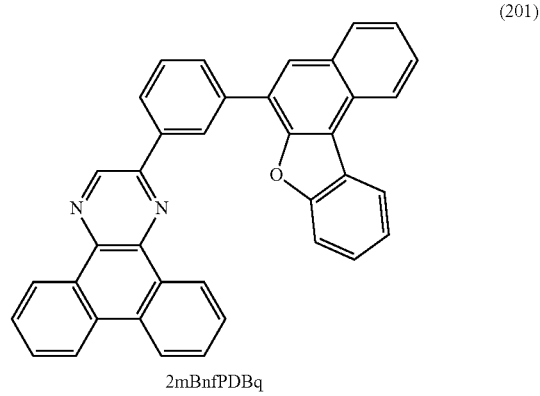

2mBnfPDBq

Synthesis Scheme (B-1) of 2mBnfPDBq is shown below.

[Chemical formula 19]

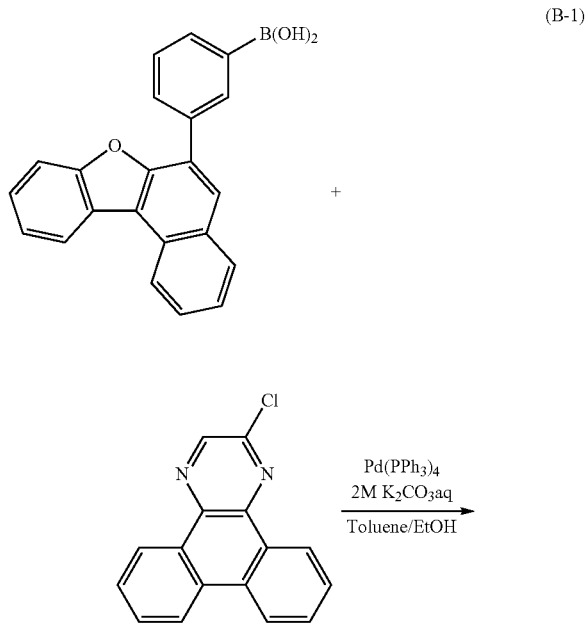

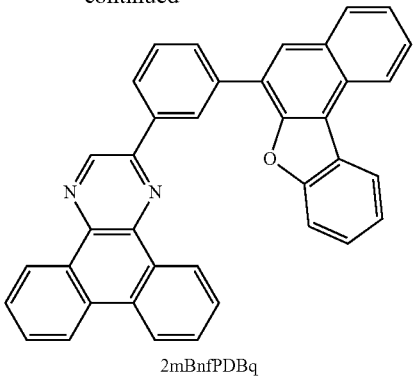

2mBnfPDBq

In a 100-mL three-neck flask were put 0.60 g (2.3 mmol) of 2-chlorodibenzo[f,h]quinoxaline, 0.80 g (2.4 mmol) of 3-(benzo[b]naphtho[1,2-d]furan-6-yl)phenylboronic acid, 25 mL of toluene, 3.0 mL of ethanol, and 4.0 mL of a 2.0 M aqueous solution of potassium carbonate. The mixture was degassed by being stirred under reduced pressure, and the air in the flask was replaced with nitrogen. To this mixture was added 80 mg (69 µmol) of tetrakis(triphenylphosphine)palladium(0). The mixture was stirred at 80° C. under a nitrogen stream for 8 hours. After the predetermined time elapsed, a solid precipitated in the flask was collected by suction filtration. This solid was added to water, and irradiation with ultrasonic waves was performed; then, a solid was collected by suction filtration. In a similar manner, this solid was added to ethanol, and irradiation with ultrasonic waves was performed; then, a solid was collected by suction filtration. A toluene solution of the resulting solid was suction-filtered through alumina and Celite (produced by Wako Pure Chemical Industries, Ltd., Catalog No. 531-16855), and the resulting filtrate was concentrated to give a solid. Further, this solid was recrystallized from toluene to give 0.90 g of a white powder in a yield of 71%.

By a train sublimation method, 0.89 g of the white powder, which was a target substance, was purified. The sublimation purification was conducted by heating of the target substance at 290° C. under a pressure of 1.9 Pa with a flow rate of argon gas of 10 mL/min for 17 hours. As a result of the sublimation purification, 0.70 g of a white powder of the target substance was provided at a collection rate of 78%.

This compound was identified as 2mBnfPDBq, which was the target substance, by nuclear magnetic resonance (NMR) spectroscopy.

$^1$H NMR data of the above substance are as follows:

$^1$H NMR (CDCl$_3$, 300 MHz): δ=7.51-7.65 (m, 3H), 7.76-7.86 (m, 7H), 8.14-8.18 (m, 2H), 8.20 (s, 1H), 8.44-8.52 (m, 2H), 8.66-8.73 (m, 3H), 9.03-9.04 (m, 1H), 9.27 (dd, J=7.5 Hz, 1.8 Hz, 1H), 9.49 (dd, J=7.8 Hz, 2.1 Hz, 1H), 9.54 (s, 1H).

Figure 6A:
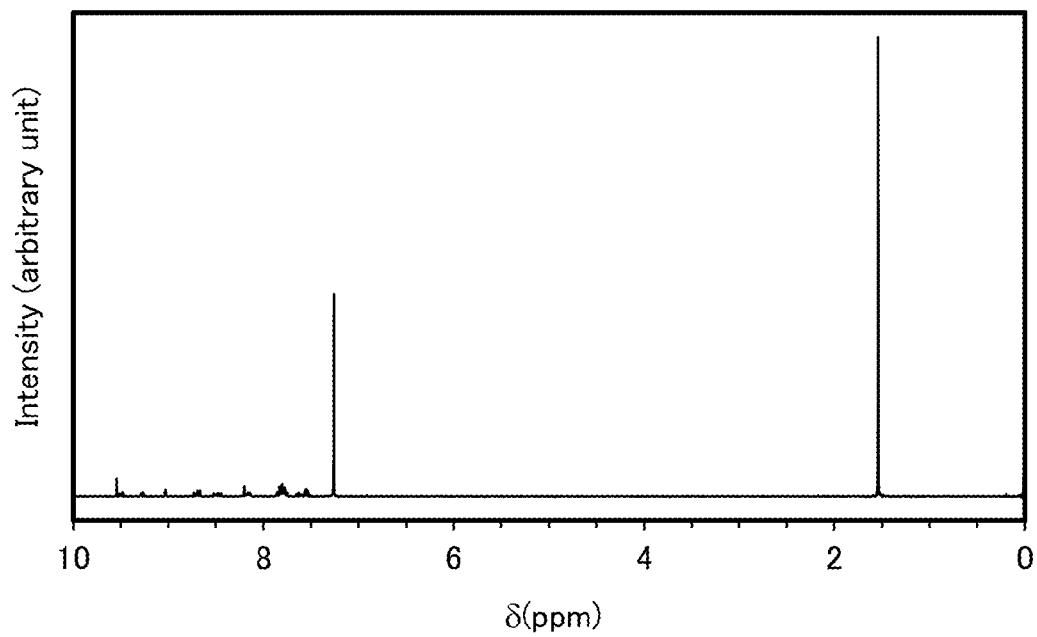
FIGS. 6A and 6B show $^1$H NMR charts of 2-[3-(benzo[b]naphtho[1,2-d]furan-6-yl)phenyl]dibenzo[f,h]quinoxaline (abbreviation: 2mBnfPDBq).
Figure 6B:
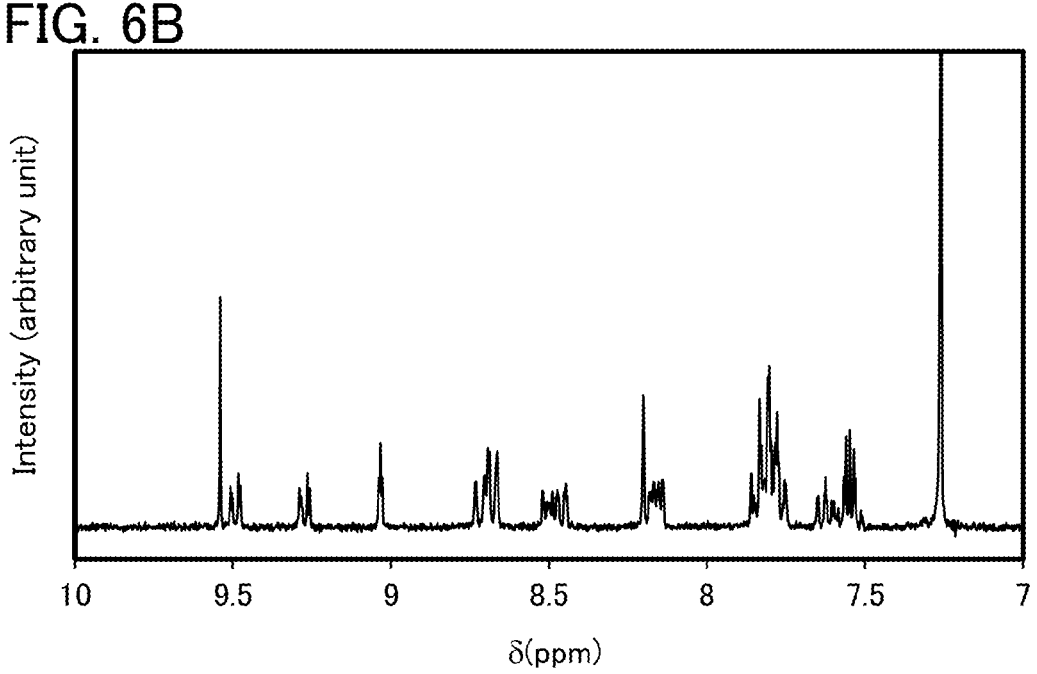

In addition, FIGS. 6A and 6B show $^1$H NMR charts. Note that FIG. 6B is a chart showing an enlarged part of FIG. 6A in the range of 7.00 ppm to 10.0 ppm.

Figure 7A:
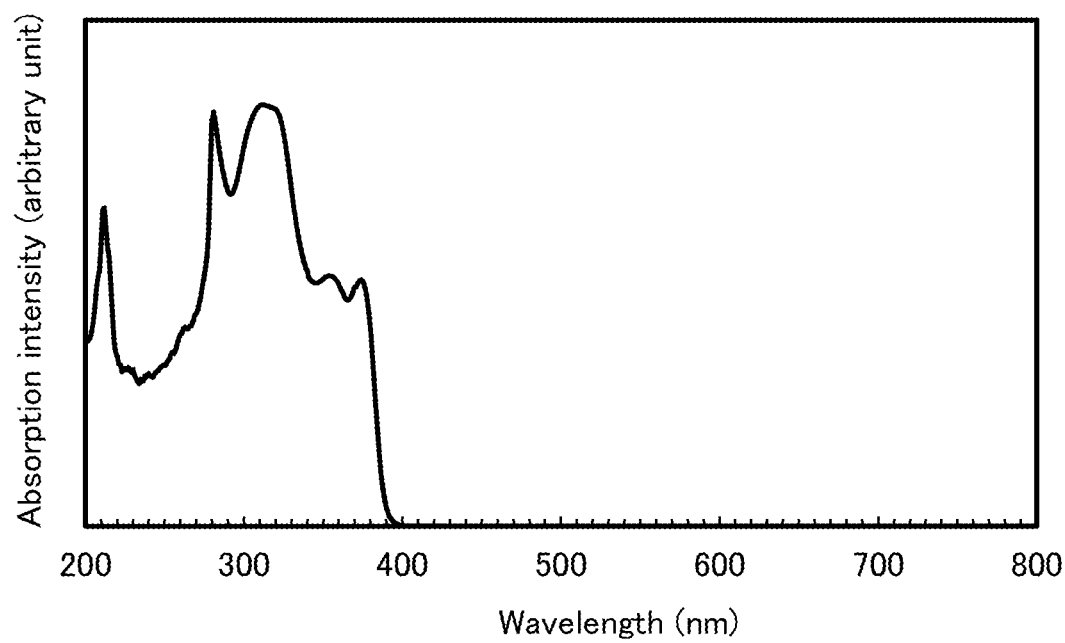
FIGS. 7A and 7B show an absorption spectrum and an emission spectrum of 2mBnfPDBq in a toluene solution of 2mBnfPDBq.
Figure 7B:
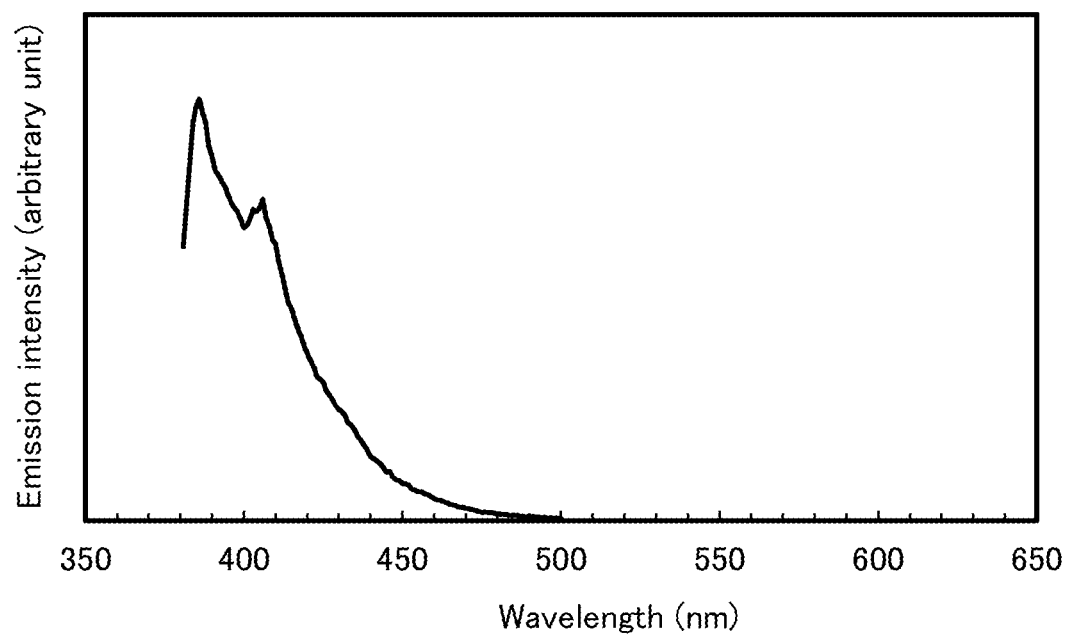
Figure 8A:
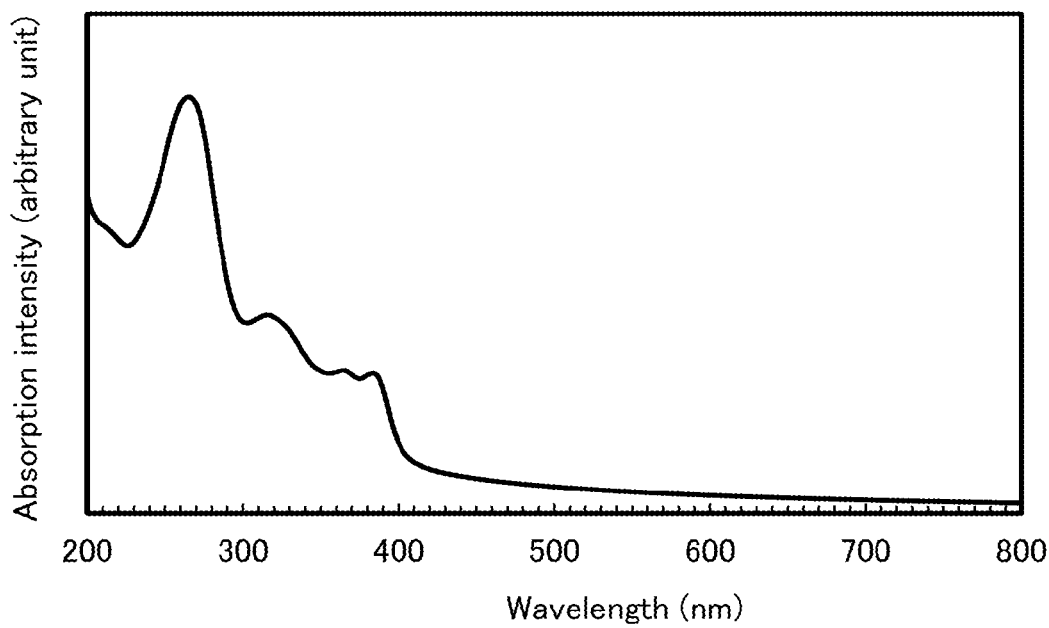
FIGS. 8A and 8B show an absorption spectrum and an emission spectrum of a thin film of 2mBnfPDBq.
Figure 8B:
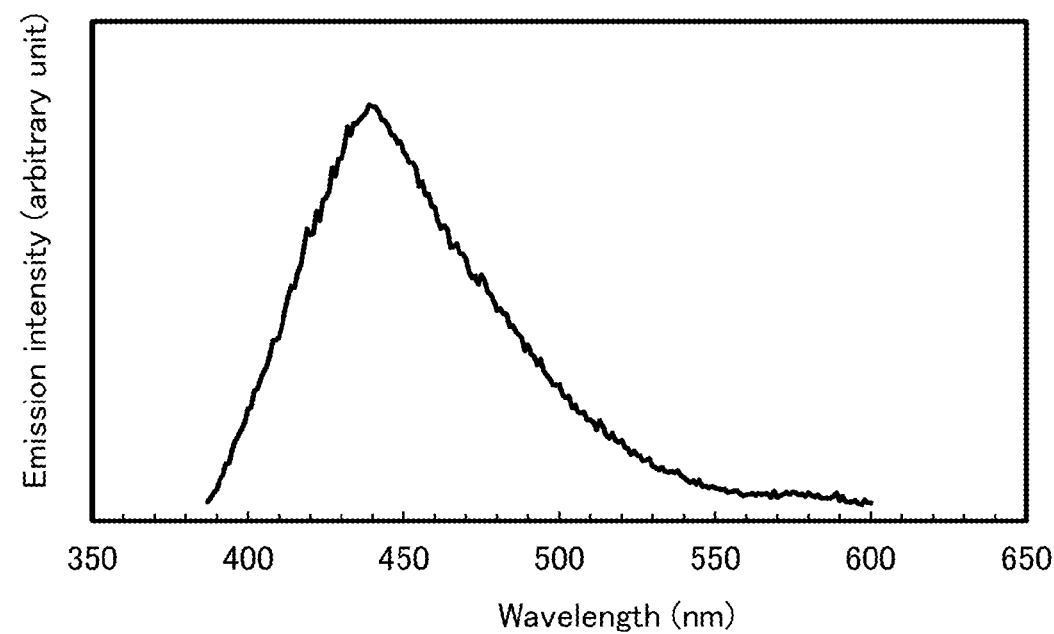

Further, FIG. 7A shows an absorption spectrum of 2mBnfPDBq in a toluene solution of 2mBnfPDBq, and FIG. 7B shows an emission spectrum thereof. FIG. 8A shows an absorption spectrum of a thin film of 2mBnfPDBq and FIG. 8B shows an emission spectrum thereof. The absorption spectrum was measured using an ultraviolet-visible spectrophotometer (V-550, produced by JASCO Corporation). The measurements were performed with samples prepared by putting the solution in a quartz cell and depositing the thin film onto a quartz substrate by evaporation. The figures show the absorption spectrum of the solution which was calculated by subtracting the absorption spectra of quartz and toluene from the absorption spectra of quartz and the solution, and the absorption spectrum of the thin film which was calculated by subtracting the absorption spectrum of a quartz substrate from the absorption spectra of the quartz substrate and the thin film. In FIGS. 7A and 7B and FIGS. 8A and 8B, the horizontal axis represents wavelength (nm) and the vertical axis represents intensity (arbitrary unit). In the case of the toluene solution, absorption peaks are observed around 353 nm and 374 nm, and emission wavelength peaks are observed at 386 nm and 406 nm (excitation wavelength: 374 nm). In the case of the thin film, absorption peaks are observed around 212 nm, 265 nm, 315 nm, 365 nm, and 383 nm, and an emission wavelength peak is observed at 440 nm (excitation wavelength: 381 nm).

Further, 2mBnfPDBq and 2-[3-(dibenzofuran-4-yl)phenyl]dibenzo[f,h]quinoxaline (abbreviation: 2mDBFPDBq-II), which is included in a comparative light-emitting element 2 in Example 2 below, were subjected to thermogravimetry-differential thermal analysis (TG-DTA). The measurement was carried out by using a high vacuum differential type differential thermal balance (TG/DTA 2410SA, produced by Bruker AXS K.K.). The measurement was carried out under a nitrogen stream (flow rate: 200 mL/min) at normal pressure at a temperature rising rate of 10° C./min. From the relationship between weight and temperature (thermogravimetry), the 5% weight loss temperature and the melting point of 2mDBFPDBq-II were 426° C. and 248° C., respectively. The 5% weight loss temperature and the melting point of 2mBnfPDBq were 454° C. and 265° C., respectively, which are higher than those of 2mDBFPDBq-II. Accordingly, it was shown that 2mBnfPDBq has higher heat resistance than 2mDBFPDBq-II.

Furthermore, 2mBnfPDBq was subjected to mass spectrometric (MS) analysis by liquid chromatography mass spectrometry (LC/MS).

The analysis by LC/MS was carried out with Acquity UPLC (produced by Waters Corporation), and Xevo G2 Tof MS (produced by Waters Corporation). In the MS analysis, ionization was carried out by an electrospray ionization (ESI) method. At this time, the capillary voltage and the sample cone voltage were set to 3.0 kV and 30 V, respectively, and detection was performed in a positive mode. A component which underwent the ionization under the above conditions was collided with an argon gas in a collision cell to dissociate into product ions. Energy (collision energy) for the collision with argon was 50 eV. A mass range for the measurement was m/z=100-1200. Measurement results are shown in FIGS. 9A and 9B.

Figure 9A:
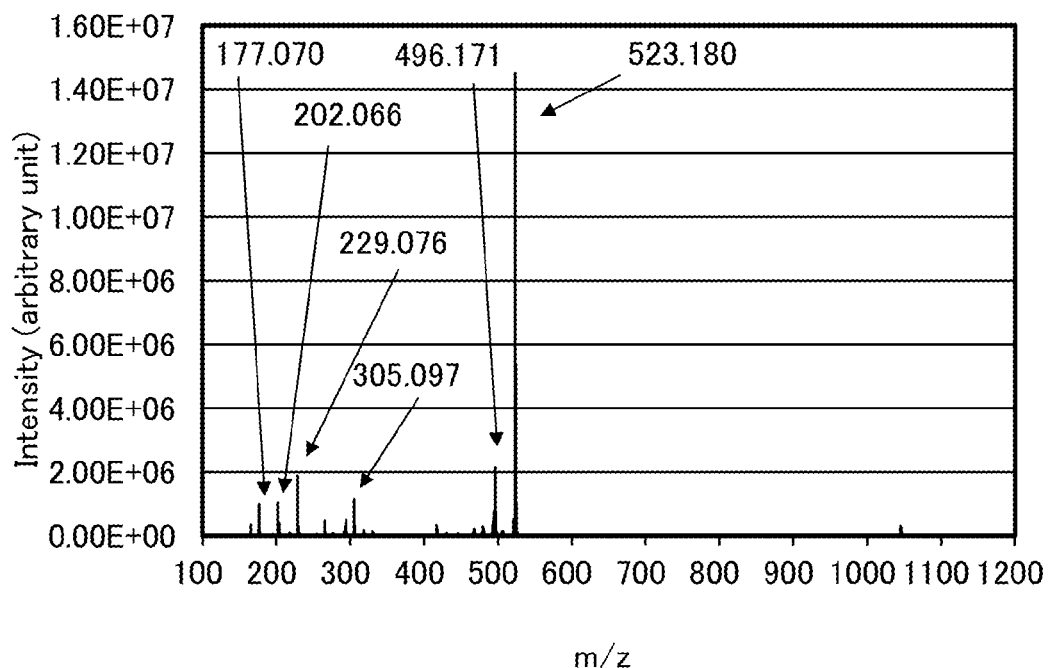
FIGS. 9A and 9B show results of LC/MS analysis of 2mBnfPDBq.
Figure 9B:
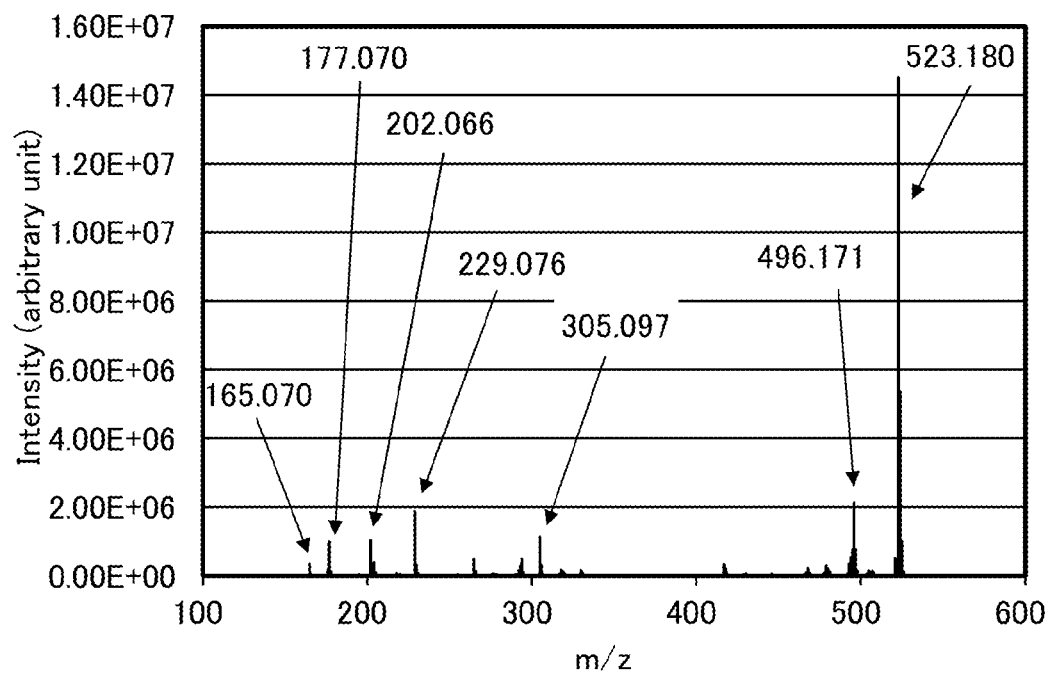

In FIGS. 9A and 9B, owing to the presence and absence of hydrogen ions and isotopes, a plurality of peaks derived from precursor ions of 2mBnfPDBq are detected mainly around m/z=523 when the collision energy is 50 eV. It was also found that owing to the presence and absence of hydrogen ions and isotopes, a plurality of peaks derived from product ions are detected mainly around each of m/z=165, m/z=177, m/z=202, m/z=229, m/z=305, and m/z=496. The results in FIGS. 9A and 9B are characteristically derived from 2mBnfPDBq and thus can be regarded as important data in identification of 2mBnfPDBq contained in a mixture.

The peaks around m/z=496 are presumed to be derived from product ions of cations in the state where one C atom and one N atom are dissociated from the dibenzo[f,h]quinoxaline ring in 2mBnfPDBq. This is one of features of the heterocyclic compound of one embodiment of the present invention. In particular, this is one of features of the heterocyclic compound of one embodiment of the present invention in which a substituent (in 2mBnfPDBq, a phenyl skeleton bonded to a benzo[b]naphtho[1,2-d]furan skeleton) is bonded to the 2-position of the dibenzo[f,h]quinoxaline ring.

The peaks around m/z=229 are presumed to be derived from product ions of cations of a diazatriphenylenyl group such as a dibenzo[f,h]quinoxaline ring. The peaks around m/z=202, m/z=177, and m/z=165 are also detected, indicating that 2mBnfPDBq, which is the heterocyclic compound of one embodiment of the present invention, includes a dibenzo[f,h]quinoxaline ring.

EXAMPLE 2

Figure 10:
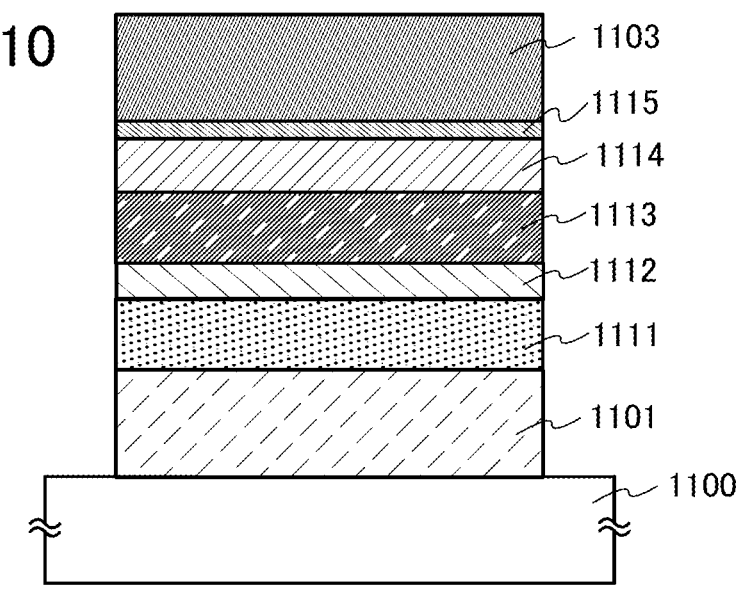
FIG. 10 illustrates a light-emitting element in examples.

In this example, the light-emitting element of one embodiment of the present invention will be described with reference to FIG. 10. Chemical formulae of materials used in this example are shown below. Note that the chemical formulae of the materials which are shown above are omitted.

[Chemical formula 20]

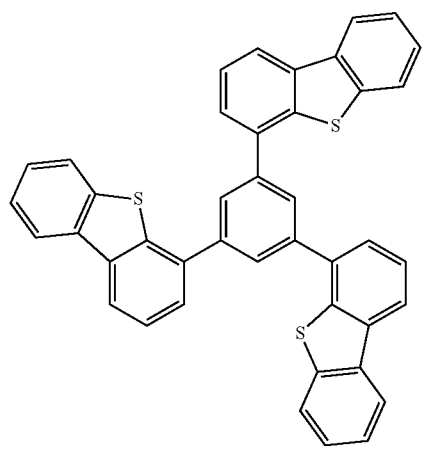

DBT3P-II

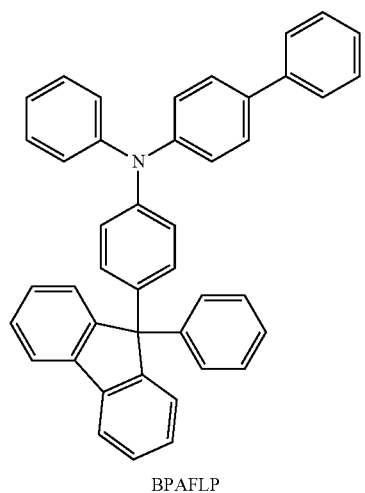

BPAFLP

-continued

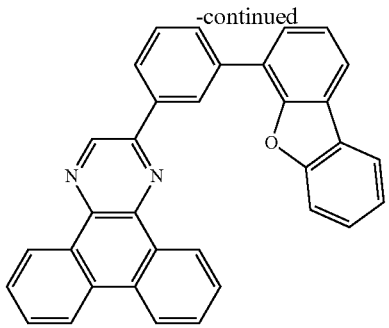

2mDBFPDBq-II

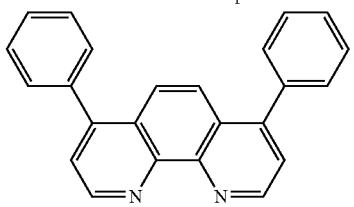

BPhen

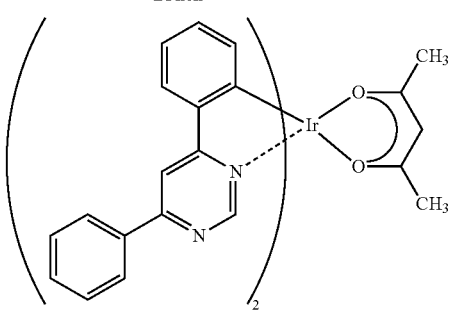

[Ir(dppm)$_2$(acac)]

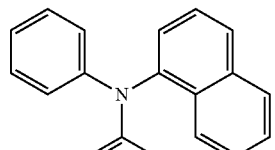

NPB

Methods for fabricating a light-emitting element 1 and the comparative light-emitting element 2 of this example will be described below.

(Light-Emitting Element 1)

A film of indium tin oxide containing silicon (ITSO) was formed over a glass substrate 1100 by a sputtering method, so that a first electrode 1101 which functions as an anode was formed. The thickness thereof was 110 nm and the electrode area was 2 mm×2 mm.

Next, as pretreatment for forming the light-emitting element over the glass substrate 1100, UV-ozone treatment was performed for 370 seconds after washing of a surface of the glass substrate 1100 with water and baking that was performed at 200° C. for 1 hour.

After that, the glass substrate 1100 was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the glass substrate 1100 was cooled down for about 30 minutes.

Then, the glass substrate 1100 over which the first electrode 1101 was formed was fixed to a substrate holder provided in the vacuum evaporation apparatus so that the surface on which the first electrode 1101 was formed faced downward. The pressure in the vacuum evaporation apparatus was reduced to about $10^{-4}$ Pa. After that, over the first electrode 1101, 4,4',4''-(1,3,5-benzenetriyl)tri(dibenzothiophene) (abbreviation: DBT3P-II) and molybdenum(VI) oxide were deposited by co-evaporation, so that a hole-injection layer 1111 was formed. The thickness of the hole-injection layer 1111 was set to 40 nm, and the weight ratio of DBT3P-II to molybdenum oxide was adjusted to 4:2 (=DBT3P-II: molybdenum oxide). Note that the co-evaporation method refers to an evaporation method in which evaporation is carried out from a plurality of evaporation sources at the same time in one treatment chamber.

Next, a film of 4-phenyl-4'-(9-phenylfluoren-9-yl)triphenylamine (abbreviation: BPAFLP) was formed to a thickness of 20 nm over the hole-injection layer 1111 to form a hole-transport layer 1112.

Further, a light-emitting layer 1113 was formed over the hole-transport layer 1112 by co-evaporation of 2mBnfPDBq, 4,4'-bis[N-(1-naphthyl)-N-phenylamino]biphenyl (abbreviation: NPB), and (acetylacetonato)bis(4,6-diphenylpyrimidinato)iridium(III) (abbreviation: [Ir(dppm)$_2$(acac)]). Here, the weight ratio of 2mBnfPDBq to NPB and [Ir(dppm)$_2$(acac)] was adjusted to 0.8:0.2:0.05 (=2mBnfPDBq: NPB: [Ir(dppm)$_2$(acac)]). The thickness of the light-emitting layer 1113 was set to 40 nm.

Then, an electron-transport layer 1114 was formed over the light-emitting layer 1113 in such a way that a 10 nm thick film of 2mBnfPDBq was formed and a 20 nm thick film of bathophenanthroline (abbreviation: BPhen) was formed.

After that, over the electron-transport layer 1114, a film of lithium fluoride (LiF) was formed by evaporation to a thickness of 1 nm to form an electron-injection layer 1115.

Lastly, aluminum was deposited by evaporation to a thickness of 200 nm to form a second electrode 1103 functioning as a cathode. Thus, the light-emitting element 1 of this example was fabricated.

Note that in all the above evaporation steps, evaporation was performed by a resistance-heating method.

(Comparative Light-Emitting Element 2)

The light-emitting layer 1113 of the comparative light-emitting element 2 was formed by co-evaporation of 2mDBFPDBq-II, NPB, and [Ir(dppm)$_2$(acac)]. Here, the weight ratio of 2mDBFPDBq-II to NPB and [Ir(dppm)$_2$(acac)] was adjusted to 0.8:0.2:0.05 (=2mDBFPDBq-II: NPB: [Ir(dppm)$_2$(acac)]). The thickness of the light-emitting layer 1113 was set to 40 nm.

The electron-transport layer 1114 of the comparative light-emitting element 2 was formed by depositing 2mDBFPDBq-II to a thickness of 10 nm and further depositing BPhen to a thickness of 20 nm. Components other than the light-emitting layer 1113 and the electron-transport layer 1114 were formed in a similar manner to the light-emitting element 1.

Table 1 shows element structures of the light-emitting elements fabricated as described above in this example.

TABLE 1

| | First Electrode | Hole-injection Layer | Hole-transport Layer | Light-emitting Layer | Electron-transport Layer | | Electron-injection Layer | Second Electrode |
|---|---|---|---|---|---|---|---|---|
| Light-emitting Element 1 | ITSO 110 nm | DBT3P-II: MoO$_x$ (=4:2) 40 nm | BPAFLP 20 nm | 2mBnfPDBq: NPB: [Ir(dppm)$_2$(acac)] (=0.8:0.2:0.05) 40 nm | 2mBnfPDBq 10 nm | BPhen 20 nm | LiF 1 nm | Al 200 nm |
| Comparative Light-emitting Element 2 | | | | 2mDBFPDBq-II: NPB: [Ir(dppm)$_2$(acac)] (=0.8:0.2:0.05) 40 nm | 2mDBFPDBq-II 10 nm | | | |

The light-emitting elements of this example were each sealed in a glove box under a nitrogen atmosphere so as not to be exposed to the air. Then, the operation characteristics of these light-emitting elements were measured. Note that the measurements were carried out at room temperature (in an atmosphere kept at 25° C.).

Figure 11:
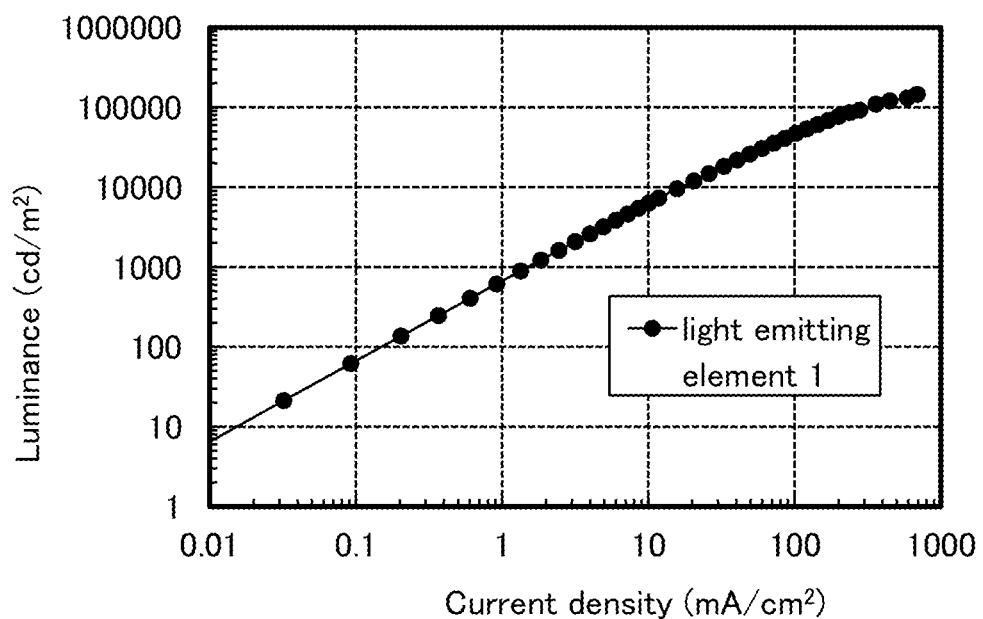
FIG. 11 shows current density-luminance characteristics of a light-emitting element in Example 2.
Figure 12:
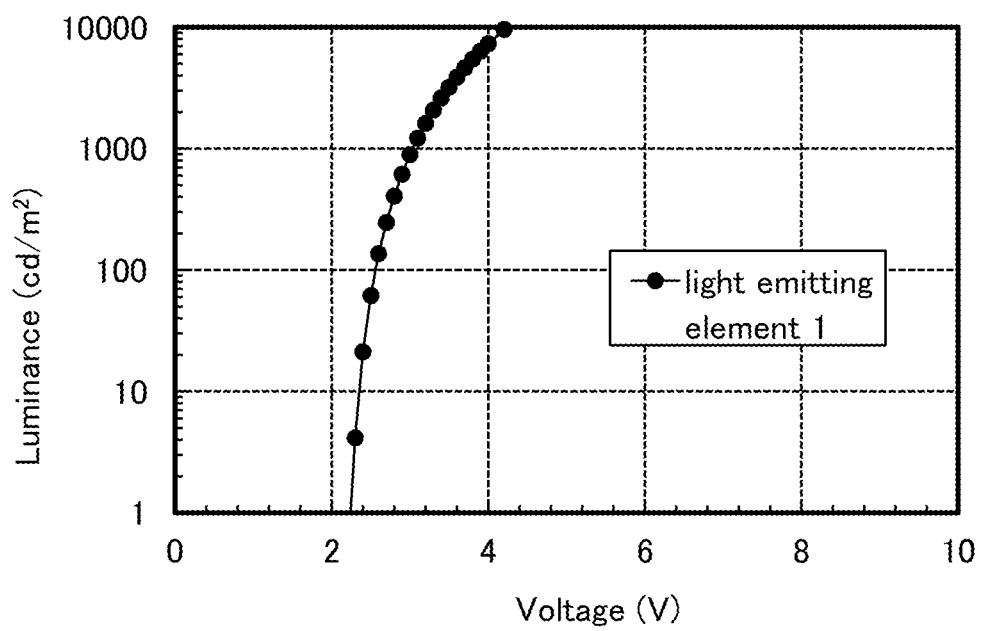
FIG. 12 shows voltage-luminance characteristics of the light-emitting element in Example 2.
Figure 13:
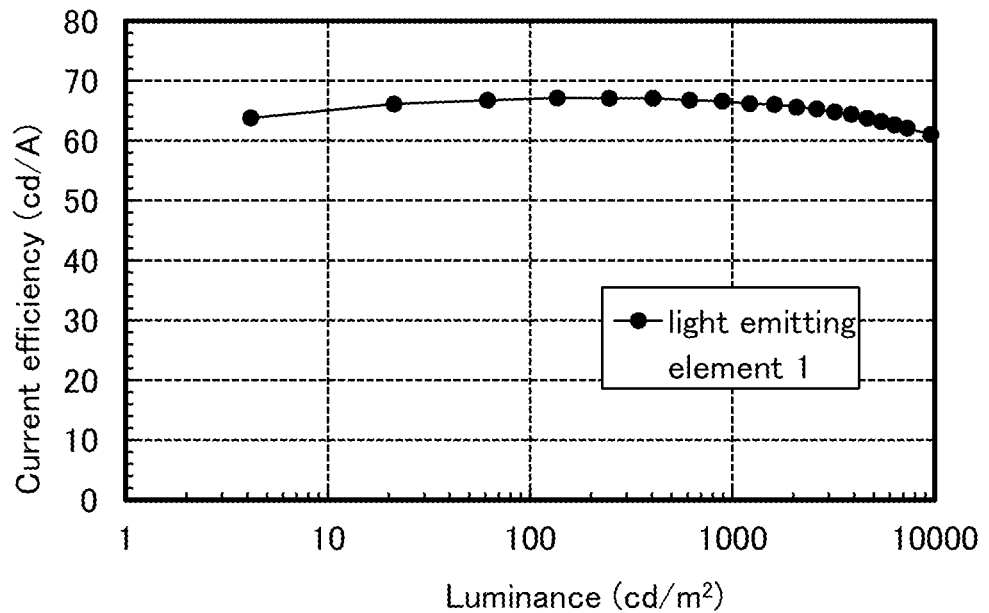
FIG. 13 shows luminance-current efficiency characteristics of the light-emitting element in Example 2.
Figure 14:
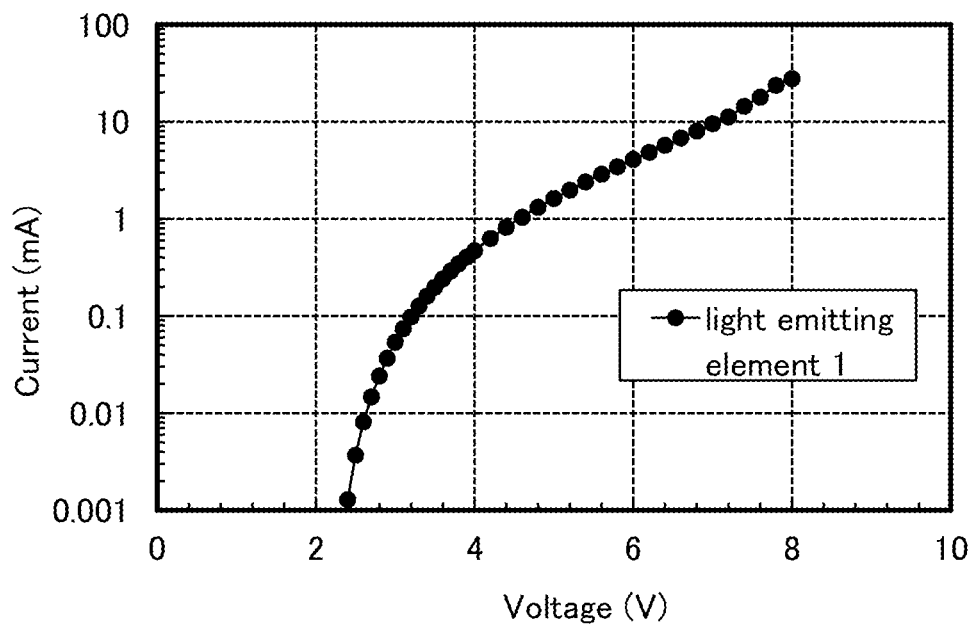
FIG. 14 shows voltage-current characteristics of the light-emitting element in Example 2.
Figure 15:
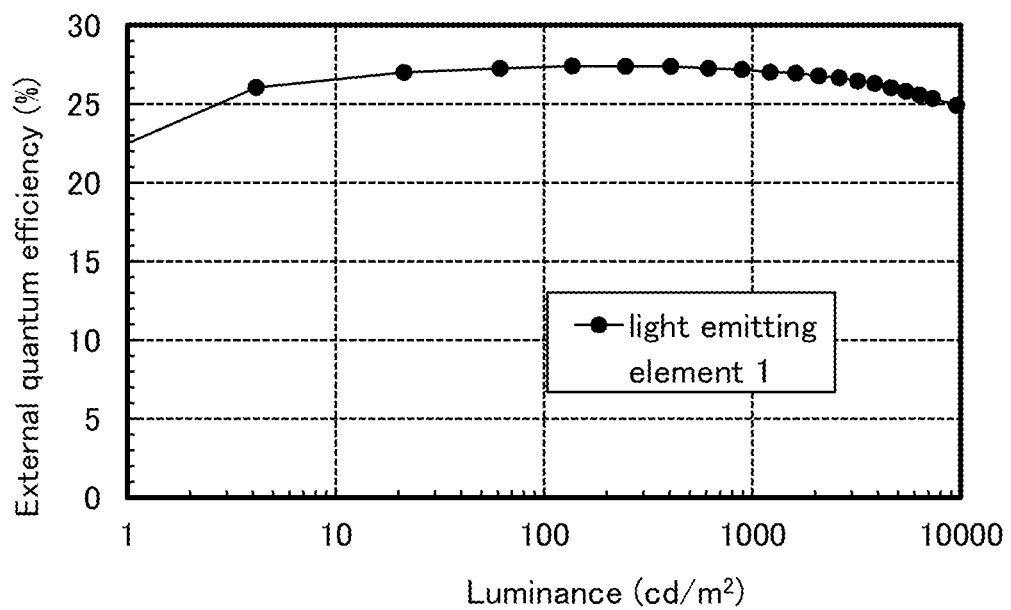
FIG. 15 shows luminance-external quantum efficiency characteristics of the light-emitting element in Example 2.

FIG. 11 shows current density-luminance characteristics of the light-emitting element 1. In FIG. 11, the horizontal axis represents current density (mA/cm$^2$), and the vertical axis represents luminance (cd/m$^2$). FIG. 12 shows voltage-luminance characteristics. In FIG. 12, the horizontal axis represents voltage (V) and the vertical axis represents luminance (cd/m$^2$). FIG. 13 shows luminance-current efficiency characteristics. In FIG. 13, the horizontal axis represents luminance (cd/m$^2$) and the vertical axis represents current efficiency (cd/A). FIG. 14 shows voltage-current characteristics. In FIG. 14, the horizontal axis represents voltage (V) and the vertical axis represents current (mA). FIG. 15 shows luminance-external quantum efficiency characteristics. In FIG. 15, the horizontal axis represents luminance (cd/m$^2$) and the vertical axis represents external quantum efficiency (%). Table 2 shows the voltage (V), current density (mA/cm$^2$), CIE chromaticity coordinates (x, y), current efficiency (cd/A), power efficiency (lm/W), and external quantum efficiency (%) of the light-emitting element 1 at a luminance of 900 cd/m$^2$.

TABLE 2

| | Voltage (V) | Current Density (mA/cm$^2$) | Chromaticity x | Chromaticity y | Luminance (cd/m$^2$) | Current Efficiency (cd/A) | Power Efficiency (lm/W) | External Quantum Efficiency (%) |
|---|---|---|---|---|---|---|---|---|
| Light-emitting Element 1 | 3.0 | 1.3 | 0.57 | 0.43 | 900 | 67 | 70 | 27 |

The CIE chromaticity coordinates (x, y) at a luminance of 900 cd/m$^2$ of the light-emitting element 1 were (0.57, 0.43) and the light-emitting element 1 exhibited orange light emission. The CIE chromaticity coordinates (x, y) at a luminance of 700 cd/m$^2$ of the comparative light-emitting element 2 were (0.56, 0.43) and the comparative light-emitting element 2 exhibited orange light emission. These results show that orange light emission originating from [Ir(dppm)$_2$(acac)] was provided from the light-emitting element 1 and the comparative light-emitting element 2.

The measurement results of the operation characteristics showed that the light-emitting element 1 has high emission efficiency and a low drive voltage.

Reliability tests of the light-emitting elements were conducted. In the reliability tests, changes in luminance over time were measured when the light-emitting elements were driven under the conditions where the initial luminance was set to 5000 cd/m$^2$ and the current density was constant. With the initial luminance taken as 100%, the length of time for the luminance to fall below 90% was 380 hours in the light-emitting element 1, which was 1.2 times as long as that (315 hours) in the comparative light-emitting element 2. Note that measurement results showed that operation characteristics of the comparative light-emitting element 2 were comparable to those of the light-emitting element 1.

This example showed that the light-emitting element of one embodiment of the present invention can have emission efficiency comparable to that of the comparative light-emitting element. In addition, it was found that the light-emitting element of one embodiment of the present invention has a longer lifetime than the comparative light-emitting element and is highly reliable.

EXAMPLE 3

In this example, the light-emitting element of one embodiment of the present invention will be described with reference to FIG. 10. Chemical formulae of materials used in this example are shown below. Note that the chemical formulae of the materials which are shown above are omitted.

[Chemical formula 21]

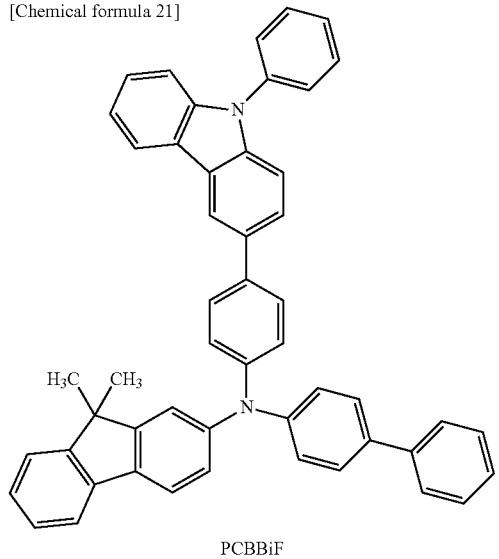

PCBBiF

A method for fabricating a light-emitting element 3 of this example will be described below.
(Light-Emitting Element 3)
The method for fabricating the light-emitting element 3 has some steps in common with the method for fabricating the light-emitting element 1. Here, only different steps from the method for fabricating the light-emitting element 1 are described. First, the thickness of the hole-injection layer 1111 of the light-emitting element 3 was set to 20 nm.

The light-emitting layer 1113 of the light-emitting element 3 was formed by co-evaporation of 2mBnfPDBq, N-(1,1'-biphenyl-4-yl)-N-[4-(9-phenyl-9H-carbazol-3-yl)phenyl]-9,9-dimethyl-9H-fluoren-2-amine (abbreviation: PCBBiF), and [Ir(dppm)$_2$(acac)]. Here, a 20 nm thick layer which was formed with the weight ratio of 2mBnfPDBq to PCBBiF and [Ir(dppm)$_2$(acac)] adjusted to 0.7:0.3:0.05 (=2mBnfPDBq: PCBBiF: [Ir(dppm)$_2$(acac)]) and a 20 nm thick layer which was formed with the weight ratio adjusted to 0.8:0.2:0.05 (=2mBnfPDBq: PCBBiF: [Ir(dppm)$_2$(acac)]) were stacked.

The electron-transport layer 1114 of the light-emitting element 3 was formed by depositing 2mBnfPDBq to a thickness of 20 nm and further depositing BPhen to a thickness of 15 nm.

Table 3 shows an element structure of the light-emitting element fabricated as described above in this example.

TABLE 3

| | First Electrode | Hole-injection Layer | Hole-transport Layer | Light-emitting Layer | Electron-transport Layer | | Electron-injection Layer | Second Electrode |
|---|---|---|---|---|---|---|---|---|
| Light-emitting Element 3 | ITSO 110 nm | DBT3P-II: MoO$_x$ (=4:2) | BPAFLP 20 nm | 2mBnfPDBq: PCBBiF: [Ir(dppm)$_2$(acac)] | 2mBnfPDBq 20 nm | BPhen 15 nm | LiF 1 nm | Al 200 nm |

TABLE 3-continued

| First Electrode | Hole-injection Layer | Hole-transport Layer | Light-emitting Layer | | Electron-transport Layer | Electron-injection Layer | Second Electrode |
|---|---|---|---|---|---|---|---|
| | | 20 nm | (=0.7:0.3:0.05) 20 nm | (=0.8:0.2:0.05) 20 nm | | | |

The light-emitting element of this example was sealed in a glove box under a nitrogen atmosphere so as not to be exposed to the air. Then, the operation characteristics of the light-emitting element were measured. Note that the measurement was carried out at room temperature (in an atmosphere kept at 25° C.).

Figure 16:
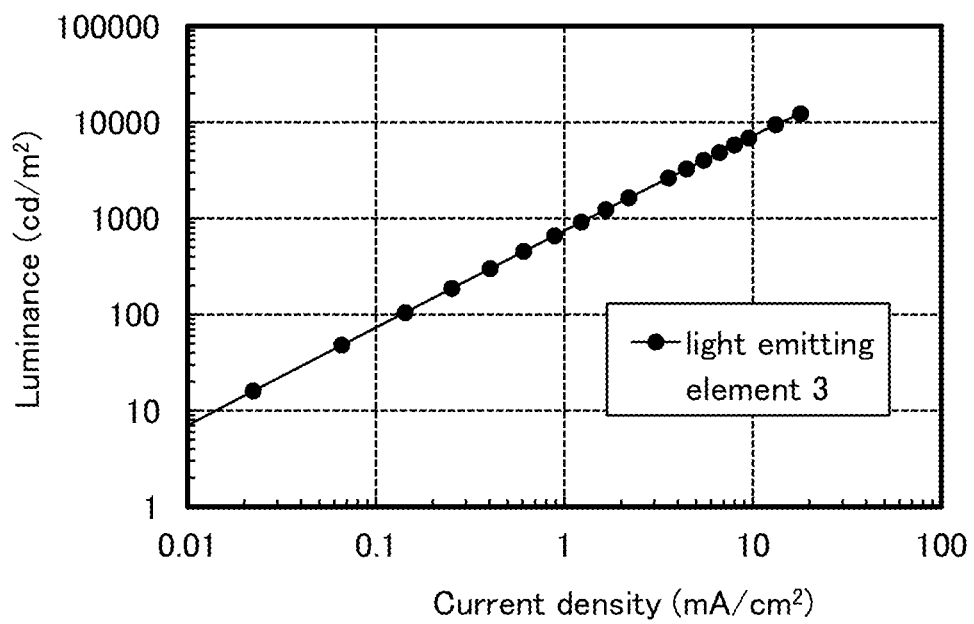
FIG. 16 shows current density-luminance characteristics of a light-emitting element in Example 3.
Figure 17:
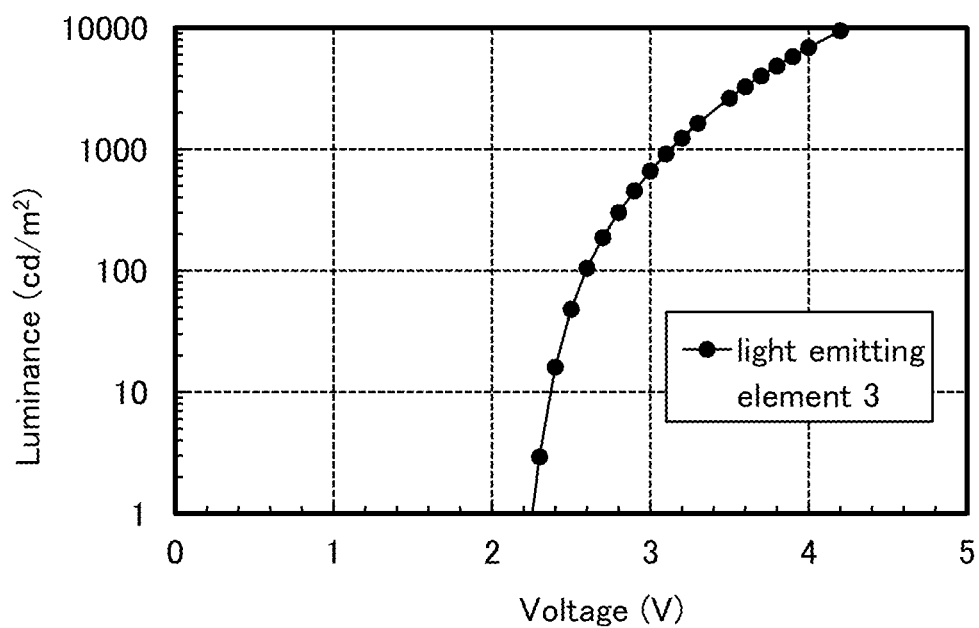
FIG. 17 shows voltage-luminance characteristics of the light-emitting element in Example 3.
Figure 18:
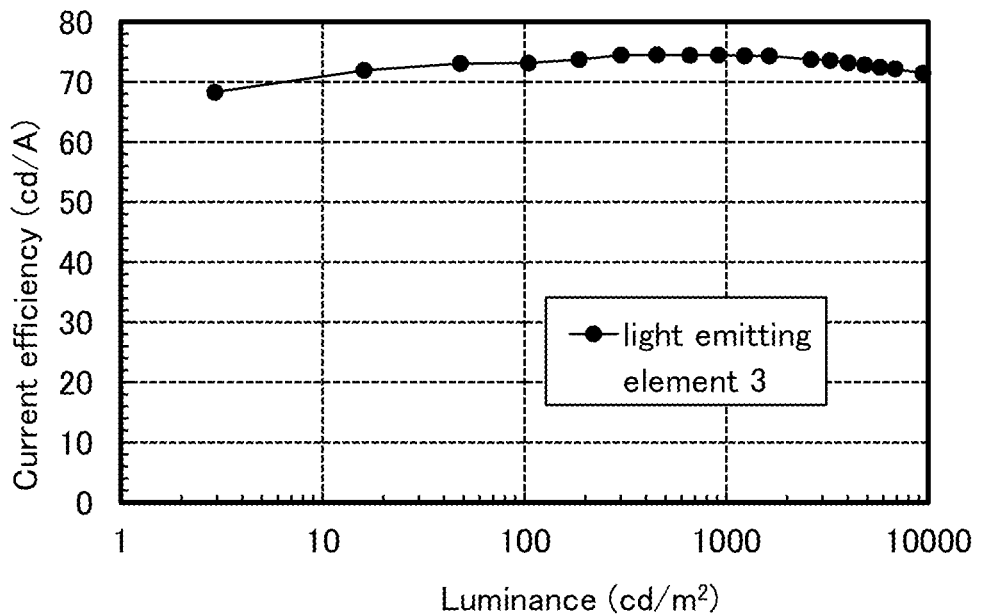
FIG. 18 shows luminance-current efficiency characteristics of the light-emitting element in Example 3.
Figure 19:
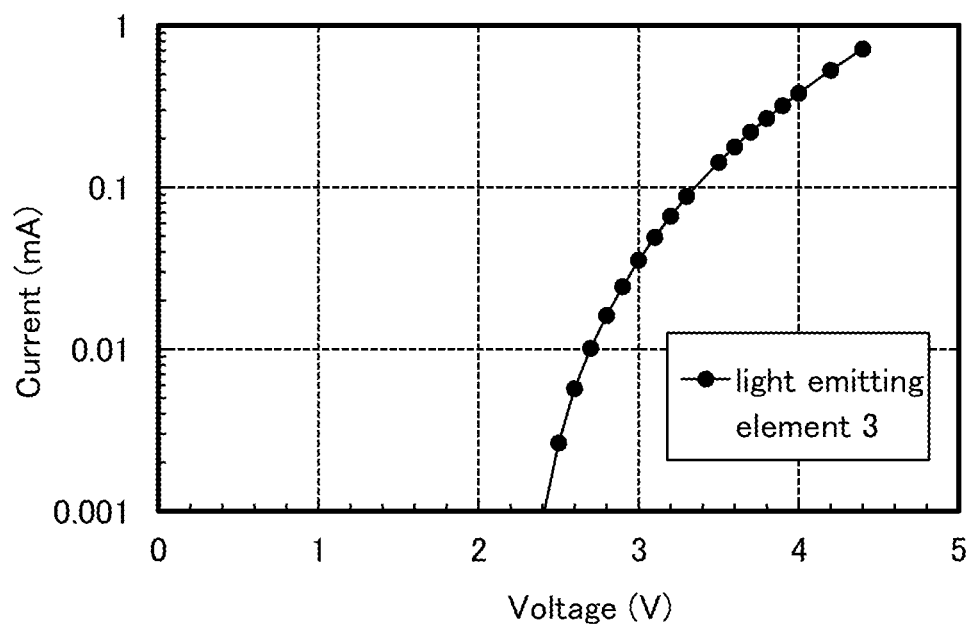
FIG. 19 shows voltage-current characteristics of the light-emitting element in Example 3.
Figure 20:
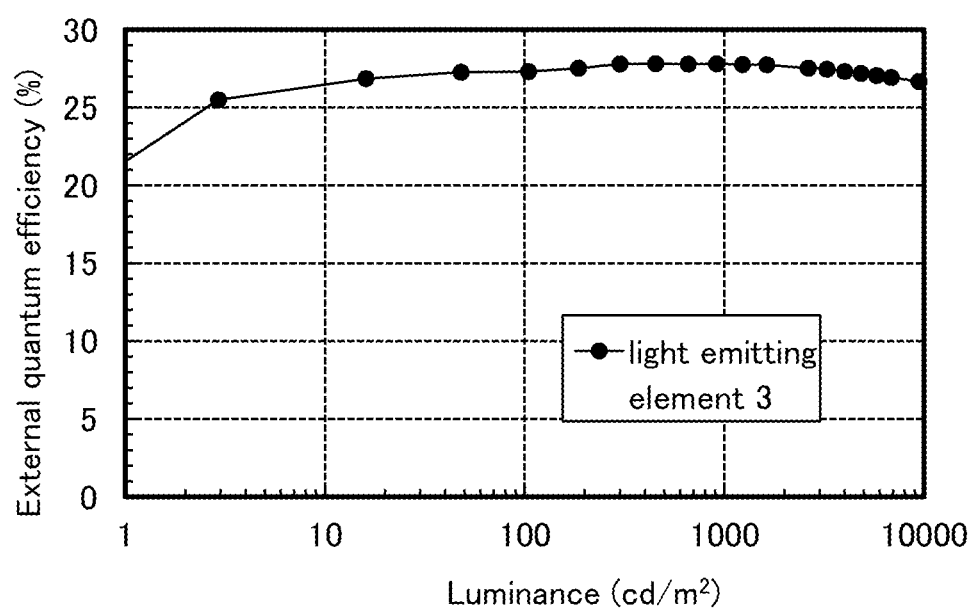
FIG. 20 shows luminance-external quantum efficiency characteristics of the light-emitting element in Example 3.

FIG. 16 shows current density-luminance characteristics of the light-emitting element 3. In FIG. 16, the horizontal axis represents current density (mA/cm$^2$), and the vertical axis represents luminance (cd/m$^2$). FIG. 17 shows voltage-luminance characteristics. In FIG. 17, the horizontal axis represents voltage (V) and the vertical axis represents luminance (cd/m$^2$). FIG. 18 shows luminance-current efficiency characteristics. In FIG. 18, the horizontal axis represents luminance (cd/m$^2$) and the vertical axis represents current efficiency (cd/A). FIG. 19 shows voltage-current characteristics. In FIG. 19, the horizontal axis represents voltage (V) and the vertical axis represents current (mA). FIG. 20 shows luminance-external quantum efficiency characteristics. In FIG. 20, the horizontal axis represents luminance (cd/m$^2$) and the vertical axis represents external quantum efficiency (%). Table 4 shows the voltage (V), current density (mA/cm$^2$), CIE chromaticity coordinates (x, y), current efficiency (cd/A), power efficiency (lm/W), and external quantum efficiency (%) of the light-emitting element 3 at a luminance of 900 cd/m$^2$.

TABLE 4

| | Voltage (V) | Current Density (mA/cm$^2$) | Chromaticity x | Chromaticity y | Luminance (cd/m$^2$) | Current Efficiency (cd/A) | Power Efficiency (lm/W) | External Quantum Efficiency (%) |
|---|---|---|---|---|---|---|---|---|
| Light-emitting Element 3 | 3.1 | 1.2 | 0.56 | 0.44 | 900 | 74 | 75 | 28 |

The CIE chromaticity coordinates (x, y) at a luminance of 900 cd/m$^2$ of the light-emitting element 3 were (0.56, 0.44) and the light-emitting element 3 exhibited orange light emission. The results show that orange light emission originating from [Ir(dppm)$_2$(acac)] was provided from the light-emitting element 3.

The measurement results of the operation characteristics showed that the light-emitting element 3 has high emission efficiency and a low drive voltage.

Figure 21:
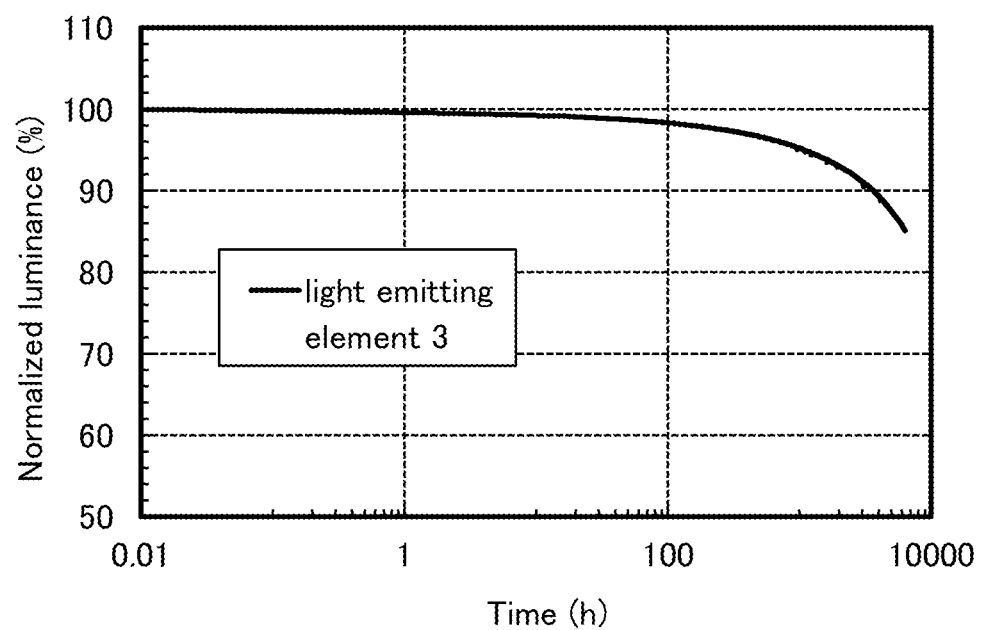
FIG. 21 shows results of a reliability test of the light-emitting element in Example 3.

A reliability test of the light-emitting element 3 was conducted. Results of the reliability test are shown in FIG. 21. In FIG. 21, the vertical axis represents normalized luminance (%) with the initial luminance taken as 100%, and the horizontal axis represents driving time (h) of the element. In the reliability test, which was conducted at room temperature, the light-emitting element 3 was driven under the conditions where the initial luminance was set to 5000 cd/m$^2$ and the current density was constant. FIG. 21 shows that the light-emitting element 3 kept 85% of the initial luminance after 6400 hours. The results of the reliability test showed that the light-emitting element 3 has a long lifetime.

EXAMPLE 4

Synthesis Example 2

This example describes a method for synthesizing 2-{3-[3-(benzo[b]naphtho[1,2-d]furan-6-yl)phenyl]phenyl}dibenzo[f,h]quinoxaline (abbreviation: 2mBnfBPDBq(6)) represented by Structural Formula (209).

[Chemical formula 22]

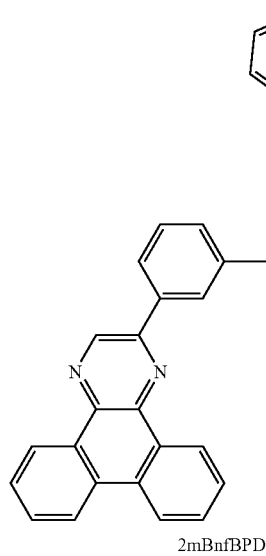

2mBnfBPDBq(6)

Synthesis Scheme (C-1) of 2mBnfBPDBq(6) is shown below.

[Chemical formula 23]

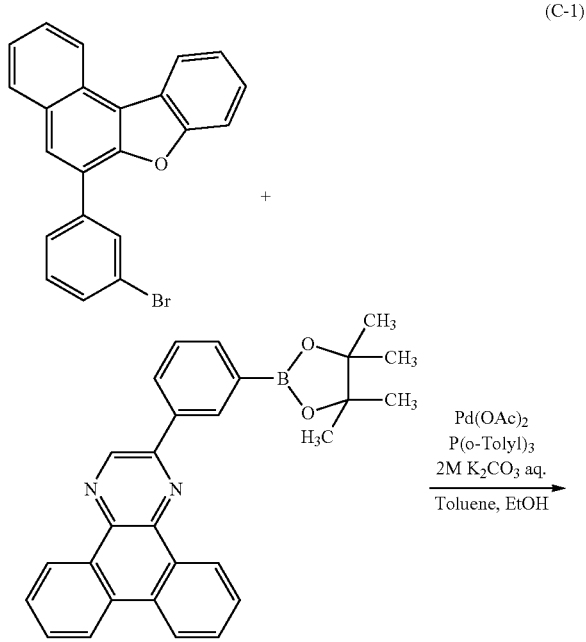

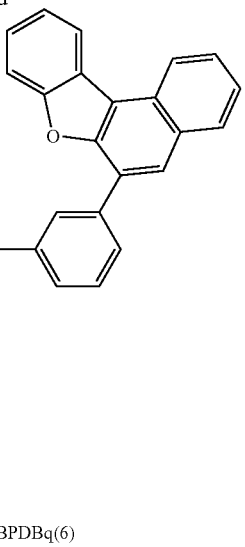

2mBnfBPDBq(6)

In a 200-mL three-neck flask were put 1.1 g (3.0 mmol) of 6-(3-bromophenyl)benzo[b]naphtho[1,2-d]furan, 1.4 g (3.2 mmol) of 2-[3-(4,4,5,5-tetramethyl-1,3,2-dioxaborolan-2-yl)phenyl]dibenzo[f,h]quinoxaline, 0.10 g (0.33 mmol) of tri(ortho-tolyl)phosphine, 30 mL of toluene, 3 mL of ethanol, and 3 mL of a 2.0 M aqueous solution of potassium carbonate. The mixture was degassed by being stirred under reduced pressure, and the air in the flask was replaced with nitrogen. To this mixture was added 49 mg (0.22 mmol) of palladium (II)acetate. The mixture was stirred at 80° C. under a nitrogen stream for 20 hours. After the predetermined time elapsed, the temperature was lowered to 60° C., and toluene and water were added, followed by stirring for 10 minutes; then, a solid was collected by suction filtration. A suspension which was formed by adding methanol to this solid was irradiated with ultrasonic waves, and a solid was collected by suction filtration. A toluene solution of the resulting solid was suction-filtered through alumina and Celite, and the resulting filtrate was concentrated to give a solid. Further, this solid was recrystallized from toluene to give 1.1 g of a pale yellow powder in a yield of 62%.

By a train sublimation method, 1.1 g of the pale yellow powder was purified. The sublimation purification was conducted by heating of the pale yellow powder at 330° C. under a pressure of 3.1 Pa with a flow rate of argon gas of 5.0 mL/min for 14 hours. As a result of the sublimation purification, 1.0 g of a pale yellow powder was provided at a collection rate of 94%.

This compound was identified as 2mBnfBPDBq(6), which was the target substance, by nuclear magnetic resonance (NMR) spectroscopy.

$^1$H NMR data of the above substance are as follows:
$^1$H NMR (CDCl$_3$, 300 MHz): δ=7.47-7.61 (m, 3H), 7.69-7.91 (m, 10H), 8.04-8.08 (m, 1H), 8.11 (d, J=8.4 Hz, 1H), 8.14 (s, 1H), 8.34-8.40 (m, 2H), 8.45-8.48 (m, 1H), 8.64-8.73 (m, 4H), 9.25-9.28 (m, 1H), 9.43-9.50 (m, 2H).

Figure 22A:
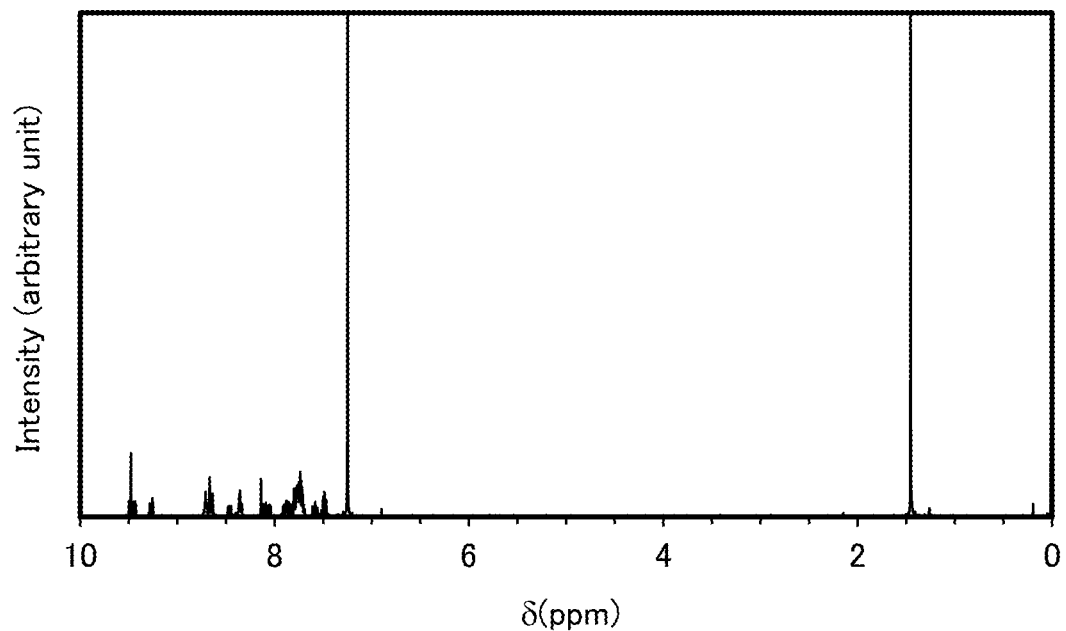
FIGS. 22A and 22B show $^1_H$ NMR charts of 2-{3-[3-(benzo[b]naphtho[1,2-d]furan-6-yl)phenyl]phenyl}dibenzo[f,h]quinoxaline (abbreviation: 2mBnfBPDBq(6)).
Figure 22B:
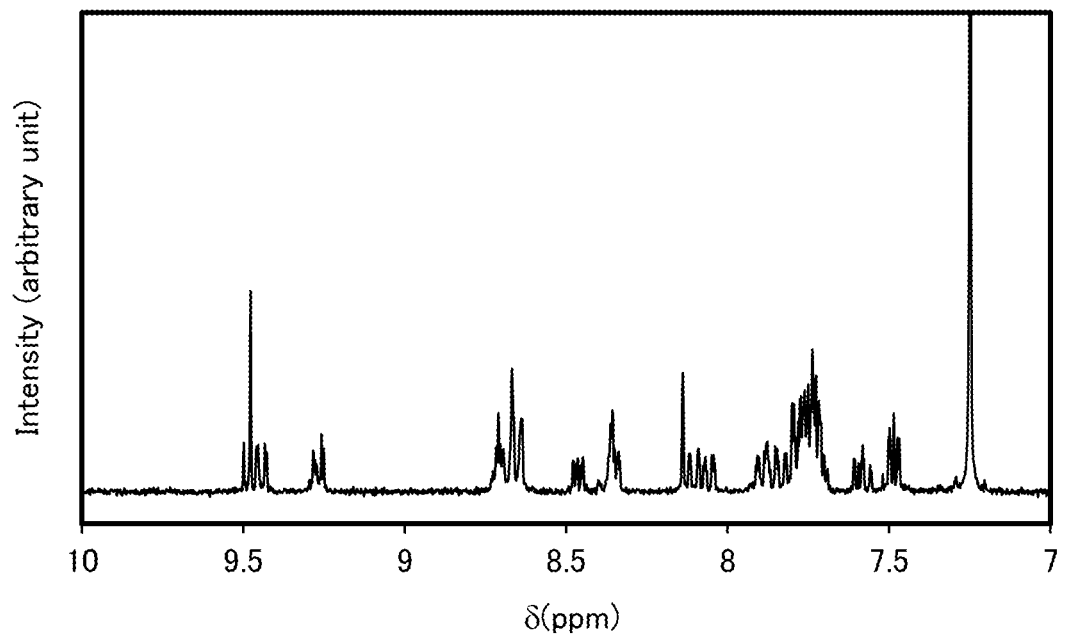

In addition, FIGS. 22A and 22B show $^1$H NMR charts. Note that FIG. 22B is a chart showing an enlarged part of FIG. 22A in the range of 7.00 ppm to 10.0 ppm.

Figure 23A:
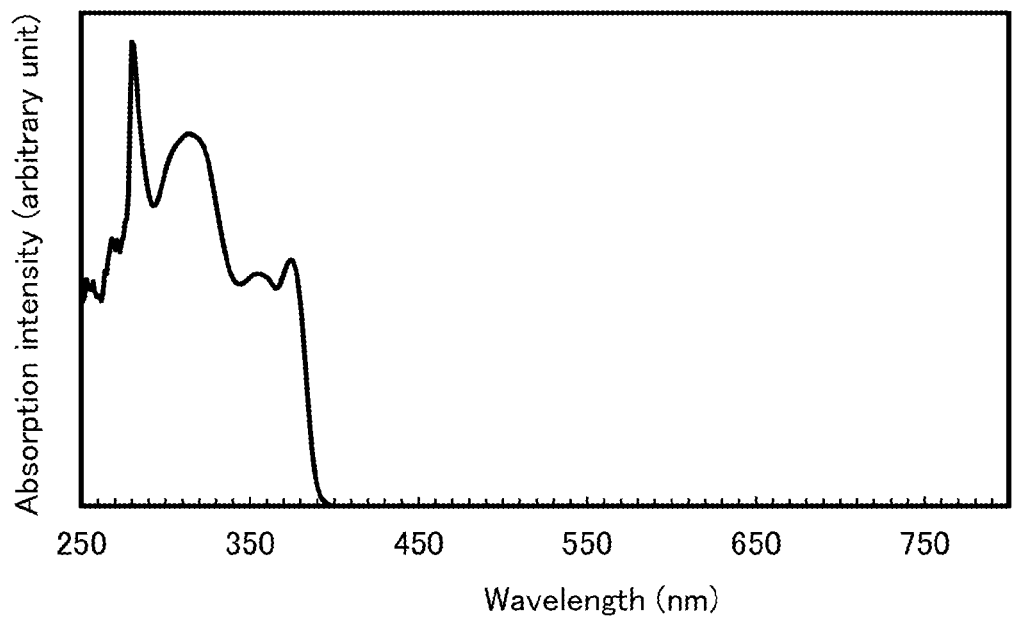
FIGS. 23A and 23B show an absorption spectrum and an emission spectrum of 2mBnfBPDBq(6) in a toluene solution of 2mBnfBPDBq(6).
Figure 23B:
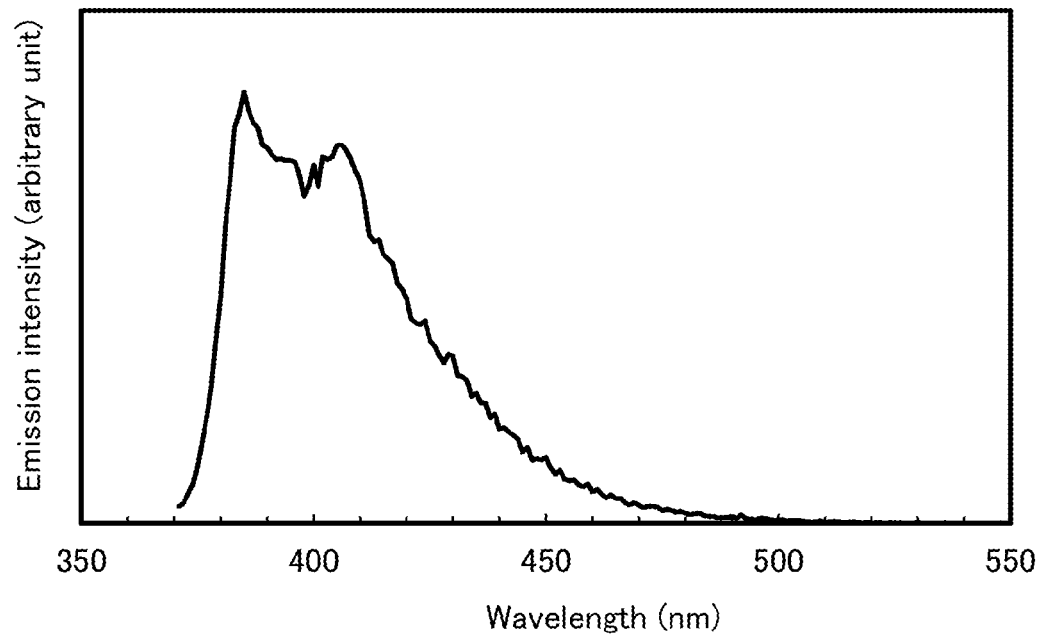
Figure 24A:
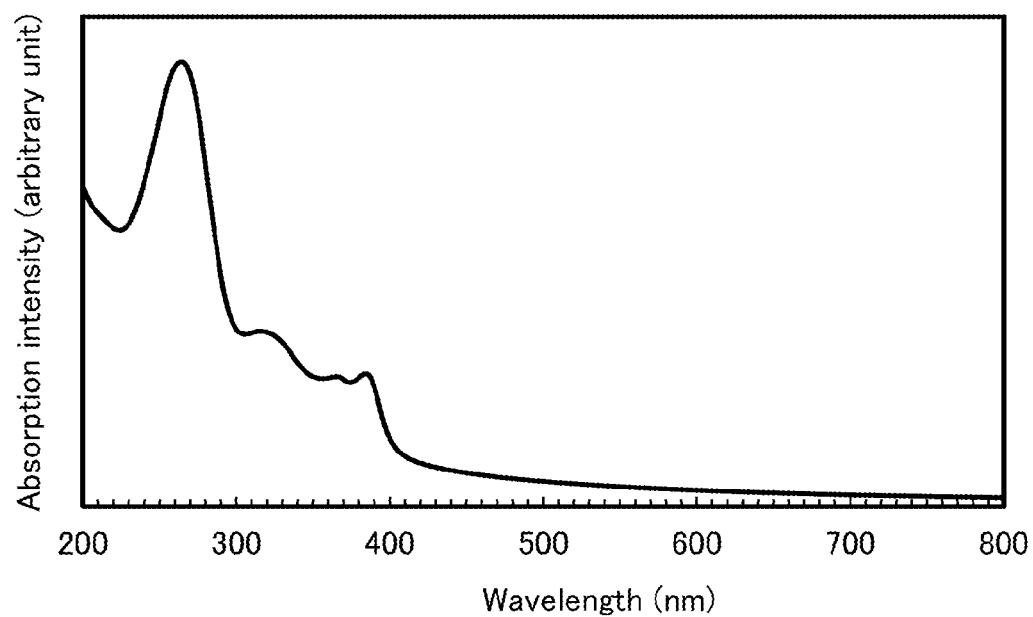
FIGS. 24A and 24B show an absorption spectrum and an emission spectrum of a thin film of 2mBnfBPDBq(6).
Figure 24B:
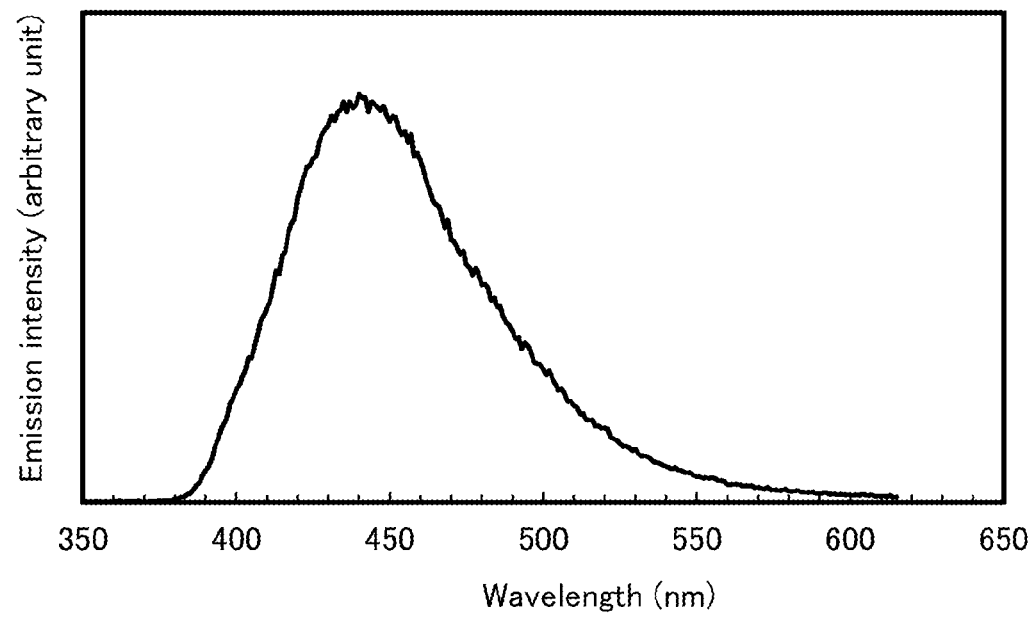

Further, FIG. 23A shows an absorption spectrum of 2mBnfBPDBq(6) in a toluene solution of 2mBnfBPDBq(6), and FIG. 23B shows an emission spectrum thereof. FIG. 24A shows an absorption spectrum of a thin film of 2mBnfBPDBq(6) and FIG. 24B shows an emission spectrum thereof. The spectra were calculated in a similar manner to Example 1. In FIGS. 23A and 23B and FIGS. 24A and 24B, the horizontal axis represents wavelength (nm) and the vertical axis represents intensity (arbitrary unit). In the case of the toluene solution, absorption peaks are observed around 355 nm and 374 nm, and emission wavelength peaks are observed at 385 nm and 405 nm (excitation wavelength: 362 nm). In the case of the thin film, absorption peaks are observed around 264 nm, 317 nm, 366 nm, and 384 nm, and an emission wavelength peak is observed at 441 nm (excitation wavelength: 330 nm).

Further, 2mBnfBPDBq(6) and 2mDBFPDBq-II, which was included in the comparative light-emitting element 2 in Example 2, were subjected to thermogravimetry-differential thermal analysis. The measurement was conducted by using a high vacuum differential type differential thermal balance (TG/DTA 2410SA, produced by Bruker AXS K.K.). The measurement was carried out under a nitrogen stream (flow rate: 200 mL/min) at normal pressure at a temperature rising rate of 10° C./min. From relationship between weight and temperature (thermogravimetry), the 5% weight loss temperature and the melting point of 2mDBFPDBq-II were 426° C. and 248° C., respectively. The 5% weight loss temperature and the melting point of 2mBnfBPDBq(6) were 493° C. and 294° C., respectively, which are higher than those of 2mDBFPDBq-II. Accordingly, it was shown that 2mBnfBPDBq(6) has higher heat resistance than 2mDBFPDBq-II.

Furthermore, 2mBnfBPDBq(6) was subjected to mass spectrometric analysis by LC/MS. The conditions of the analysis were similar to those of the analysis in Example 1. Measurement results are shown in FIGS. 25A and 25B.

Figure 25A:
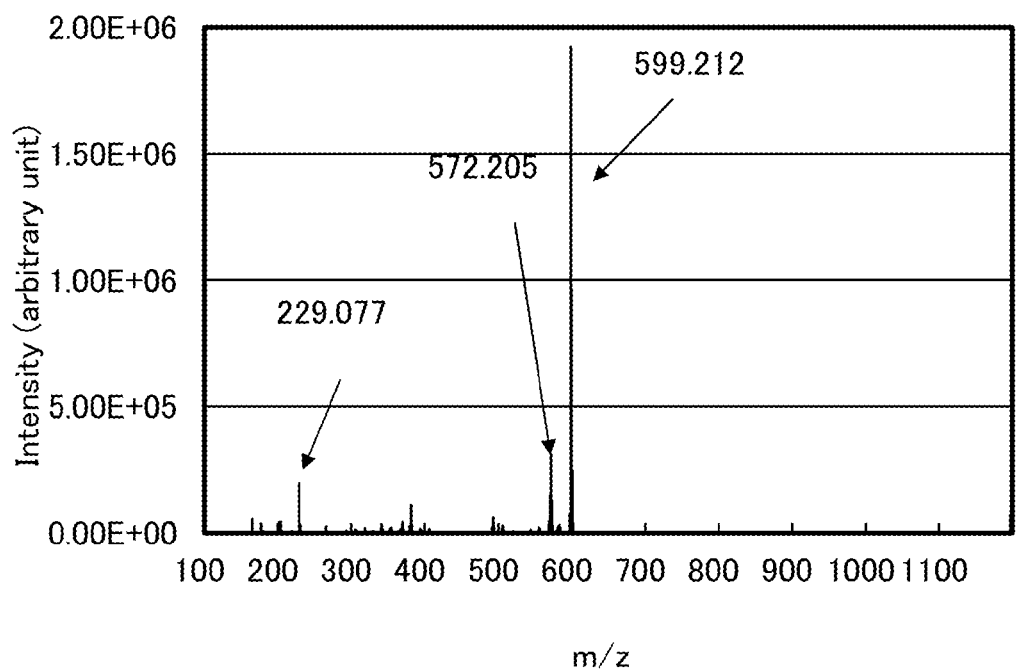
FIGS. 25A and 25B show results of LC/MS analysis of 2mBnfBPDBq(6).
Figure 25B:
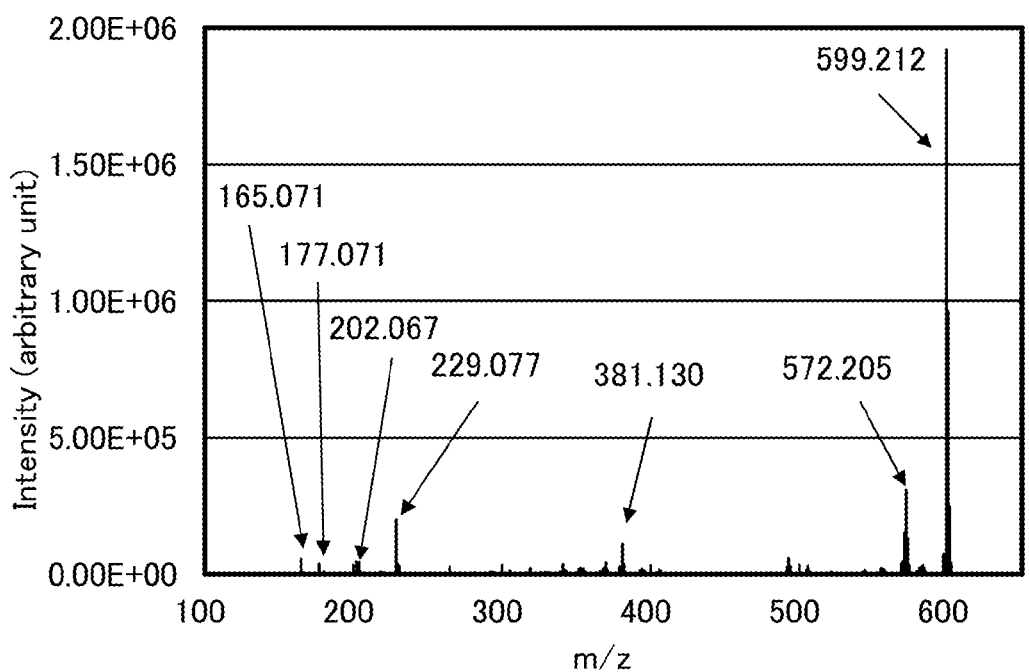

In FIGS. 25A and 25B, owing to the presence and absence of hydrogen ions and isotopes, a plurality of peaks derived from precursor ions of 2mBnfBPDBq(6) are detected mainly around m/z=599 when the collision energy is 50 eV. It was also found that owing to the presence and absence of hydrogen ions and isotopes, a plurality of peaks derived from product ions are detected mainly around each of m/z=165, m/z=177, m/z=202, m/z=229, m/z=381, and m/z=572. The results in FIGS. 25A and 25B are characteristically derived from 2mBnfBPDBq(6) and thus can be regarded as important data in identification of 2mBnfBPDBq(6) contained in a mixture.

The peaks around m/z=572 are presumed to be derived from product ions of cations in the state where one C atom and one N atom are dissociated from the dibenzo[f,h]quinoxaline ring in 2mBnfBPDBq(6). This is one of features of the heterocyclic compound of one embodiment of the present invention. In particular, this is one of features of the heterocyclic compound of one embodiment of the present invention in which a substituent (in 2mBnfBPDBq(6), a biphenyl skeleton bonded to a benzo[b]naphtho[1,2-d]furan skeleton) is bonded to the 2-position of the dibenzo[f,h]quinoxaline ring.

The peaks around m/z=229 are presumed to be derived from product ions of cations of a diazatriphenylenyl group such as a dibenzo[f,h]quinoxaline ring. The peaks around m/z=202, m/z=177, and m/z=165 are also detected, indicating that 2mBnfBPDBq(6), which is the heterocyclic compound of one embodiment of the present invention, includes a dibenzo[f,h]quinoxaline ring.

EXAMPLE 5

In this example, the light-emitting element of one embodiment of the present invention will be described with reference to FIG. 10. Materials used in this example are the same as those used in the above examples, and their chemical formulae are omitted here.

A method for fabricating a light-emitting element 4 of this example will be described below.

(Light-Emitting Element 4)

In the light-emitting element 4, components other than the light-emitting layer 1113 and the electron-transport layer 1114 were formed in a similar manner to the light-emitting element 3. Here, only different steps from the method for fabricating the light-emitting element 3 are described.

The light-emitting layer 1113 of the light-emitting element 4 was formed by co-evaporation of 2mBnfBPDBq(6), PCBBiF, and [Ir(dppm)$_2$(acac)]. Here, a 20 nm thick layer which was formed with the weight ratio of 2mBnfBPDBq(6) to PCBBiF and [Ir(dppm)$_2$(acac)] adjusted to 0.7:0.3:0.05 (=2mBnfBPDBq(6): PCBBiF: [Ir(dppm)$_2$(acac)]) and a 20 nm thick layer which was formed with the weight ratio adjusted to 0.8:0.2:0.05 (=2mBnfBPDBq(6): PCBBiF: [Ir(dppm)$_2$(acac)]) were stacked.

The electron-transport layer 1114 of the light-emitting element 4 was formed by depositing 2mBnfBPDBq(6) to a thickness of 20 nm and further depositing BPhen to a thickness of 10 nm.

Table 5 shows an element structure of the light-emitting element fabricated as described above in this example.

TABLE 5

| | First Electrode | Hole-injection Layer | Hole-transport Layer | Light-emitting Layer | | Electron-transport Layer | Electron-injection Layer | Second Electrode |
|---|---|---|---|---|---|---|---|---|
| Light-emitting Element 4 | ITSO 110 nm | DBT3P-II: MoO$_x$ (=4:2) 20 nm | BPAFLP 20 nm | 2mBnfBPDBq(6): PCBBiF: [Ir(dppm)$_2$(acac)] (=0.7:0.3:0.05) 20 nm | (=0.8:0.2:0.05) 20 nm | 2mBnfBPDBq(6) 20 nm | BPhen 10 nm / LiF 1 nm | Al 200 nm |

The light-emitting element of this example was sealed in a glove box under a nitrogen atmosphere so as not to be exposed to the air. Then, the operation characteristics of the light-emitting element were measured. Note that the measurement was carried out at room temperature (in an atmosphere kept at 25° C.).

Figure 26:
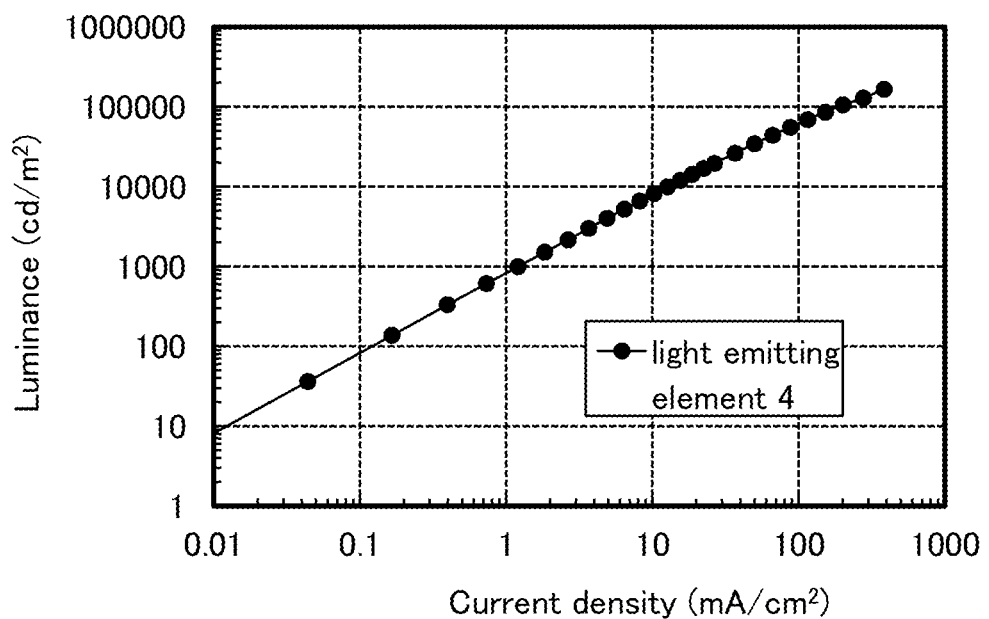
FIG. 26 shows current density-luminance characteristics of a light-emitting element in Example 5.
Figure 27:
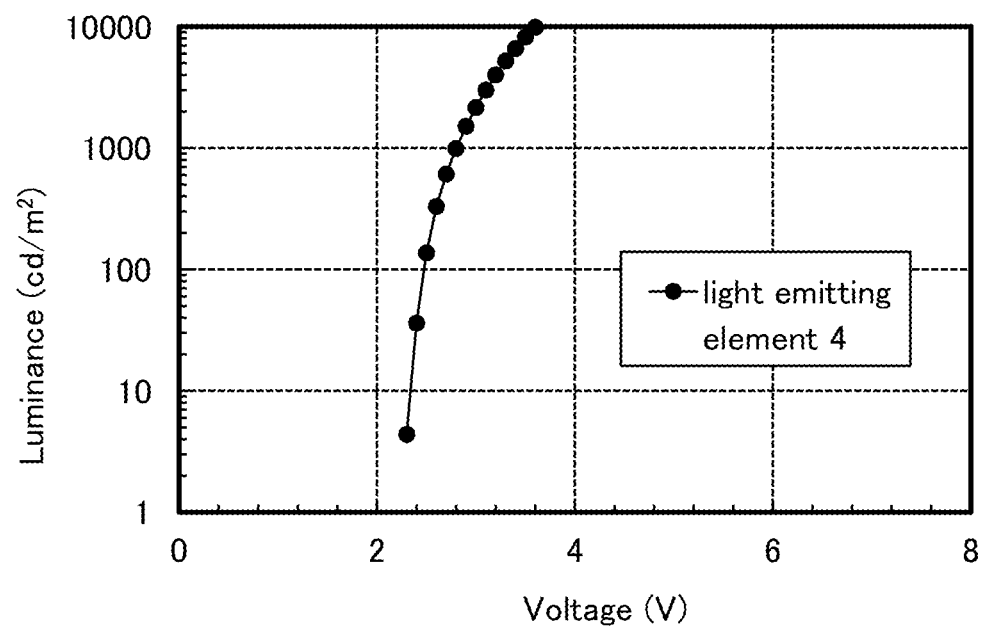
FIG. 27 shows voltage-luminance characteristics of the light-emitting element in Example 5.
Figure 28:
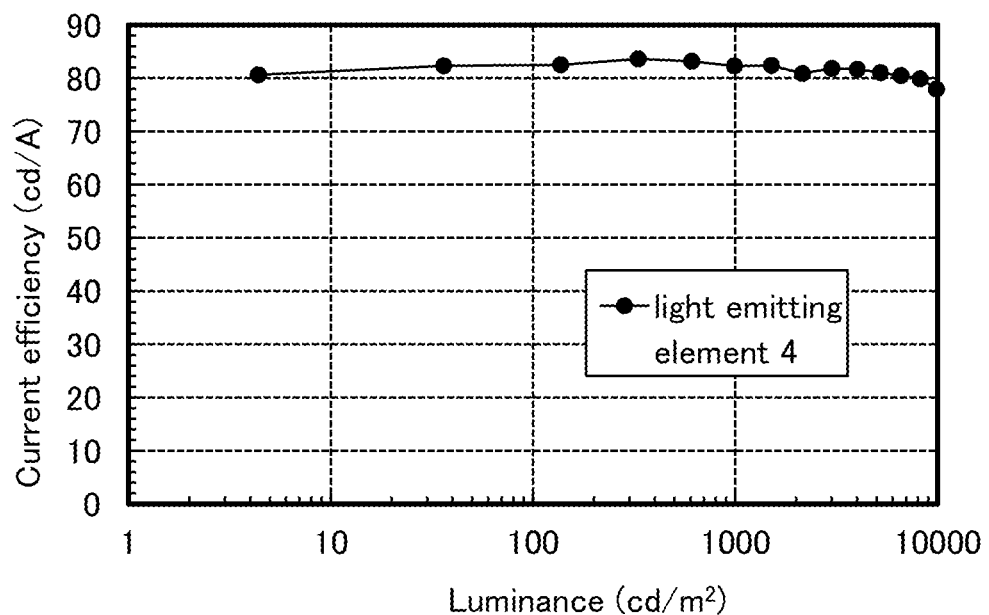
FIG. 28 shows luminance-current efficiency characteristics of the light-emitting element in Example 5.
Figure 29:
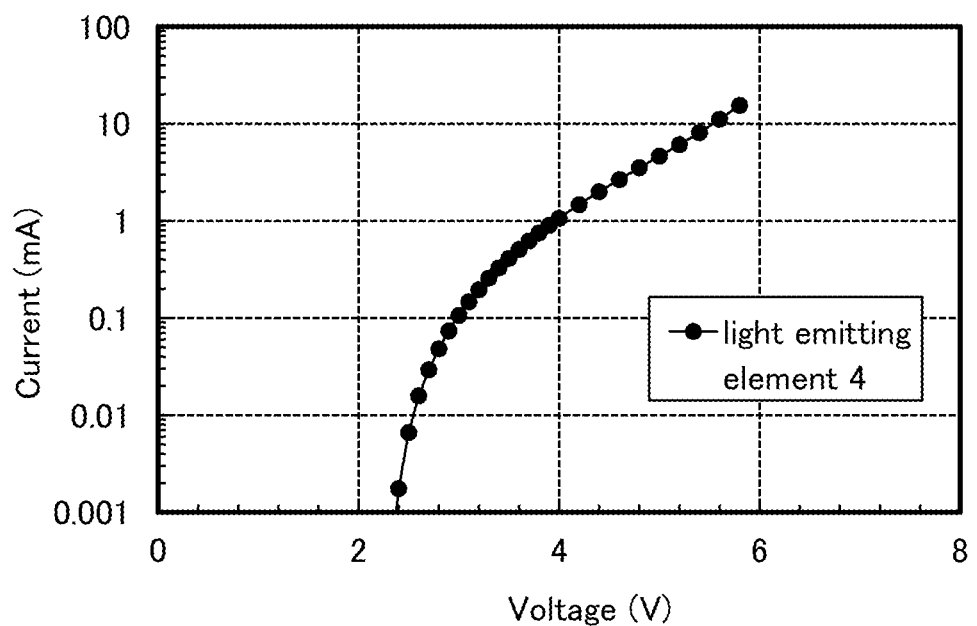
FIG. 29 shows voltage-current characteristics of the light-emitting element in Example 5.
Figure 30:
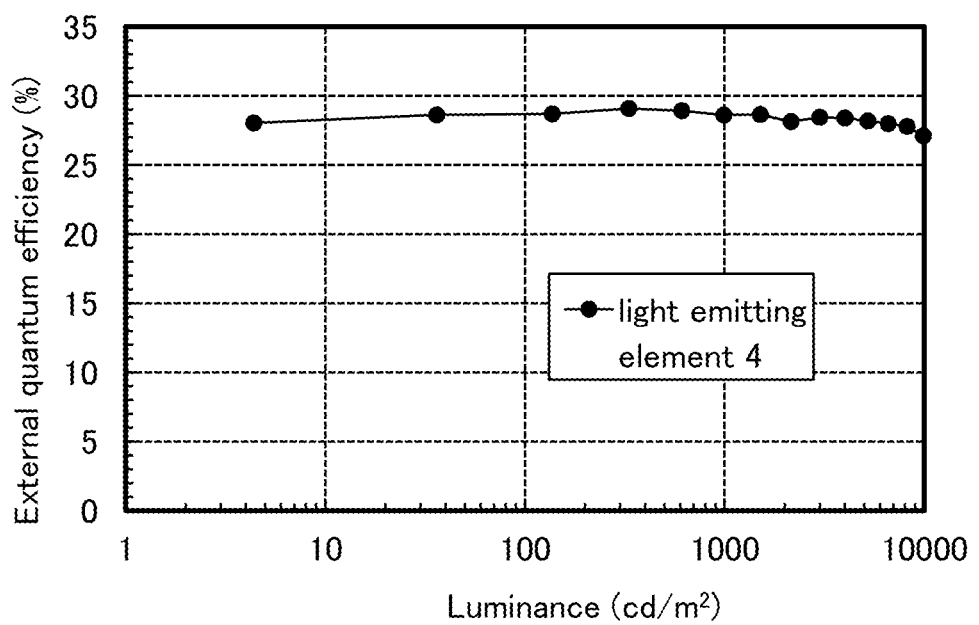
FIG. 30 shows luminance-external quantum efficiency characteristics of the light-emitting element in Example 5.

FIG. 26 shows current density-luminance characteristics of the light-emitting element 4. In FIG. 26, the horizontal axis represents current density (mA/cm$^2$), and the vertical axis represents luminance (cd/m$^2$). FIG. 27 shows voltage-luminance characteristics. In FIG. 27, the horizontal axis represents voltage (V) and the vertical axis represents luminance (cd/m$^2$). FIG. 28 shows luminance-current efficiency characteristics. In FIG. 28, the horizontal axis represents luminance (cd/m$^2$) and the vertical axis represents current efficiency (cd/A). FIG. 29 shows voltage-current characteristics. In FIG. 29, the horizontal axis represents voltage (V) and the vertical axis represents current (mA). FIG. 30 shows luminance-external quantum efficiency characteristics. In FIG. 30, the horizontal axis represents luminance (cd/m$^2$) and the vertical axis represents external quantum efficiency (%). Table 6 shows the voltage (V), current density (mA/cm$^2$), CIE chromaticity coordinates (x, y), current efficiency (cd/A), power efficiency (lm/W), and external quantum efficiency (%) of the light-emitting element 4 at a luminance of 600 cd/m$^2$.

TABLE 6

| | Voltage (V) | Current Density (mA/cm$^2$) | Chromaticity x | Chromaticity y | Luminance (cd/m$^2$) | Current Efficiency (cd/A) | Power Efficiency (lm/W) | External Quantum Efficiency (%) |
|---|---|---|---|---|---|---|---|---|
| Light-emitting Element 4 | 2.7 | 0.73 | 0.54 | 0.45 | 600 | 83 | 97 | 29 |

The CIE chromaticity coordinates (x, y) at a luminance of 600 cd/m$^2$ of the light-emitting element 4 were (0.54, 0.45) and the light-emitting element 4 exhibited orange light emission. The results show that orange light emission originating from [Ir(dppm)$_2$(acac)] was provided from the light-emitting element 4.

The measurement results of the operation characteristics showed that the light-emitting element 4 has high emission efficiency and a low drive voltage.

Figure 31:
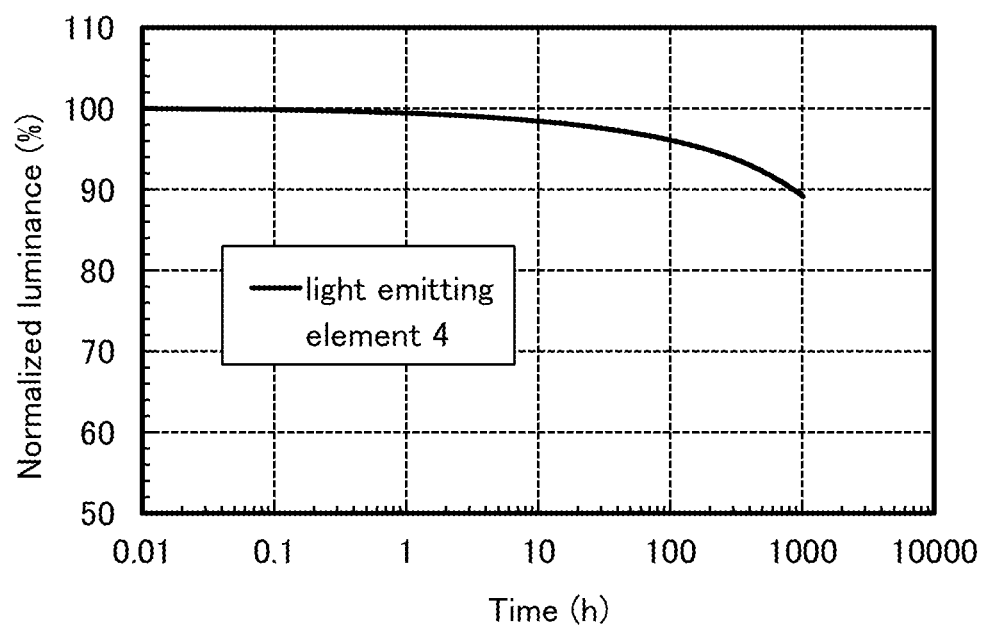
FIG. 31 shows results of a reliability test of the light-emitting element in Example 5.

A reliability test of the light-emitting element 4 was conducted. Results of the reliability test are shown in FIG. 31. In FIG. 31, the vertical axis represents normalized luminance (%) with the initial luminance taken as 100%, and the horizontal axis represents driving time (h) of the element. In the reliability test, which was conducted at room temperature, the light-emitting element 4 was driven under the conditions where the initial luminance was set to 5000 cd/m$^2$ and the current density was constant. FIG. 31 shows that the light-emitting element 4 kept 89% of the initial luminance after 1000 hours. The results of the reliability test showed that the light-emitting element 4 has a long lifetime.

EXAMPLE 6

Synthesis Example 3

This example describes a method for synthesizing 2-{3-[3-(benzo[b]naphtho[1,2-d]furan-8-yl)phenyl]phenyl}dibenzo[f,h]quinoxaline (abbreviation: 2mBnfBPDBq) represented by a structural formula below.

[Chemical formula 24]

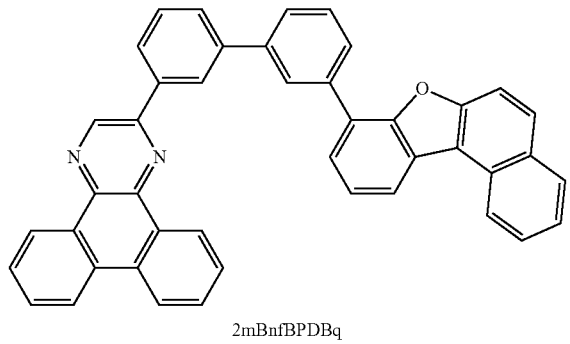

2mBnfBPDBq

Step 1: Synthesis of 3-Chloro-2-fluorobenzeneboronic Acid

Synthesis Scheme (D-1) of Step 1 is shown below.

[Chemical formula 25]

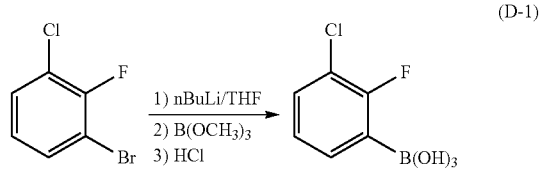

(D-1)

In a 500-mL three-neck flask was put 16 g (72 mmol) of 1-bromo-3-chloro-2-fluorobenzene, and the air in the flask was replaced with nitrogen; then, 200 mL of tetrahydrofuran was added and the solution was cooled down to −80° C. under a nitrogen stream. To this solution, 48 mL (76 mmol) of n-butyl lithium (a 1.6 mol/L hexane solution) was added dropwise with a syringe, and then the mixture was stirred for 1.5 hours at the same temperature. After stirring, 9.0 mL (80 mmol) of trimethyl borate was added to this mixture. While the temperature was raised to room temperature, the mixture was stirred for about 19 hours. After stirring, about 100 mL of a 1 mol/L hydrochloric acid was added to the resulting solution and the mixture was stirred. The organic layer of this mixture was washed with water and the aqueous layer was subjected to extraction with toluene twice. The solution of the extract and the organic layer were combined and washed with a saturated aqueous solution of sodium chloride. The resulting organic layer was dried over magnesium sulfate, and this mixture was gravity-filtered. The resulting filtrate was concentrated to give 4.5 g of a pale yellow solid of a target substance, in a yield of 35%.

Step 2: Synthesis of 1-(3-Chloro-2-fluorophenyl)-2-naphthol

Synthesis Scheme (D-2) of Step 2 is shown below.

[Chemical formula 26]

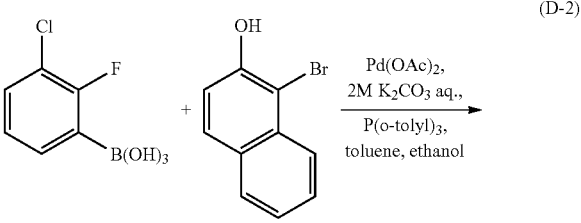

(D-2)

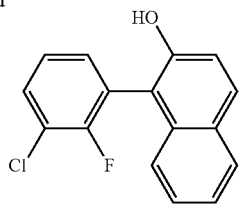

In a 200-mL three-neck flask were put 5.8 g (26 mmol) of 1-bromo-2-naphthol, 4.5 g (26 mmol) of 3-chloro-2-fluorobenzeneboronic acid, and 0.40 g (1.3 mmol) of tri(ortho-tolyl)phosphine, and the air in the flask was replaced with nitrogen. To this mixture, 150 mL of toluene, 50 mL of ethanol, and 21 mL of an aqueous solution of potassium carbonate (2.0 mol/L) were added. The mixture was degassed by being stirred while the pressure in the flask was reduced; then, the air in the flask was replaced with nitrogen. To this mixture was added 58 mg (0.26 mmol) of palladium(II)acetate, and the resulting mixture was stirred at 90° C. under a nitrogen stream for 7 hours. After stirring, the organic layer of the mixture was washed with water and the aqueous layer was subjected to extraction with toluene. The solution of the extract combined with the organic layer was washed with a saturated aqueous solution of sodium chloride, and the organic layer was dried over magnesium sulfate. The resulting mixture was gravity-filtered, and the resulting filtrate was concentrated to give a brown liquid. The liquid was purified by silica gel column chromatography using a mixed solvent (toluene:hexane=9:1) as a developing solvent, so that 3.1 g of a brown liquid of a target substance was produced in a yield of 44%.

Step 3: Synthesis of 8-Chlorobenzo[b]naphtho[1,2-d]furan

Synthesis Scheme (D-3) of Step 3 is shown below.

[Chemical formula 27]

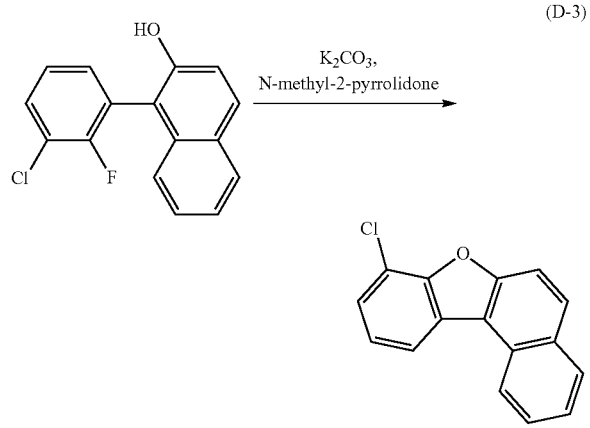

In a 300-mL recovery flask were put 3.1 g (11 mmol) of 1-(3-chloro-2-fluorophenyl)-2-naphthol, 70 mL of N-methyl-2-pyrrolidone, and 4.2 g (31 mmol) of potassium carbonate, and this mixture was stirred at 150° C. in air for 7 hours. After stirring, about 50 mL of water and about 50 mL of hydrochloric acid (1.0 mol/L) were added to the resulting mixture. To the resulting solution was added about 100 mL of ethyl acetate; then, the aqueous layer was subjected to extraction with ethyl acetate three times. The solution of the extract combined with the organic layer was washed with a saturated aqueous solution of sodium hydrogen carbonate and a saturated aqueous solution of sodium chloride, and magnesium sulfate was then added. The mixture was gravity-filtered, and the resulting filtrate was concentrated to give 2.9 g of a pale brown solid of a target substance in a yield of over 99%.

Step 4: Synthesis of 2-(Benzo[b]naphtho[1,2-d]furan-8-yl)-4,4,5,5-tetramethyl-1,3,2-dioxaborolane Synthesis Scheme (D-4) of Step 4 is shown below.

[Chemical formula 28]

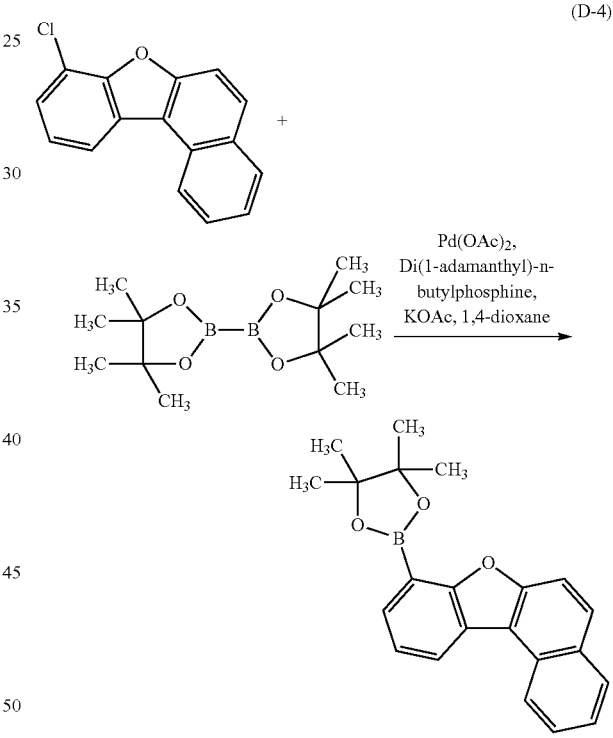

In a 200-mL three-neck flask were put 2.5 g (10 mmol) of 8-chlorobenzo[b]naphtho[1,2-d]furan, 2.5 g (10 mmol) of bis(pinacolato)diboron, and 2.9 g (30 mmol) of potassium acetate, and the air in the flask was replaced with nitrogen. To this mixture, 50 mL of 1,4-dioxane was added. The mixture was degassed by being stirred while the pressure in the flask was reduced; then, the air in the flask was replaced with nitrogen. To this mixture were added 22 mg (0.10 mmol) of palladium(II)acetate and 71 mg (0.20 mmol) of di(1-adamantyl)-n-butylphosphine, and the mixture was refluxed for 18 hours. After the reflux, the resulting mixture was suction-filtered, and the resulting filtrate was concentrated to give 2.5 g of a brown solid of a target substance in a yield of 73%.

Step 5: Synthesis of 2mBnfBPDBq

Synthesis Scheme (D-5) of Step 5 is shown below.

[Chemical formula 29]

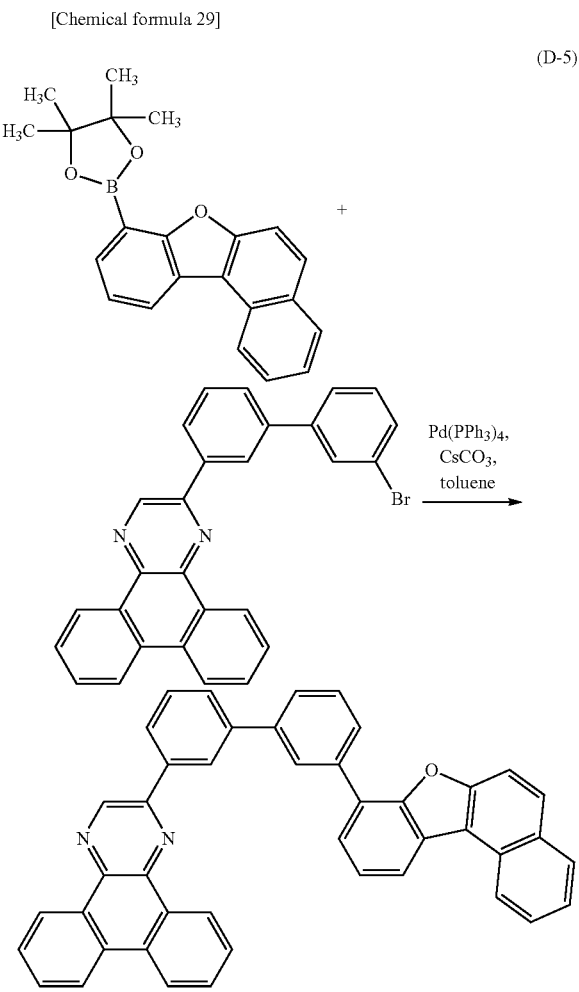

(D-5)

In a 200-mL three-neck flask were put 1.5 g (3.2 mmol) of 2-(3'-bromobiphenyl-3-yl)dibenzo[f,h]quinoxaline, 1.1 g (3.2 mmol) of 2-(benzo[b]naphtho[1,2-d]furan-8-yl)-4,4,5,5-tetramethyl-1,3,2-dioxaborolane, and 3.2 g (10 mmol) of cesium carbonate, and the air in the flask was replaced with nitrogen. Then, 16 mL of toluene was added to this mixture. The mixture was degassed by being stirred while the pressure in the flask was reduced; then, the air in the flask was replaced with nitrogen. After 34 mg (30 µmol) of tetrakis(triphenylphosphine)palladium(0) was added to this mixture, the mixture was stirred at 100° C. under a nitrogen stream for 10 hours. To the resulting mixture, about 100 mL of toluene was added; then, this mixture was refluxed, in which a solid was precipitated and dissolved. This mixture was suction-filtered. The resulting filtrate was left standing, whereby recrystallization occurred. Thus, 1.0 g of a pale yellow solid of a target substance was produced in a yield of 51%.

By a train sublimation method, 0.76 g of the pale yellow solid was purified. The sublimation purification was conducted by heating of the pale yellow solid at 330° C. under a pressure of 3.2 Pa. As a result of the sublimation purification, 0.36 g of a pale yellow solid was provided at a collection rate of 51%.

This compound was identified as 2mBnfBPDBq, which was the target substance, by nuclear magnetic resonance (NMR) spectroscopy.

$^1$H NMR data of the above substance are as follows:

$^1$H NMR (CDCl$_3$, 500 MHz): δ=7.58 (t, J=4.2 Hz, 1H), 7.62 (t, J=4.7 Hz, 1H), 7.73-7.86 (m, 10H), 7.90 (d, J=4.8 Hz, 1H), 7.92 (d, J=5.1 Hz, 1H), 8.04 (t, J=4.5 Hz, 2H), 8.32 (s, 1H), 8.36 (d, J=4.5 Hz, 1H), 8.45 (d, J=4.2 Hz, 1H), 8.66-8.71 (m, 4H), 9.26 (dd, J$_1$=4.5 Hz, J$_2$=1.2 Hz, 1H), 9.45 (d, J=4.8 Hz, 1H), 9.49 (s, 1H).

Figure 32A:
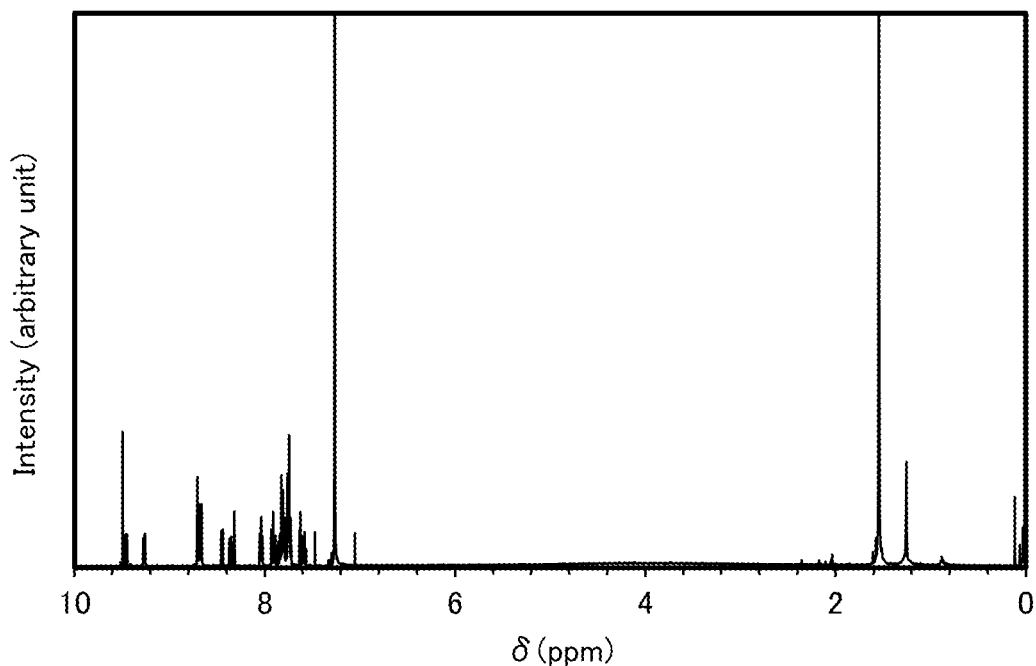
FIGS. 32A and 32B show $^1$H NMR charts of 2-{3-[3-(benzo[b]naphtho[1,2-d]furan-8-yl)phenyl]phenyl}dibenzo[f,h]quinoxaline (abbreviation: 2mBnfBPDBq).
Figure 32B:
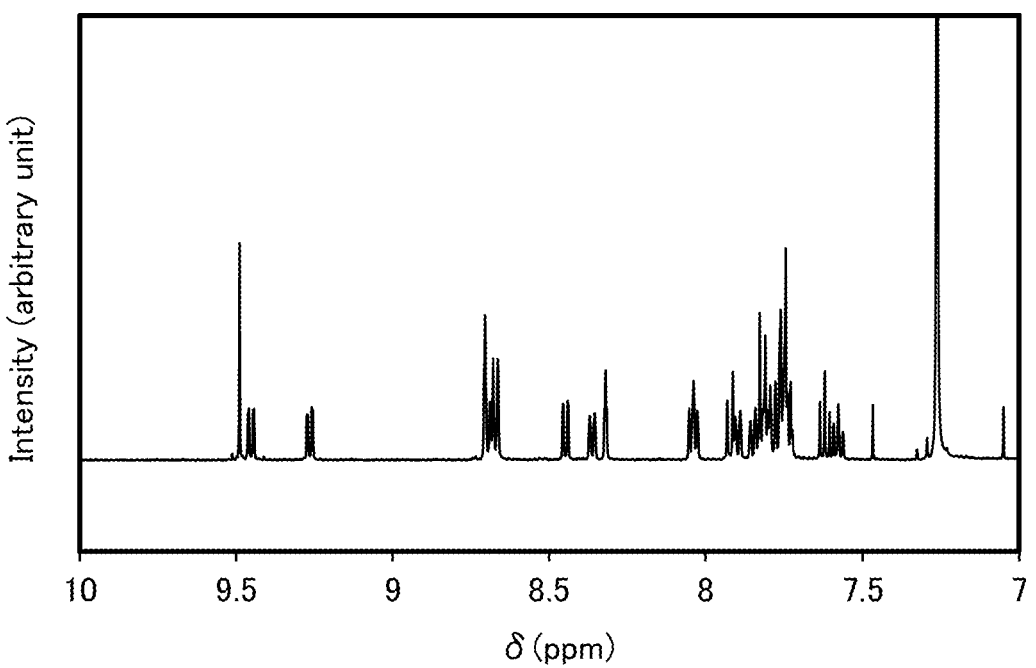

In addition, FIGS. 32A and 32B show $^1$H NMR charts. Note that FIG. 32B is a chart showing an enlarged part of FIG. 32A in the range of 7.00 ppm to 10.0 ppm.

Figure 33A:
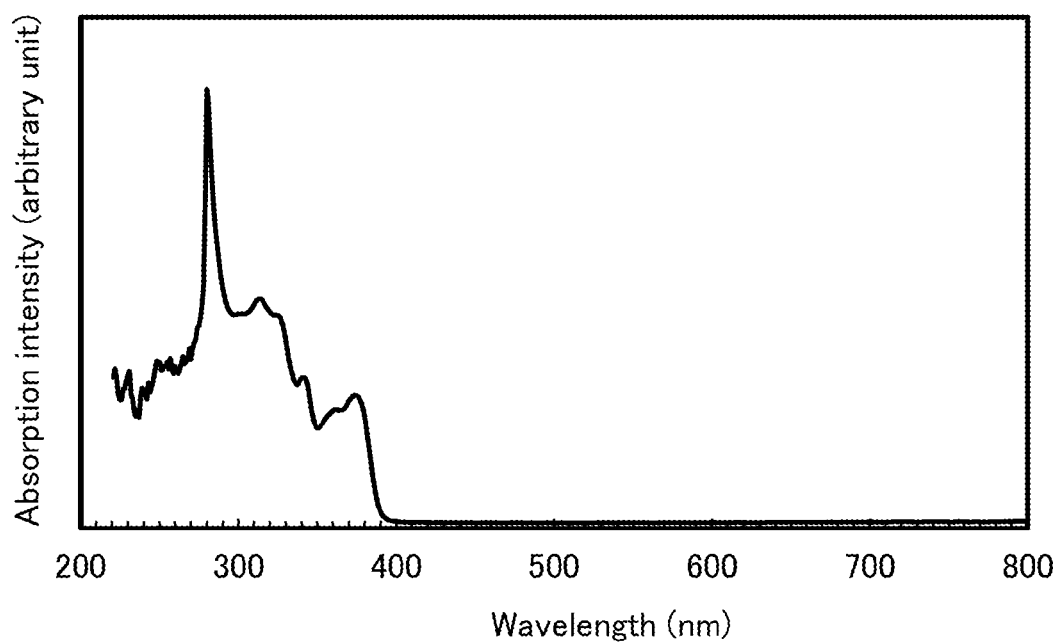
FIGS. 33A and 33B show an absorption spectrum and an emission spectrum of 2mBnfBPDBq in a toluene solution of 2mBnfBPDBq.
Figure 33B:
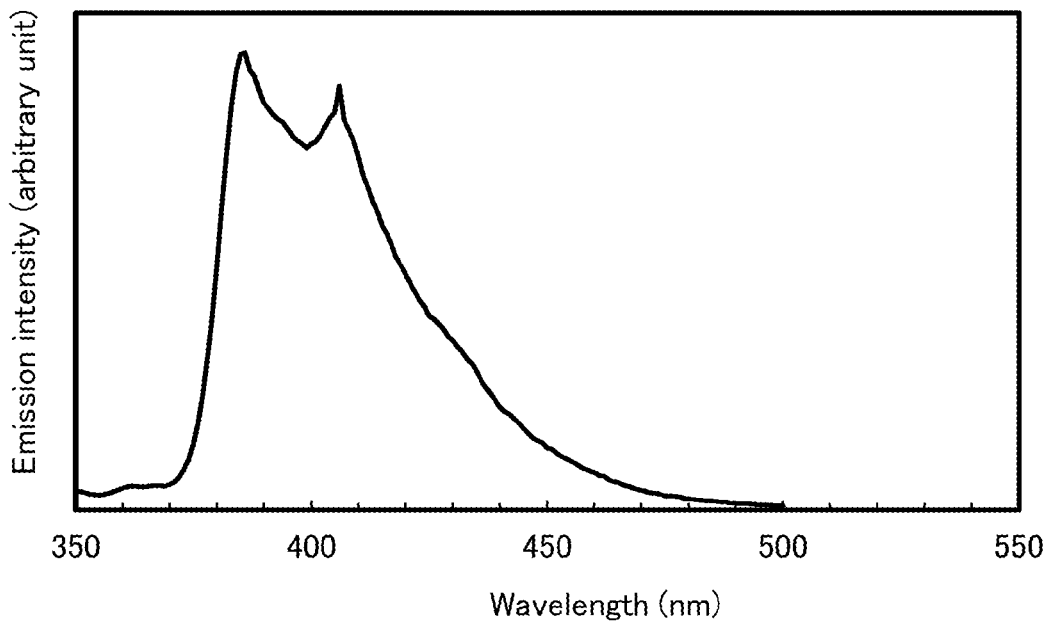
Figure 34A:
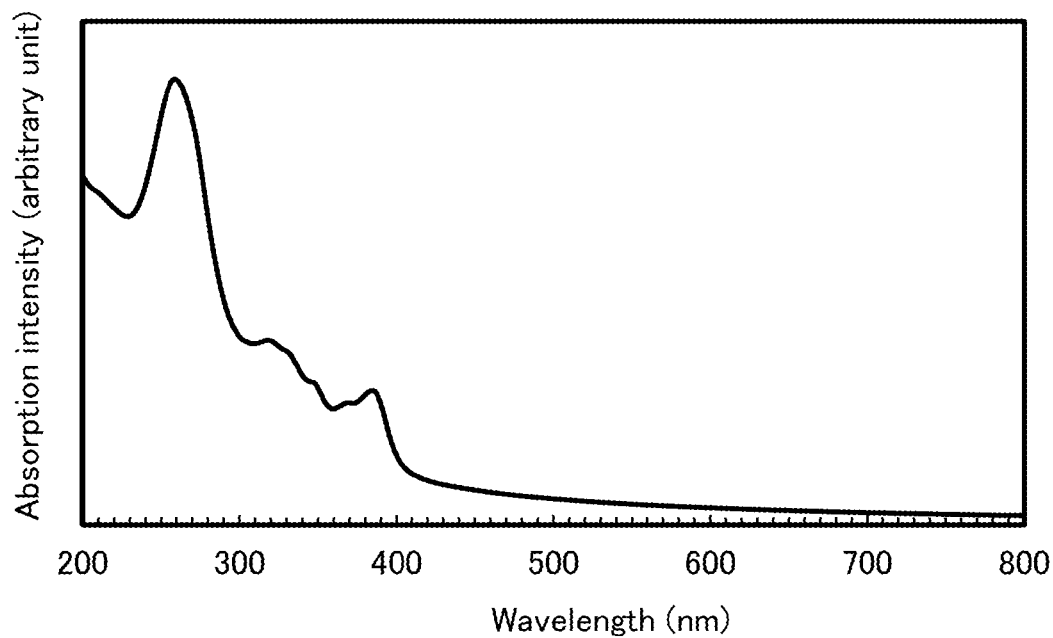
FIGS. 34A and 34B show an absorption spectrum and an emission spectrum of a thin film of 2mBnfBPDBq.
Figure 34B:
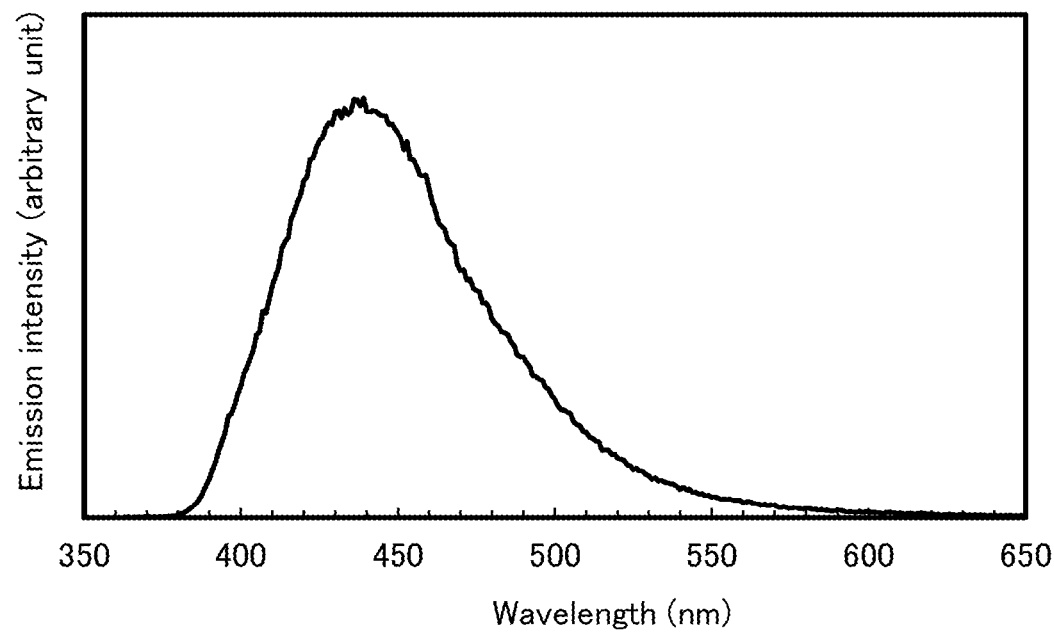

Further, FIG. 33A shows an absorption spectrum of 2mBnfBPDBq in a toluene solution of 2mBnfBPDBq, and FIG. 33B shows an emission spectrum thereof. FIG. 34A shows an absorption spectrum of a thin film of 2mBnfBPDBq and FIG. 34B shows an emission spectrum thereof. The spectra were calculated in a similar manner to Example 1. In FIGS. 33A and 33B and FIGS. 34A and 34B, the horizontal axis represents wavelength (nm) and the vertical axis represents intensity (arbitrary unit). In the case of the toluene solution, absorption peaks are observed around 355 nm and 368 nm, and emission wavelength peaks are observed at 386 nm and 406 nm (excitation wavelength: 330 nm). In the case of the thin film, absorption peaks are observed around 211 nm, 259 nm, 318 nm, 329 nm, 346 nm, 369 nm, and 384 nm, and an emission wavelength peak is observed at 437 nm (excitation wavelength: 347 nm).

EXAMPLE 7

In this example, the light-emitting element of one embodiment of the present invention will be described with reference to FIG. 10. Materials used in this example are the same as those used in the above examples, and their chemical formulae are omitted here.

A method for fabricating a light-emitting element 5 of this example will be described below.

(Light-Emitting Element 5)

In the light-emitting element 5, components other than the light-emitting layer 1113 and the electron-transport layer 1114 were formed in a similar manner to the light-emitting element 3. Here, only different steps from the method for fabricating the light-emitting element 3 are described.

The light-emitting layer 1113 of the light-emitting element 5 was formed by co-evaporation of 2mBnfBPDBq, PCBBiF, and [Ir(dppm)$_2$(acac)]. Here, a 20 nm thick layer which was formed with the weight ratio of 2mBnfBPDBq to PCBBiF and [Ir(dppm)$_2$(acac)] adjusted to 0.7:0.3:0.05 (=2mBnfBPDBq: PCBBiF: [Ir(dppm)$_2$(acac)]) and a 20 nm thick layer which was formed with the weight ratio adjusted to 0.8:0.2:0.05 (=2mBnfBPDBq: PCBBiF: [Ir(dppm)$_2$(acac)]) were stacked.

The electron-transport layer 1114 of the light-emitting element 5 was formed by depositing 2mBnfBPDBq to a thickness of 20 nm and further depositing BPhen to a thickness of 10 nm.

Table 7 shows an element structure of the light-emitting element fabricated as described above in this example.

TABLE 7

| | First Electrode | Hole-injection Layer | Hole-transport Layer | Light-emitting Layer | | Electron-transport Layer | Electron-injection Layer | Second Electrode |
|---|---|---|---|---|---|---|---|---|
| Light-emitting Element 5 | ITSO 110 nm | DBT3P-II:MoO$_x$ (=4:2) 20 nm | BPAFLP 20 nm | 2mBnfBPDBq:PCBBiF:[Ir(dppm)$_2$(acac)] (=0.7:0.3:0.05) 20 nm | (=0.8:0.2:0.05) 20 nm | 2mBnfBPDBq 20 nm | BPhen 10 nm | LiF 1 nm | Al 200 nm |

The light-emitting element of this example was sealed in a glove box under a nitrogen atmosphere so as not to be exposed to the air. Then, the operation characteristics of the light-emitting element were measured. Note that the measurement was carried out at room temperature (in an atmosphere kept at 25° C.).

Figure 35:
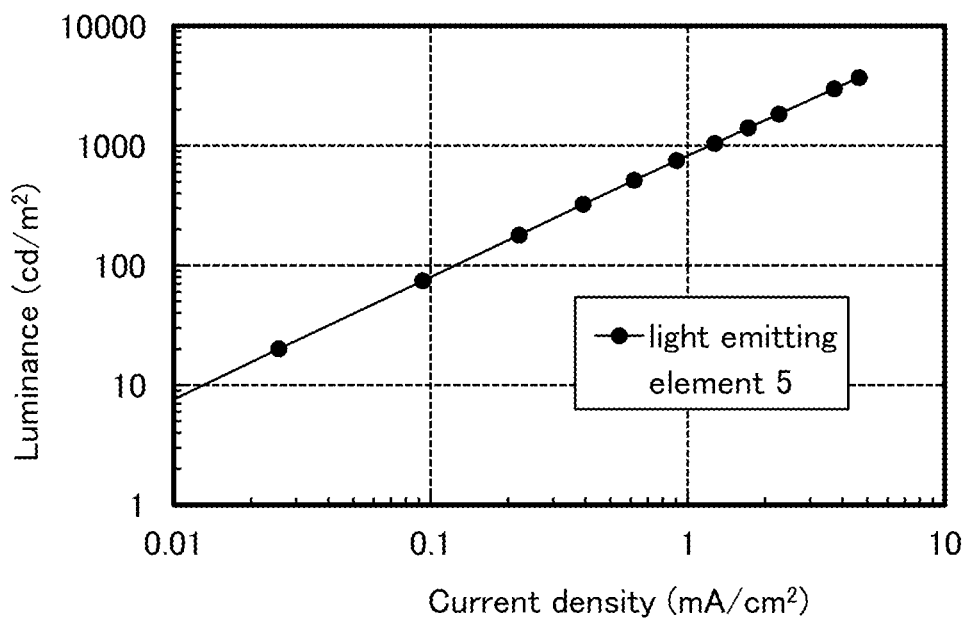
FIG. 35 shows current density-luminance characteristics of a light-emitting element in Example 7.
Figure 36:
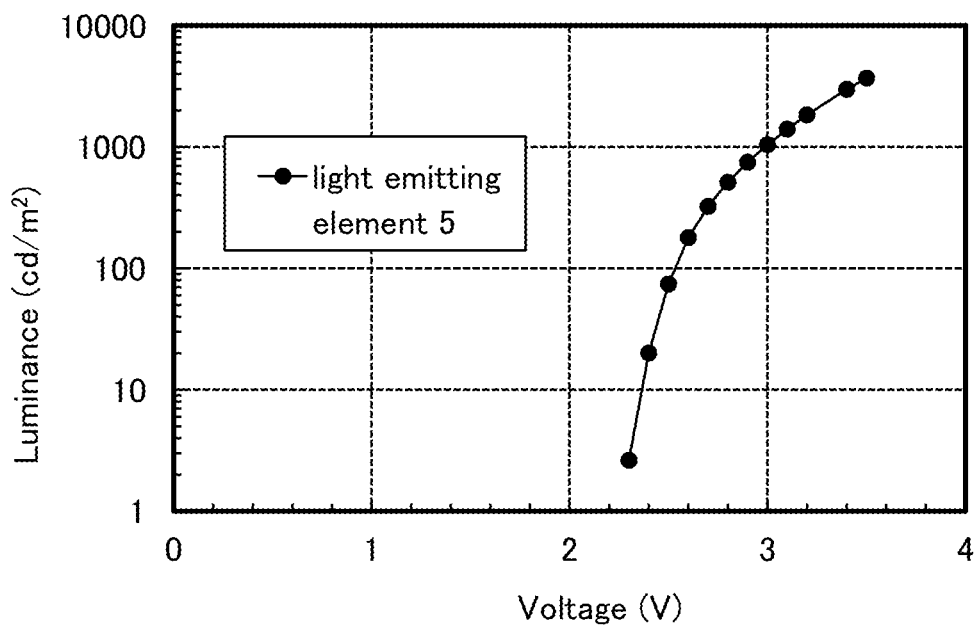
FIG. 36 shows voltage-luminance characteristics of the light-emitting element in Example 7.
Figure 37:
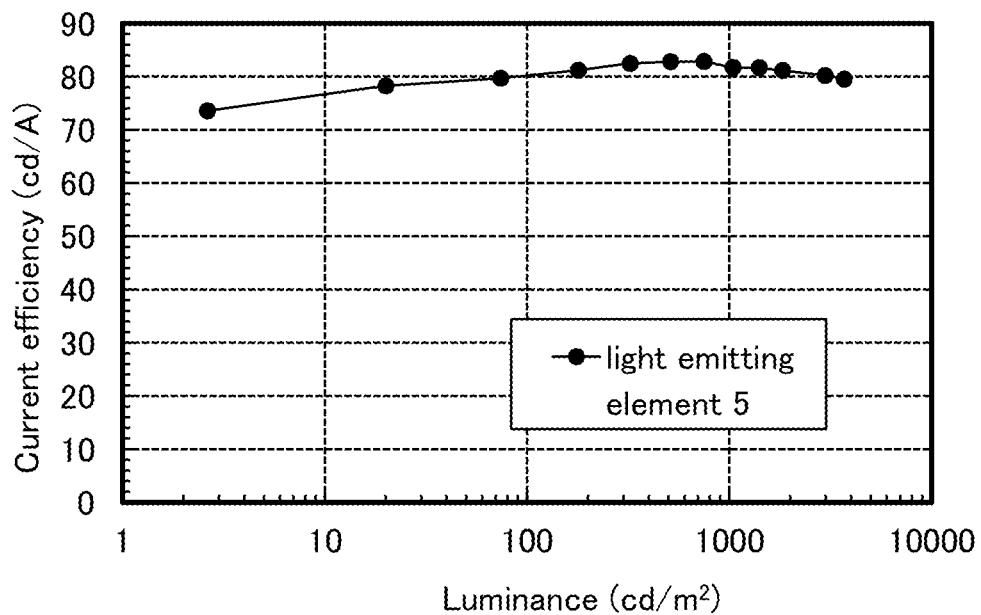
FIG. 37 shows luminance-current efficiency characteristics of the light-emitting element in Example 7.
Figure 38:
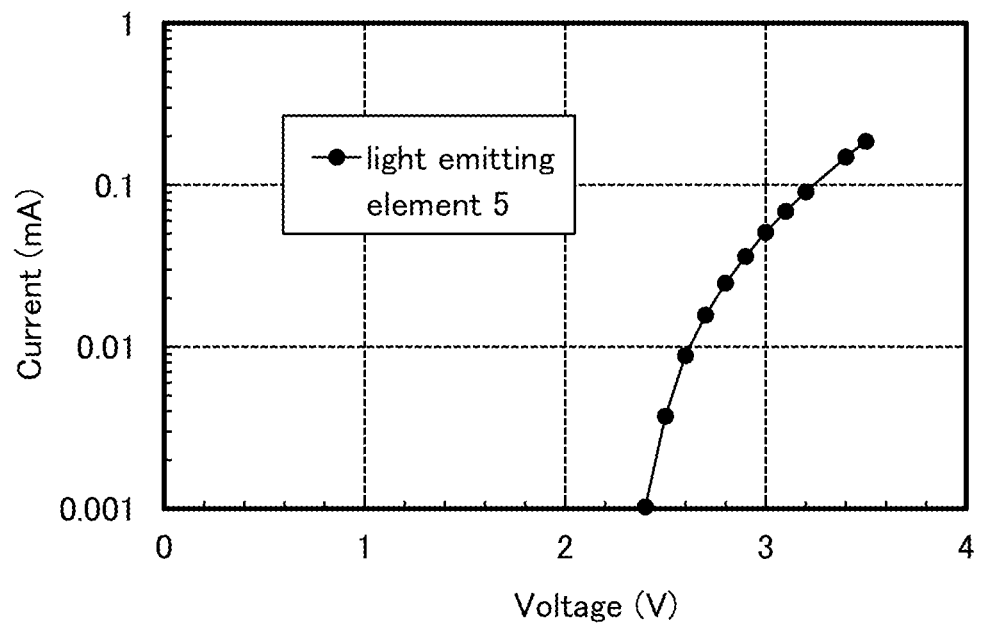
FIG. 38 shows voltage-current characteristics of the light-emitting element in Example 7.
Figure 39:
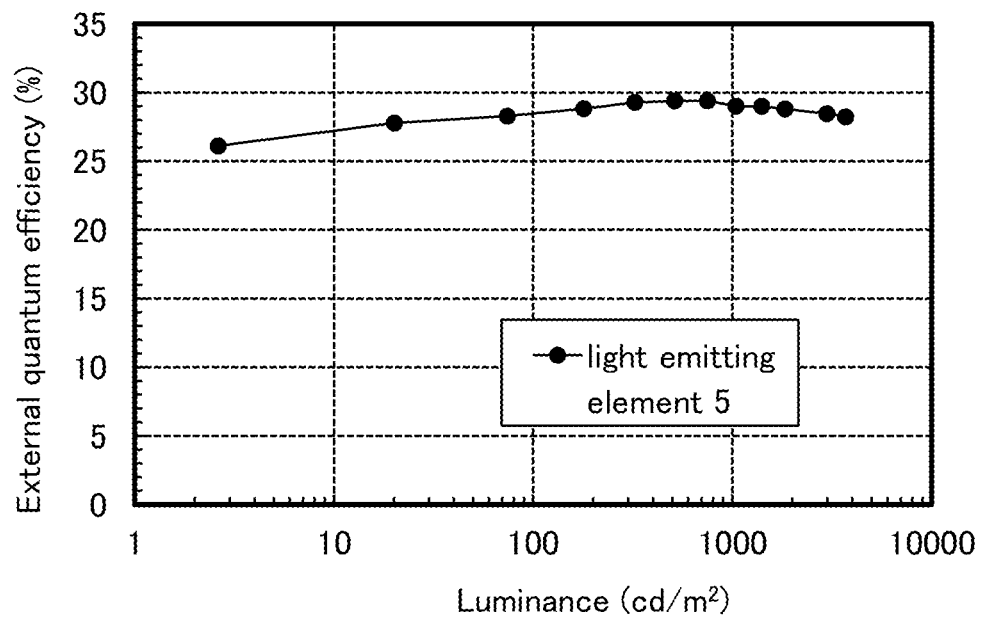
FIG. 39 shows luminance-external quantum efficiency characteristics of the light-emitting element in Example 7.

FIG. 35 shows current density-luminance characteristics of the light-emitting element 5. In FIG. 35, the horizontal axis represents current density (mA/cm$^2$), and the vertical axis represents luminance (cd/m$^2$). FIG. 36 shows voltage-luminance characteristics. In FIG. 36, the horizontal axis represents voltage (V) and the vertical axis represents luminance (cd/m$^2$). FIG. 37 shows luminance-current efficiency characteristics. In FIG. 37, the horizontal axis represents luminance (cd/m$^2$) and the vertical axis represents current efficiency (cd/A). FIG. 38 shows voltage-current characteristics. In FIG. 38, the horizontal axis represents voltage (V) and the vertical axis represents current (mA). FIG. 39 shows luminance-external quantum efficiency characteristics. In FIG. 39, the horizontal axis represents luminance (cd/m$^2$) and the vertical axis represents external quantum efficiency (%). Table 8 shows the voltage (V), current density (mA/cm$^2$), CIE chromaticity coordinates (x, y), current efficiency (cd/A), power efficiency (lm/W), and external quantum efficiency (%) of the light-emitting element 5 at a luminance of 1000 cd/m$^2$.

TABLE 8

| | Voltage (V) | Current Density (mA/cm$^2$) | Chromaticity x | Chromaticity y | Luminance (cd/m$^2$) | Current Efficiency (cd/A) | Power Efficiency (lm/W) | External Quantum Efficiency (%) |
|---|---|---|---|---|---|---|---|---|
| Light-emitting Element 5 | 3.0 | 1.3 | 0.55 | 0.44 | 1000 | 82 | 86 | 29 |

The CIE chromaticity coordinates (x, y) at a luminance of 1000 cd/m$^2$ of the light-emitting element 5 were (0.55, 0.44) and the light-emitting element 5 exhibited orange light emission. The results show that orange light emission originating from [Ir(dppm)$_2$(acac)] was provided from the light-emitting element 5.

The measurement results of the operation characteristics showed that the light-emitting element 5 has high emission efficiency and a low drive voltage.

Figure 40:
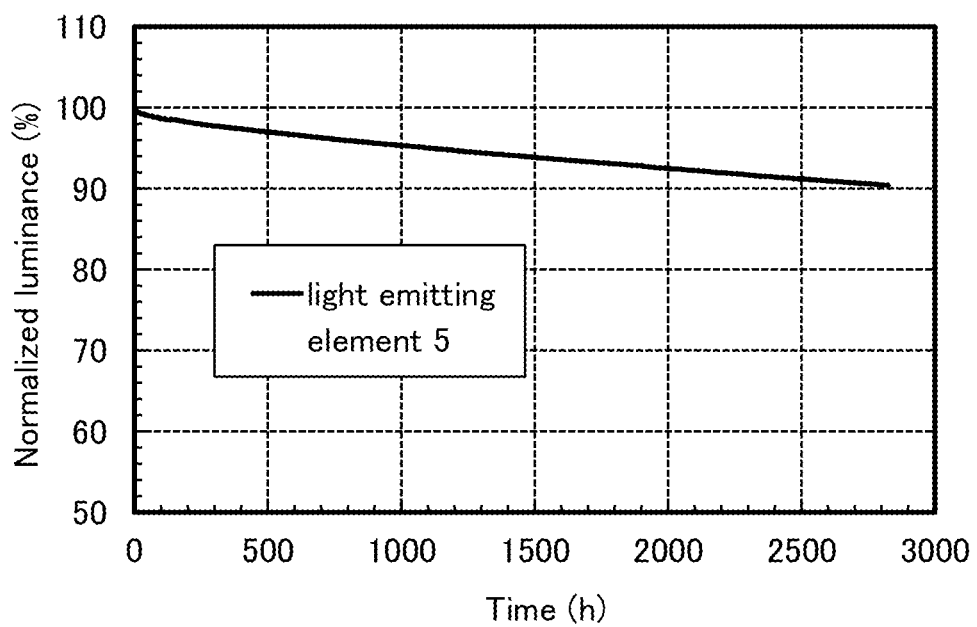
FIG. 40 shows results of a reliability test of the light-emitting element in Example 7.

A reliability test of the light-emitting element 5 was conducted. Results of the reliability test are shown in FIG. 40. In FIG. 40, the vertical axis represents normalized luminance (%) with the initial luminance taken as 100%, and the horizontal axis represents driving time (h) of the element. In the reliability test, which was conducted at room temperature, the light-emitting element 5 was driven under the conditions where the initial luminance was set to 5000 cd/m$^2$ and the current density was constant. FIG. 40 shows that the light-emitting element 5 kept 90% of the initial luminance after 2820 hours. The results of the reliability test showed that the light-emitting element 5 has a long lifetime.

REFERENCE NUMERALS

201: first electrode, 203: EL layer, 203a: first EL layer, 203b: second EL layer, 205: second electrode, 207: intermediate layer, 301: hole-injection layer, 302: hole-transport layer, 303: light-emitting layer, 304: electron-transport layer, 305: electron-injection layer, 401: supporting substrate, 403: light-emitting element, 405: sealing substrate, 407: sealant, 409a: first terminal, 409b: second terminal, 411a: light extraction structure, 411b: light extraction structure, 413: planarization layer, 415: space, 417: auxiliary wiring, 419: insulating layer, 421: first electrode, 423: EL layer, 425: second electrode, 501: supporting substrate, 503: light-emitting element, 504: light-emitting element, 505: sealing substrate, 506: desiccant, 507: sealant, 509: FPC, 511: first insulating layer, 513: second insulating layer, 515: space, 517: wiring, 519: partition, 521: first electrode, 523: EL layer, 525: second electrode, 531: black matrix, 533: color filter, 535: overcoat layer, 541a: transistor, 541b: transistor, 542: transistor, 543: transistor, 551: light-emitting portion, 551a: light-emitting portion, 551b: light-emitting portion, 552: driver circuit portion, 553: driver circuit portion, 561: first electrode, 563: EL layer, 565: second electrode, 1100: glass substrate, 1101: first electrode, 1103: second electrode, 1111: hole-injection layer, 1112: hole-transport layer, 1113: light-emitting layer, 1114: electron-transport layer, 1115: electron-injection layer, 7100: television device, 7101: housing, 7102: display portion, 7103: stand, 7111: remote controller, 7200: computer, 7201: main body, 7202: housing, 7203: display portion, 7204: keyboard, 7205: external connection port, 7206: pointing device, 7300: portable game machine, 7301a: housing, 7301b: housing, 7302: joint portion, 7303a: display portion, 7303b: display portion, 7304: speaker portion, 7305: recording medium insertion portion, 7306: operation key, 7307: connection terminal, 7308: sensor, 7400: mobile phone, 7401: housing, 7402: display portion, 7403: operation button, 7404: external connection port, 7405: speaker, 7406: microphone, 7500: tablet terminal, 7501a: housing, 7501b: housing, 7502a: display portion, 7502b: display portion, 7503: hinge, 7504:

power supply, 7505: operation key, 7506: speaker, 7601: lighting device, 7602: lighting device, 7603: desk lamp, 7604: planar lighting device, 7701: lighting portion, 7703: support, and 7705: supporting base.

This application is based on Japanese Patent Application serial no. 2012-243003 filed with Japan Patent Office on Nov. 2, 2012, the entire contents of which are hereby incorporated by reference.

The invention claimed is:

1. A heterocyclic compound represented by General Formula (G0)

$$A^1\text{-}Ar\text{-}A^2 \tag{G0}$$

wherein:
$A^1$ represents a dibenzo[f,h]quinoxalinyl group;
$A^2$ represents a benzo[b]naphtho[1,2-d]furanyl group;
Ar represents an arylene group having 6 to 13 carbon atoms; and
the dibenzo[f,h]quinoxalinyl group, the benzo[b]naphtho[1,2-d]furanyl group, and the arylene group separately are unsubstituted or have, as a substituent, an alkyl group having 1 to 4 carbon atoms or an aryl group having 6 to 13 carbon atoms.

2. A light-emitting element comprising a layer containing the heterocyclic compound according to claim 1 between a pair of electrodes.

3. A light-emitting device comprising the light-emitting element according to claim 2 in a light-emitting portion.

4. An electronic device comprising the light-emitting device according to claim 3 in a display portion.

5. A lighting device comprising the light-emitting device according to claim 3.

6. A heterocyclic compound represented by General Formula (G1)

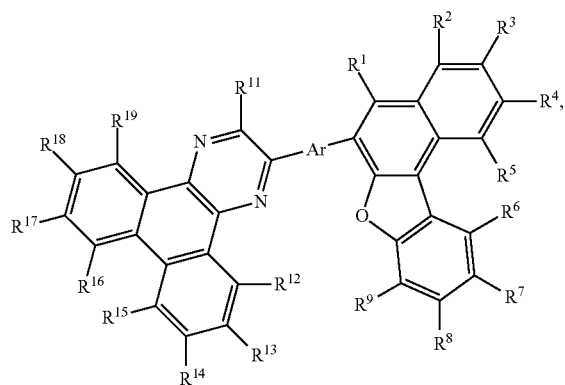

(G1)

wherein:
$R^1$ to $R^9$ and $R^{11}$ to $R^{19}$ separately represent hydrogen, an alkyl group having 1 to 4 carbon atoms, or an aryl group having 6 to 13 carbon atoms;
Ar represents an arylene group having 6 to 13 carbon atoms; and
the aryl group and the arylene group separately are unsubstituted or have, as a substituent, an alkyl group having 1 to 4 carbon atoms or an aryl group having 6 to 13 carbon atoms.

7. A light-emitting element comprising a layer containing the heterocyclic compound according to claim 6 between a pair of electrodes.

8. A light-emitting device comprising the light-emitting element according to claim 7 in a light-emitting portion.

9. An electronic device comprising the light-emitting device according to claim 8 in a display portion.

10. A lighting device comprising the light-emitting device according to claim 8.

11. A light-emitting element comprising a layer containing a heterocyclic compound between a pair of electrodes,
wherein the heterocyclic compound comprises a dibenzo[f,h]quinoxaline skeleton and a benzo[b]naphtho[1,2-d]furan skeleton.

12. A light-emitting device comprising the light-emitting element according to claim 11 in a light-emitting portion.

13. An electronic device comprising the light-emitting device according to claim 12 in a display portion.

14. A lighting device comprising the light-emitting device according to claim 12.

15. A light-emitting element comprising a layer containing a heterocyclic compound between a pair of electrodes,
wherein the heterocyclic compound is a heterocyclic compound in which a dibenzo[f,h]quinoxaline skeleton and a benzo[b]naphtho[1,2-d]furan skeleton are bonded through an arylene skeleton.

16. A light-emitting device comprising the light-emitting element according to claim 15 in a light-emitting portion.

17. An electronic device comprising the light-emitting device according to claim 16 in a display portion.

18. A lighting device comprising the light-emitting device according to claim 16.

* * * * *